(12) United States Patent
Cole et al.

(10) Patent No.: US 9,790,215 B2
(45) Date of Patent: *Oct. 17, 2017

(54) PYRIDAZINONE COMPOUNDS AND METHODS FOR THE TREATMENT OF CYSTIC FIBROSIS

(71) Applicant: FLATLEY DISCOVERY LAB, LLC, Charlestown, MA (US)

(72) Inventors: Bridget M. Cole, Quincy, MA (US); Richard A. Nugent, Ashland, MA (US); Andrew Kolodziej, Winchester, MA (US); Karen Handley, Londonderry, NH (US); Yevgen Barsukov, Brookline, MA (US)

(73) Assignee: FLATLEY DISCOVERY LAB, LLC, Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/210,273

(22) Filed: Mar. 13, 2014

(65) Prior Publication Data
US 2014/0371225 A1   Dec. 18, 2014

Related U.S. Application Data

(60) Provisional application No. 61/778,870, filed on Mar. 13, 2013.

(51) Int. Cl.

| | | |
|---|---|---|
| *A61K 31/502* | (2006.01) | |
| *C07D 487/00* | (2006.01) | |
| *C07D 413/12* | (2006.01) | |
| *A61K 45/06* | (2006.01) | |
| *C07D 413/14* | (2006.01) | |
| *C07D 498/04* | (2006.01) | |
| *A61K 31/38* | (2006.01) | |
| *A61K 31/4245* | (2006.01) | |
| *A61K 31/443* | (2006.01) | |
| *A61K 31/47* | (2006.01) | |
| *A61K 31/5025* | (2006.01) | |
| *A61K 31/506* | (2006.01) | |
| *A61K 31/519* | (2006.01) | |
| *C07D 237/32* | (2006.01) | |
| *C07D 401/04* | (2006.01) | |
| *C07D 401/06* | (2006.01) | |
| *C07D 405/04* | (2006.01) | |
| *C07D 405/12* | (2006.01) | |
| *C07D 405/14* | (2006.01) | |
| *C07D 487/04* | (2006.01) | |
| *A61K 31/5377* | (2006.01) | |
| *C07D 401/12* | (2006.01) | |
| *C07D 401/14* | (2006.01) | |

(Continued)

(52) U.S. Cl.
CPC ........ *C07D 413/12* (2013.01); *A61K 31/38* (2013.01); *A61K 31/4245* (2013.01); *A61K 31/443* (2013.01); *A61K 31/47* (2013.01); *A61K 31/502* (2013.01); *A61K 31/506* (2013.01); *A61K 31/5025* (2013.01); *A61K 31/519* (2013.01); *A61K 31/5377* (2013.01); *A61K 45/06* (2013.01); *C07D 237/32* (2013.01); *C07D 401/04* (2013.01); *C07D 401/06* (2013.01); *C07D 401/12* (2013.01); *C07D 401/14* (2013.01); *C07D 403/04* (2013.01); *C07D 405/04* (2013.01); *C07D 405/12* (2013.01); *C07D 405/14* (2013.01); *C07D 413/14* (2013.01); *C07D 417/14* (2013.01); *C07D 487/04* (2013.01); *C07D 495/14* (2013.01); *C07D 498/04* (2013.01); *C07D 519/00* (2013.01)

(58) Field of Classification Search
CPC ... A61K 31/502; C07D 237/26; C07D 487/00
USPC .................. 544/224, 235; 514/247, 248
See application file for complete search history.

(56) References Cited

U.S. PATENT DOCUMENTS

| | | |
|---|---|---|
| 3,813,384 A | 5/1974 | Vogelsang |
| 4,665,181 A | 5/1987 | Thomas et al. |

(Continued)

FOREIGN PATENT DOCUMENTS

| | | |
|---|---|---|
| CN | 101757625 A | 6/2010 |
| CN | 101781248 A | 7/2010 |

(Continued)

OTHER PUBLICATIONS

Horn et al (1991): STN International HCAPLUS database, (Columbus, Ohio), Accession No. 1991:408820.*
Chemical Abstracts Registry entry #920811-87-6, entered into STN on Feb. 14, 2007, downloaded from STN file Registry.
Co-pending U.S. Appl. No. 14/210,261, filed Mar. 13, 2014.
Co-pending U.S. Appl. No. 14/210,277, filed Mar. 13, 2014.
Cohen-Cymberknoh, M., et al., "Concise Clinical Review. Managing Cystic Fibrosis: Strategies That Increase Life Expectancy and Improve Quality of Life," Am J Respir Crit Care Med, 183: 1463-1471 (2011).

(Continued)

*Primary Examiner* — Golam M M Shameem
(74) *Attorney, Agent, or Firm* — Elmore Patent Law Group, P.C.; Edgar Harlan; Carolyn Elmore

(57) ABSTRACT

The invention relates to a compound of Formula I and methods of treating cystic fibrosis comprising the step of administering a therapeutically effective amount of a compound of Formula I to a patient in need thereof:

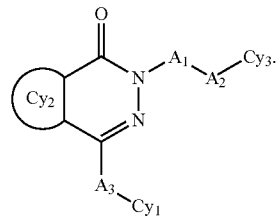

Formula I

10 Claims, No Drawings

(51) Int. Cl.
  *C07D 403/04* (2006.01)
  *C07D 417/14* (2006.01)
  *C07D 495/14* (2006.01)
  *C07D 519/00* (2006.01)

(56) References Cited

U.S. PATENT DOCUMENTS

| | | |
|---|---|---|
| 5,110,814 A | 5/1992 | Engel et al. |
| 5,668,279 A | 9/1997 | Chakravarty et al. |
| 6,103,718 A | 8/2000 | Sterk |
| 6,180,629 B1 | 1/2001 | Wang et al. |
| 6,255,303 B1 | 7/2001 | Sterk et al. |
| 6,498,160 B2 | 12/2002 | Napoletano et al. |
| 6,544,993 B1 | 4/2003 | Sterk |
| 6,924,284 B2 | 8/2005 | Beaton et al. |
| 7,186,710 B2 | 3/2007 | Sterk |
| 7,432,263 B2 | 10/2008 | Pulici |
| 7,470,688 B2 | 12/2008 | Javaid et al. |
| 7,501,410 B2 | 3/2009 | Goldstein et al. |
| 8,937,178 B2 * | 1/2015 | Cole ............................ 544/238 |
| 2003/0105328 A1 | 6/2003 | Strehlke et al. |
| 2004/0192695 A1 | 9/2004 | Petrov et al. |
| 2005/0059663 A1 | 3/2005 | Martin et al. |
| 2008/0161280 A1 | 7/2008 | Gandhi et al. |
| 2008/0269234 A1 | 10/2008 | Gandhi et al. |
| 2008/0286204 A1 | 11/2008 | Hadida-Ruah |
| 2009/0163545 A1 | 6/2009 | Goldfarb et al. |
| 2011/0105509 A1 | 5/2011 | Kaila et al. |
| 2011/0124642 A1 | 5/2011 | Brown et al. |
| 2011/0257115 A1 | 10/2011 | Leighton et al. |
| 2012/0149690 A1 | 6/2012 | Dang et al. |
| 2013/0023520 A1 | 1/2013 | Jalali |

FOREIGN PATENT DOCUMENTS

| | | |
|---|---|---|
| CN | 102078612 A | 6/2011 |
| CN | 102391253 A | 3/2012 |
| CN | 102451167 A | 5/2012 |
| DE | 286354 A5 | 1/1991 |
| EP | 0316633 A1 | 5/1989 |
| EP | 0580074 A1 | 1/1994 |
| EP | 0590551 A2 | 4/1994 |
| EP | 634413 A1 | 1/1995 |
| EP | 0934933 A1 | 8/1999 |
| EP | 2072510 A1 | 6/2009 |
| JP | 56-061365 A | 5/1981 |
| JP | 2008101027 A | 5/2008 |
| JP | 2008101028 A | 5/2008 |
| JP | 2008101029 A | 5/2008 |
| JP | 2008110970 A | 5/2008 |
| JP | 2008169193 A | 7/2008 |
| JP | 2009007332 A | 1/2009 |
| JP | 2009108042 A | 5/2009 |
| JP | 2009108044 A | 5/2009 |
| JP | 2009242303 A | 10/2009 |
| JP | 2010260808 A | 11/2010 |
| JP | 2011084521 A | 4/2011 |
| JP | 2012020961 | 2/2012 |
| WO | 9307146 A1 | 4/1993 |
| WO | 0160407 A2 | 8/2001 |
| WO | 0236576 A1 | 5/2002 |
| WO | 03105856 A1 | 12/2003 |
| WO | 2004019955 A1 | 3/2004 |
| WO | 2004080976 A1 | 9/2004 |
| WO | 2005074983 A2 | 8/2005 |
| WO | 2006002421 A2 | 1/2006 |
| WO | 2006/034419 A2 | 3/2006 |
| WO | 2006032518 A1 | 3/2006 |
| WO | 2006102494 A2 | 9/2006 |
| WO | 2006124874 A2 | 11/2006 |
| WO | 2006131737 A2 | 12/2006 |
| WO | 2007026151 A1 | 3/2007 |
| WO | 2007056341 A1 | 5/2007 |
| WO | 2007079139 A2 | 7/2007 |
| WO | 2007134279 A2 | 11/2007 |
| WO | 2008012338 A2 | 1/2008 |
| WO | 2008/019292 A2 | 2/2008 |
| WO | 2008070264 A2 | 6/2008 |
| WO | 2009023509 A2 | 2/2009 |
| WO | 2009054952 A2 | 4/2009 |
| WO | 2009073757 A1 | 6/2009 |
| WO | 2009076141 A2 | 6/2009 |
| WO | 2009076142 A2 | 6/2009 |
| WO | 2009/123870 A1 | 10/2009 |
| WO | 2009124167 | 10/2009 |
| WO | 2010019239 A2 | 2/2010 |
| WO | 2010037066 A2 | 4/2010 |
| WO | 2010053471 A1 | 5/2010 |
| WO | 2011008931 A2 | 1/2011 |
| WO | 2011019413 A1 | 2/2011 |
| WO | 2011050325 A1 | 4/2011 |
| WO | 2011116397 A1 | 9/2011 |
| WO | 2011119984 A1 | 9/2011 |
| WO | 2011127241 A2 | 10/2011 |
| WO | 2011127290 A2 | 10/2011 |
| WO | 2011133751 A2 | 10/2011 |
| WO | 2011133951 A1 | 10/2011 |
| WO | 2011133953 A1 | 10/2011 |
| WO | 2011146901 A1 | 11/2011 |
| WO | 2012074231 A2 | 6/2012 |
| WO | 2013068876 A1 | 5/2013 |
| WO | 2013083569 A1 | 6/2013 |
| WO | 2013177594 A2 | 11/2013 |

OTHER PUBLICATIONS

Cuthbert, A.W., "Review: New horizons in the treatment of cystic fibrosis," British Journal of Pharmacology, 163: 173-183 (2010).
Devor, D. C., et al., "Pharmacological modulation of ion transport across wildtype and ΔF508 CFTR-expressing human bronchial epithelia," Am J Physiol Cell Physiol, 279: C461-C479 (2000).
Sui, J., et al., "Optimization of a Yellow Fluorescent Protein-Based Iodide Influx High-Throughput Screening Assay for Cystic Fibrosis Transmembrane Conductance Regulator (CFTR) Modulators," Assay and Drug Development Technologies, 8(6): 1-15 (2010).
Mohamed, F. K., "Synthesis, reactions and antimicrobial activity on some novel phthalazinone derivatives," Der Pharma Chemica, 2010, 2(3): 267-276 (http://derpharmachemica.com/archive.html).
Mohamed, F. K., "Synthesis, reactions and antimicrobial activity on some novel phthalazinones derivatives," Der Chemica Sinica, 2010, 1 (1): 20-31. (www.pelagiaresearchlibrary.com).
Sriram, D., et al., "Synthesis and antimycobacterial evaluation of novel phthalazin-4-ylacetamides against log- and starved phase cultures," Chemical Biology & Drug Design, 2010, 75(4): 381-391 (Abstract only).
Demirayak, S., et al., "Some pyridazinone and phthalazinone derivatives and their vasodilator activities," Archives of Pharmacal Research, 27(1): 13-18 (2004), Abstract only.
El-Gendy, et al., "Synthesis and Reactions of Phthalazine Derivatives," Indian Journal of Chemistry, Section B: Organic Chemistry Including Medicinal Chemistry, 1989, 647-53, Abstract only.
Silverman, R. B., "The Organic Chemistry of Drug Design and Drug Action" Published by Academic Press (1992) pp. 4-46 and 352-397.
Wolff, M. E., "Burger's Medicinal Chemistry and Drug Discovery, Fifth Edition, vol. I: Principles and Practice" published by John Wiley and Sons (1994) pp. 975-977.
Testa, B., "Prodrug Research: Futile or Fertile?" Biochemical Pharmacology (2004) vol. 68 pp. 2097-2106.
Stella, V. J., "Prodrugs as Therapeutics", Expert Opinion on Therapeutic Patents (2004) vol. 14 (No. 3), pp. 277-280.
Ettmayer, P., et al., "Lessons Learned from Marketed and Investigational Prodrugs," Journal of Medicinal Chemistry (2004) vol. 47(10), pp. 2393-2404.
Capelli, A. M., et al., "Identification of novel α7 nAChR positive allosteric modulators with the use of pharmacophore in silico screening methods," Bioorganic & Medicinal Chemistry Letters, 20: 4561-4565 (2010).

(56) References Cited

OTHER PUBLICATIONS

CAS RN 902597-26-6, STN Entry Date Aug. 18, 2006; CAS RN 902597-18-6, STN Entry Date Aug. 18, 2006; CAS RN 902500-57-6, STN Entry Date Aug. 17, 2006; CAS RN 902500-40-7, STN Entry Date Aug. 17, 2006; CAS RN 902499-88-1, STN Entry Date Aug. 17, 2006; CAS RN 896830-26-5, STN Entry Date Jul. 28, 2006; CAS RN 736965-46-1, STN Entry Date Sep. 1, 2004; CAS RN 364612-61-3, STN Entry Date Oct. 25, 2001; CAS RN 364612-60-2, STN Entry Date Oct. 25, 2001.

CAS RN 899386-28-8, STN Entry Date Aug. 7, 2006; CAS RN 840463-50-5, STN Entry Date Mar. 2, 2005; CAS RN 799811-17-9, STN Entry Date Dec. 20, 2004; CAS RN 702647-29-8, STN Entry Date Jul. 2, 2004; CAS RN 695200-56-7, STN Entry Date Jun. 18, 2004; CAS RN 684234-59-1, STN Entry Date May 21, 2004.

Van Der Mey, M., et al., "Synthesis and Structure-Activity Relationships of cis-Tetrahydrophthalazinone/Pyridazinone Hybrids: A Novel Series of Potent Dual PDE3/PDE4 Inhibitory Agents," J. Med. Chem., 46: 2008-2016 (2003).

Kolobov, A. V. et al. "6-Aryl-2H-pyridazin-3-ones and 4-aryl-5,6,7,8-tetrahydro-2Hphthalazine-1-ones: synthesis and N-alkylation reactions" Izvestiya Vysshikh Uchebnykh Zavedenii, Khimiya i Khimicheskaya Tekhnologiya (2006), 49(3), pp. 24-28.

Bobova, T. A., et al., "Alkylation of 4-R-substituted-2H-phthalazin-1-ones" Izvestiya Vysshikh Uchebnykh Zavedenii, Khimiya i Khimicheskaya Tekhnologiya (2011), 54(11), pp. 41-43.

Segura-Cabrera, A., et al., "Integrative computational protocol for the discovery of inhibitors of the Helicobacter pylori nickel response regulator (NikR)," Journal of Molecular Modeling (Dec. 31, 2011), 17(12), pp. 3075-3084.

Yassin, F. A., et al., "Synthesis of 4,5,6,7-tetraphenyl-8-(substituted)-3(2H)-phthalazinone derivatives likely to possess antihypertensive activity" Bulletin of the Korean Chemical Society (Feb. 20, 1990), 11(1), pp. 7-10.

CAS RN 1359474-16-0, STN Entry Date Mar. 12, 2012; CAS RN 1357902-01-2, STN Entry Date Feb. 28, 2012; CAS RN 1115930-01-2, STN Entry Date Mar. 5, 2009; CAS RN 920684-42-0, STN Entry Date Feb. 13, 2007; CAS RN 902597-26-6, STN Entry Date Aug. 18, 2006; CAS RN 902597-18-6, STN Entry Date Aug. 18, 2006; CAS RN 736965-46-1, STN Entry Date Sep. 1, 2004; CAS RN 931685-00-6, STN Entry Date Apr. 22, 2007; CAS RN 920677-37-8, STN Entry Date Feb. 13, 2007; CAS RN 902596-62-7, STN Entry Date Aug. 18, 2006.

CAS RN 902499-72-3, STN Entry Date Aug. 18, 2006; CAS RN 902165-32-6, STN Entry Date Aug. 17, 2006; CAS RN 1387400-35-2, STN Entry Date Aug. 7, 2012; CAS RN 1214400-23-3, STN Entry Date Mar. 25, 2010; CAS RN 920811-87-6, STN Entry Date Feb. 14, 2007; CAS RN 920726-70-1, STN Entry Date Feb. 13, 2007; CAS RN 896815-44-4, STN Entry Date Jul. 28, 2006; CAS RN 896594-33-5, STN Entry Date Jul. 28, 2006; CAS RN 896073-38-4, STN Entry Date Jul. 25, 2006.

CAS RN 840463-36-7, CAS RN 1116070-76-8, CAS RN 1115976-21-0, CAS RN 1251694-86-6 all retrieved from www.chemspider.com/Chemical Structure.

CAS RN 1356731-74-2, STN Entry Date Feb. 14, 2012; CAS RN 1325474-52-9, STN Entry Date Aug. 30, 2011; CAS RN 1324990-51-3, STN Entry Date Aug. 29, 2011; CAS RN 913687-55-5, STN Entry Date Nov. 21, 2006; CAS RN 930018-50-1, STN Entry Date Apr. 13, 2007; CAS RN 1118853-08-9, STN Entry Date Mar. 11, 2009.

El-Hashash, M., et al, "Synthesis and Antimicrobial Activity of Some Condensed [4-(2,4,6-Trimethylphenyl)-1(2H)-oxo-phthalazin-2-yl]acetic Acid Hydrazide," Chinese Journal of Chemistry, 2012, 30, 616-626.

Yassin, F. et al, "Synthesis and reactions of oxadiazolo, thiadiazolo and triazolo phthalazin-1(2H)-one derivatives." Der Pharma Chemica, 2012, 4(3), 860-866.

Bayoumy, B. et al, "Synthesis of Some Newer Oxadiazolo-, Oxadiazolino-, Thiadiazolo-, and Triazolothiadiazino-phthalazinone Derivatives." Egyptian Journal of Chemistry, 1990, 33(3), 267-275.

Kassab, E. "Synthesis and Behaviour of 4-(4'-Chloro-3'-Methyl Phenyl)-1(2H)-Phthalazinone towards Certain Electrophiles and Nucleophiles." Egyptian Journal of Chemistry, 2005, 48(2), 183-199.

Abd Alla, M. et al, "Synthesis and anti-inflammatory evaluation of some condensed [4-(3,4-dimethylphenyl)-1(2H)-oxo-phthalazin-2-yl]acetic acid hydrazide." European Journal of Medicinal Chemistry, 2010, 45, 1267-1277.

CAS RN 1061505-98-3, STN Entry Date Oct. 15, 2008.
CAS RN 1251574-92-1, STN Entry Date Nov. 3, 2010.
CAS RN 664978-35-2, STN Entry Date Mar. 19, 2004.
CAS RN 902164-83-4, STN Entry Date Aug. 17, 2006.
CAS RN 902596-35-4, STN Entry Date Aug. 18, 2006.
CAS RN 902165-28-0, STN Entry Date Aug. 17, 2006.

* cited by examiner

PYRIDAZINONE COMPOUNDS AND METHODS FOR THE TREATMENT OF CYSTIC FIBROSIS

RELATED APPLICATION

This application claims the benefit of U.S. Provisional Application No. 61/778,870, filed on Mar. 13, 2013. The entire teachings of the above application are incorporated herein by reference.

BACKGROUND

Cystic fibrosis (CF) is a lethal, recessive, genetic disease affecting approximately 1 in 2500 live births among Caucasians. (Cohen-Cymberknoh, M. et al., *Am. J. Respir. Crit. Care Med.* 1463-1471, 2011; Boat et al., The Metabolic Basis of Inherited Disease, 6th ed, pp 2649-2680, McGraw Hill, NY (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. (Hantash F: U.S. Patent Application No. 20060057593). The CF gene codes for a cAMP/PKA-dependent, ATP-requiring, membrane chloride ion channel, generally found in the apical membranes of many secreting epithelia and known as CFTR (cystic fibrosis transmembrane conductance regulator). There are currently over 1700 known mutations affecting CFTR, many of which give rise to a disease phenotype. Around 75% of CF alleles contain the ΔF508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cuthbert A W, *British Journal of Pharmacology*, 163(1), 173-183, 2011).

Mutations in the CFTR gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths. (Cohen-Cymberknoh, M et al., *Am. J. Respir. Crit. Care Med.* 1463-1471, 2011).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C. et. al., *Expert Opin Pharmacother.* 10(7), 1191-202, 2009).

SUMMARY

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I to a patient in need thereof:

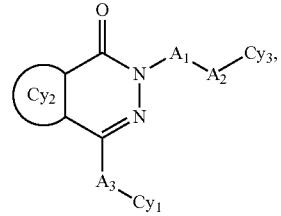

Formula I $A_1$ is absent, —[C($R_{100}$)($R_{101}$)]n-, —C(O)—, —C(S)—, —S(O)—, —C(O)N($R_{100}$)—, —S(O)$_2$—, carbocycle, substituted carbocycle, heterocycle, substituted heterocycle, aromatic, substituted aromatic, heteroaromatic or substituted heteroaromatic;

wherein n is 0, 1, 2, 3, 4, 5, 6 or 7;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —[C($R_{100}$)($R_{101}$)]$_n$—, —C(O)—, —C(S)—, —S(O)—, —C(O)N($R_{100}$)—, —C(O)N($R_{100}$)($R_{101}$), N($R_{100}$)($R_{101}$), —S(O)$_2$—, —S(O)$_2R_{100}$, —S(O)$R_{100}$, —S(O)$_2$N($R_{100}$)$R_{101}$);

$A_3$ is a bond or —[C($R_{100}$)($R_{101}$)]$_n$—, —C(O)—, —C(S)—, —S(O)—, —C(O)N($R_{100}$)—, —C(O)N($R_{100}$)($R_{101}$), N($R_{100}$)($R_{101}$), —S(O)$_2$—, S(O)$_2R_{100}$, S(O)$R_{100}$, S(O)$_2$N($R_{100}$)$R_{101}$);

$Cy_1$ is absent, an aryl, substituted aryl, carbocycle, substituted carbocycle, heterocyclyl, substituted heterocyclyl, heteroaryl, or substituted heteroaryl group having one, two or three rings;

$Cy_2$ is an aryl, substituted aryl, carbocycle, substituted carbocycle, heterocyclyl, substituted heterocyclyl, heteroaryl, or substituted heteroaryl group having one, two or three rings; and $Cy_3$ is absent, an aryl, substituted aryl, carbocycle, substituted carbocycle, heterocyclyl, substituted heterocyclyl, heteroaryl, or substituted heteroaryl group having one, two or three rings.

DETAILED DESCRIPTION OF THE INVENTION

The invention relates to a compound of Formula I and methods of treating cystic fibrosis comprising the step of administering a therapeutically effective amount of a compound of Formula I to a patient in need thereof:

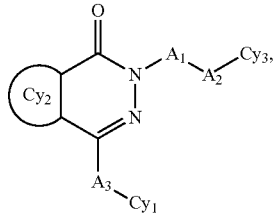

Formula I $A_1$ is absent, —[C($R_{100}$)($R_{101}$)]$_n$—, —C(O)—, —C(S)—, —S(O)—, —C(O)N($R_{100}$)—, —S(O)$_2$N($R_{100}$)—, —S(O)$_2$—, carbocycle, substituted carbocycle, heterocycle, substituted heterocycle, aromatic, substituted aromatic, heteroaromatic or substituted heteroaromatic;

wherein n is 0, 1, 2, 3, 4, 5, 6 or 7;

wherein each $R_{100}$ and $R_{101}$ is hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two of $R_{100}$ and $R_{101}$ groups together with the atoms to which they are attached and any intervening atoms may form an additional optionally substituted, 3, 4, 5, 6 or 7 membered ring;

$A_2$ is absent or —[C($R_{100}$)($R_{101}$)]$_n$—, —C(O)—, —C(S)—, —S(O)—, —C(O)N($R_{100}$)—, —C(O)N($R_{100}$)($R_{101}$), N($R_{100}$)($R_{101}$), —S(O)$_2$—, —S(O)$_2$$R_{100}$, —S(O)$R_{100}$, —S(O)$_2$N($R_{100}$)$R_{101}$);

$A_3$ is absent or —[C($R_{100}$)($R_{101}$)]$_n$—, —C(O)—, —C(S)—, —S(O)—, —C(O)N($R_{100}$)—, —C(O)N($R_{100}$)($R_{101}$), N($R_{100}$)($R_{101}$), —S(O)$_2$—, S(O)$_2$$R_{100}$, S(O)$R_{100}$, S(O)$_2$N($R_{100}$)($R_{101}$);

$Cy_1$ is absent, an aryl, substituted aryl, carbocycle, substituted carbocycle, heterocyclyl, substituted heterocyclyl, heteroaryl, or substituted heteroaryl group having one, two or three rings;

$Cy_2$ is an aryl, substituted aryl, carbocycle, substituted carbocycle, heterocyclyl, substituted heterocyclyl, heteroaryl, or substituted heteroaryl group having one, two or three rings; and $Cy_3$ is absent, an aryl, substituted aryl, carbocycle, substituted carbocycle, heterocyclyl, substituted heterocyclyl, heteroaryl, or substituted heteroaryl group having one, two or three rings.

In a preferred embodiment, the invention relates to a compound having the formula:

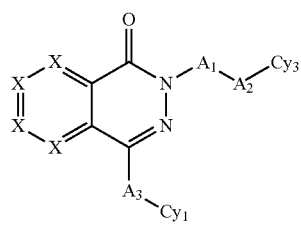

wherein each X is independently, —C$R_{100}$— or —N—.

In a preferred embodiment, the invention relates to a compound wherein X is —C($R_{100}$) and wherein $R_{100}$ is preferred as H, halogen, alkoxy or alkyl.

In a preferred embodiment, the invention relates to a compound having the formula:

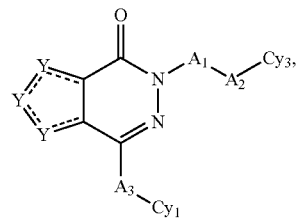

wherein each Y is independently —C$R_{100}$—, —N$R_{100}$, —N, —O or —S.

In a preferred embodiment, the invention relates to a compound having the formula:

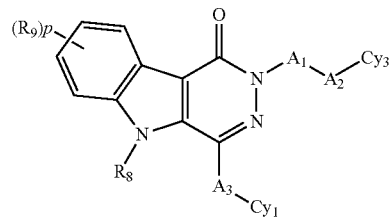

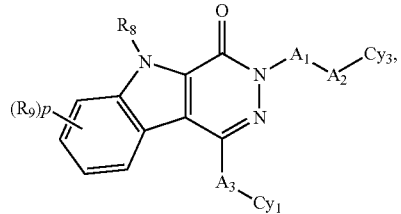

wherein p is 0, 1, 2, 3 or 4; and wherein $R_8$ is hydrogen, deuterium, alkyl, substituted alkyl, alkenyl, substituted alkenyl, alkynyl, substituted alkynyl, aliphatic, substituted aliphatic, carbocycle, substituted carbocycle, aryl, substituted aryl, heterocyclyl, substituted heterocyclyl, heteroaryl, or substituted heteroaryl; and $R_9$ is independently selected from hydrogen, deuterium, halo, alkyl, substituted alkyl, alkenyl, substituted alkenyl, alkynyl, substituted alkynyl, aliphatic, substituted aliphatic, carbocycle, substituted carbocycle, aryl, substituted aryl, heterocyclyl, substituted heterocyclyl, heteroaryl, or substituted heteroaryl —O$R_{100}$, —N$R_{100}$$R_{101}$, —C(O)$R_{100}$, —C(O)O$R_{100}$, —C(O)N$R_{100}$$R_{101}$, —N($R_{100}$)C(O)$R_{101}$, —S(O)$_2$$R_{100}$, —S(O)$R_{100}$, —S$R_{100}$, —S(O)$_2$N($R_{100}$)$R_{101}$, —CF$_3$, —CN, —NO$_2$, —N$_3$.

In a preferred embodiment, the invention relates to a compound wherein $R_8$ is $C_1$-$C_4$ alkyl.

In a preferred embodiment, the invention relates to a compound wherein $R_9$ is H, alkyl, alkoxy or halogen.

In a preferred embodiment, the invention relates to a compound, wherein $A_3$ is H and $Cy_1$ is absent.

In a preferred embodiment, the invention relates to a compound having the formula:

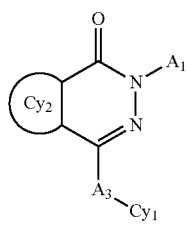

In a preferred embodiment, the invention relates to a compound wherein $A_1$ is carbocycle, substituted carbocycle, heterocycle, substituted heterocycle, aromatic, substituted aromatic, heteroaromatic, substituted heteroaromatic.

In a preferred embodiment, the invention relates to a compound having the formula:

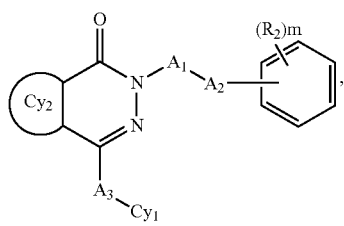

wherein m is 0, 1, 2, 3, 4 or 5; and
each $R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$;
alternatively two $R_2$ together with the atoms to which they are attached may form an optionally substituted 3, 4, 5, 6 or 7 membered ring, preferably a cycloalkyl, substituted cycloalkyl, heterocycle, substituted heterocycle, aryl, substituted aryl, heteroaryl or substituted heteroaryl group.

In a preferred embodiment, the invention relates to a compound having the formula:

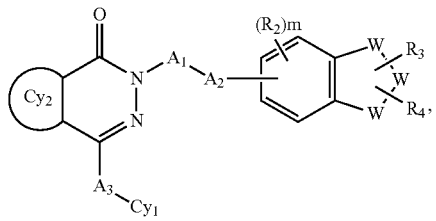

wherein each W is independently CH, $CR_{100}$, C(O), N, $NR_{100}$, O, S, SO, or $SO_2$;
each $R_3$ and $R_4$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, or —$OR_{100}$, —$SR_{100}$, —$NR_{100}R_{101}$, —$C(O)R_{100}$, —$C(O)OR_{100}$, —$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$, —$CF_3$, —CN, —$NO_2$, —$N_3$; and wherein represents a single or double bond.

In a preferred embodiment, the invention relates to a compound wherein $A_1$ is $C(R_{100})(R_{101})$ and $A_2$ is —C(O)N($R_{100}$)—.

In a preferred embodiment, the invention relates to a compound wherein $A_3$ is absent, —$[C(R_{100})(R_{101})]_n$—, —C(O)—, —$C(O)N(R_{100})$_or —$C(O)N(R_{100})(R_{101})$.

In a preferred embodiment, the invention relates to a compound wherein Cy1 is selected from:

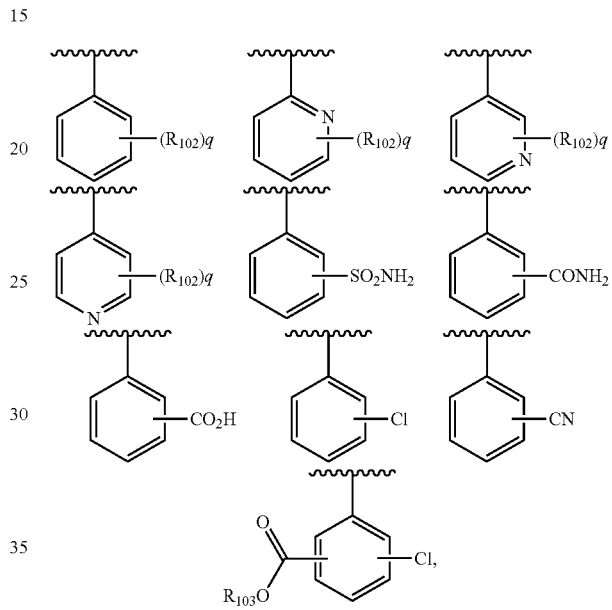

wherein q is 0, 1, 2, 3, 4 or 5; each $R_{102}$ is hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —$OR_{100}$, —$SR_{100}$, —$NR_{100}R_{101}$, —$C(O)R_{100}$, —$C(O)OR_{100}$,
—$C(O)NR_{100}R_{101}$, —$N(R_{100})C(O)R_{101}$, —$S(O)_2R_{100}$, —$S(O)R_{100}$, —$SR_{100}$, —$S(O)_2N(R_{100})R_{101}$—$CF_3$, —CN, —$NO_2$, —$N_3$; alternatively two of $R_{102}$ groups together with the atoms to which they are attached and any intervening atoms may form an additional optionally substituted 3, 4, 5, 6 or 7 membered ring; and $R_{103}$ is hydrogen, deuterium, alkyl, substituted alkyl, alkenyl, substituted alkenyl, alkynyl, substituted alkynyl, aliphatic, substituted aliphatic, aryl and substituted aryl.

In a preferred embodiment, the invention relates to a compound wherein Cy2 is selected from:

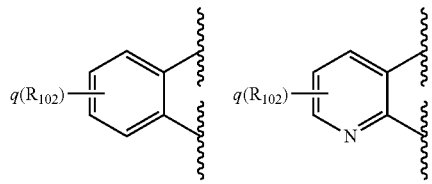

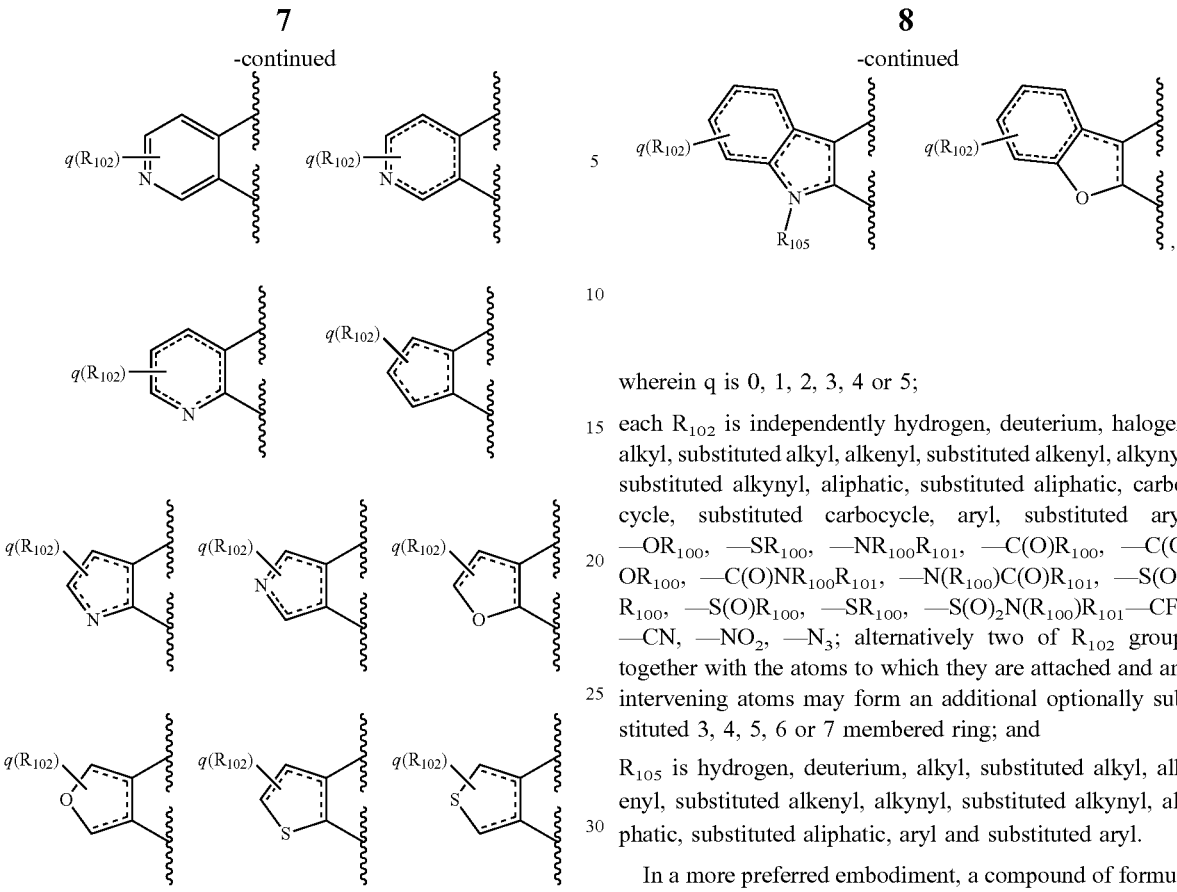

wherein q is 0, 1, 2, 3, 4 or 5;

each $R_{102}$ is independently hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, $-OR_{100}$, $-SR_{100}$, $-NR_{100}R_{101}$, $-C(O)R_{100}$, $-C(O)OR_{100}$, $-C(O)NR_{100}R_{101}$, $-N(R_{100})C(O)R_{101}$, $-S(O)_2R_{100}$, $-S(O)R_{100}$, $-SR_{100}$, $-S(O)_2N(R_{100})R_{101}$ $-CF_3$, $-CN$, $-NO_2$, $-N_3$; alternatively two of $R_{102}$ groups together with the atoms to which they are attached and any intervening atoms may form an additional optionally substituted 3, 4, 5, 6 or 7 membered ring; and $R_{105}$ is hydrogen, deuterium, alkyl, substituted alkyl, alkenyl, substituted alkenyl, alkynyl, substituted alkynyl, aliphatic, substituted aliphatic, aryl and substituted aryl.

In a more preferred embodiment, a compound of formula I is selected from Table A:

TABLE A

| Example No. | Structure |
|---|---|
| 1. | 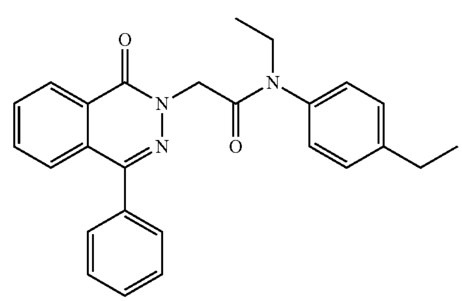 |
| 2. | 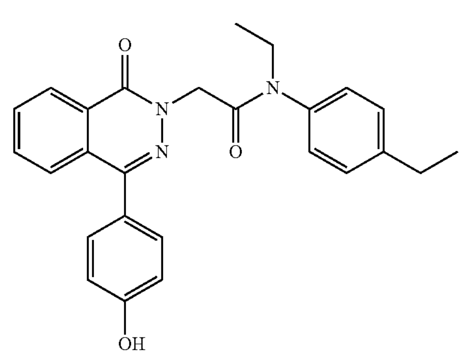 [SMILES: CCc1ccc(N(CC)C(=O)Cn2nc(-c3ccc(O)cc3)c3ccccc3c2=O)cc1] |

TABLE A-continued

| Example No. | Structure |
|---|---|
| 3. | (phthalazinone with 3-pyridyl substituent, N-ethyl-N-(4-ethylphenyl)acetamide) |
| 4. | (phthalazinone with 4-pyridyl substituent, N-ethyl-N-(4-ethylphenyl)acetamide) |
| 5. | (phthalazinone with quinolin-5-yl substituent, N-ethyl-N-(4-ethylphenyl)acetamide) |
| 6. | (phthalazinone with isoquinolin-5-yl substituent, N-ethyl-N-(4-ethylphenyl)acetamide) |
| 7. | (phthalazinone with pyrimidin-5-yl substituent, N-ethyl-N-(4-ethylphenyl)acetamide) |

TABLE A-continued

| Example No. | Structure |
|---|---|
| 8. | 4-(3-aminophenyl)-2-[2-(N-ethyl-4-ethylanilino)-2-oxoethyl]phthalazin-1(2H)-one |
| 9. | 4-(3-hydroxyphenyl)-2-[2-(N-ethyl-4-ethylanilino)-2-oxoethyl]phthalazin-1(2H)-one |
| 10. | 4-(1,3-benzodioxol-4-yl)-2-[2-(N-ethyl-4-ethylanilino)-2-oxoethyl]phthalazin-1(2H)-one |
| 11. | 3-{2-[2-(N-ethyl-4-ethylanilino)-2-oxoethyl]-1-oxo-1,2-dihydrophthalazin-4-yl}benzamide |
| 12. | 4-{2-[2-(N-ethyl-4-ethylanilino)-2-oxoethyl]-1-oxo-1,2-dihydrophthalazin-4-yl}benzamide |

TABLE A-continued
| Example No. | Structure |
|---|---|
| 13. | 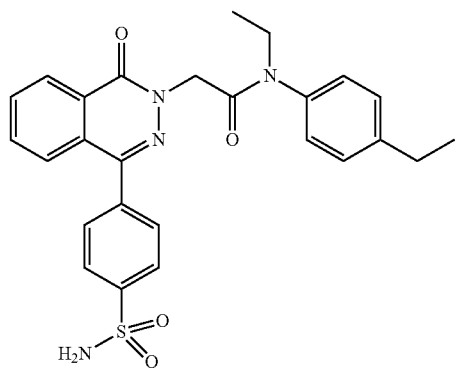 [SMILES: CCc1ccc(N(CC)C(=O)Cn2nc(-c3ccc(S(N)(=O)=O)cc3)c3ccccc3c2=O)cc1] |
| 14. | 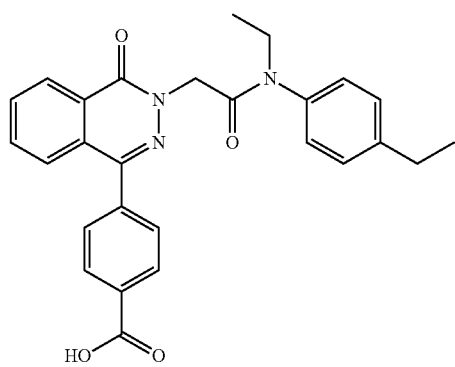 [SMILES: CCc1ccc(N(CC)C(=O)Cn2nc(-c3ccc(C(=O)O)cc3)c3ccccc3c2=O)cc1] |
| 15. | 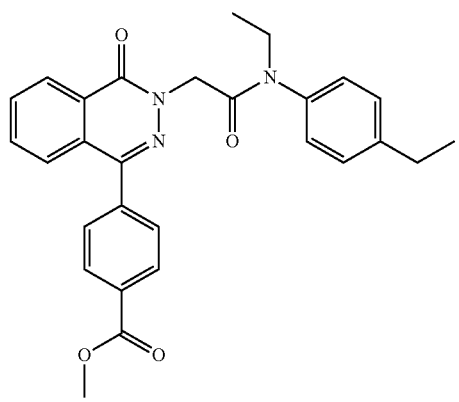 [SMILES: CCc1ccc(N(CC)C(=O)Cn2nc(-c3ccc(C(=O)OC)cc3)c3ccccc3c2=O)cc1] |
| 16. | 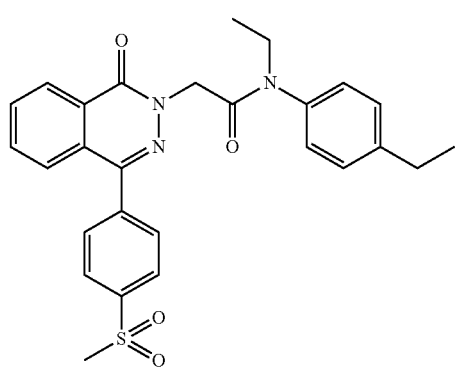 [SMILES: CCc1ccc(N(CC)C(=O)Cn2nc(-c3ccc(S(C)(=O)=O)cc3)c3ccccc3c2=O)cc1] |

TABLE A-continued
| Example No. | Structure |
|---|---|
| 17. | 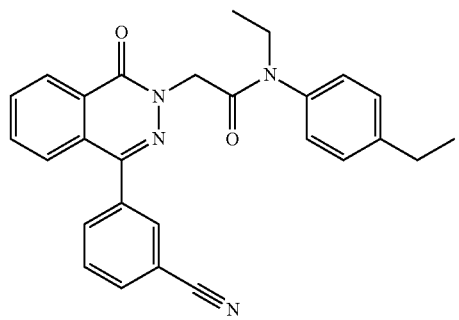 [SMILES: CCc1ccc(N(CC)C(=O)Cn2nc(-c3cccc(C#N)c3)c3ccccc3c2=O)cc1] |
| 18. | 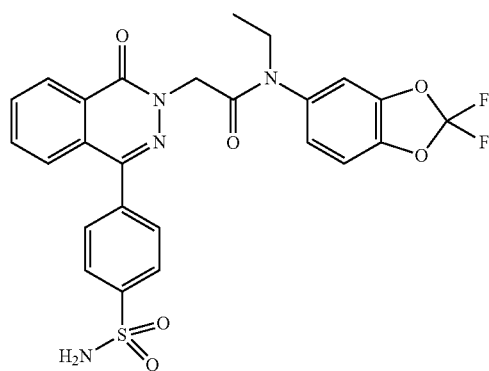 [SMILES: CCN(C(=O)Cn1nc(-c2ccc(S(N)(=O)=O)cc2)c2ccccc2c1=O)c1ccc2c(c1)OC(F)(F)O2] |
| 19. | 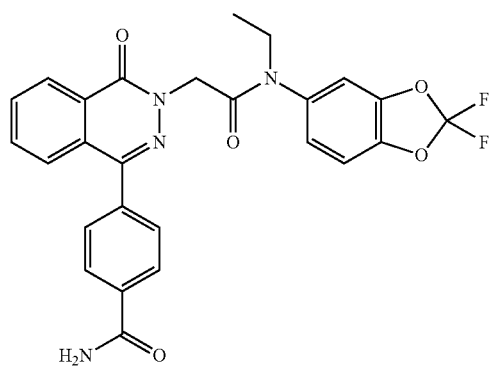 [SMILES: CCN(C(=O)Cn1nc(-c2ccc(C(N)=O)cc2)c2ccccc2c1=O)c1ccc2c(c1)OC(F)(F)O2] |
| 20. | 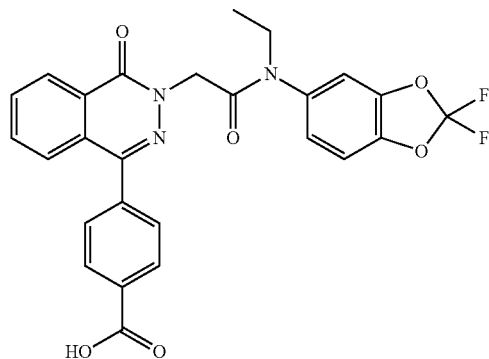 [SMILES: CCN(C(=O)Cn1nc(-c2ccc(C(=O)O)cc2)c2ccccc2c1=O)c1ccc2c(c1)OC(F)(F)O2] |

TABLE A-continued
| Example No. | Structure |
|---|---|
| 21. | 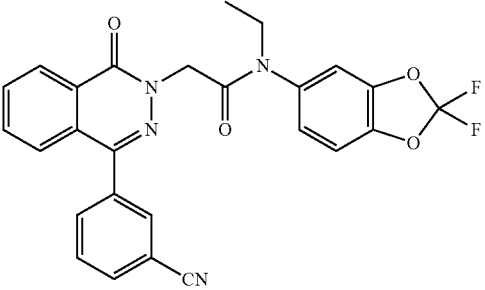 |
| 22. | 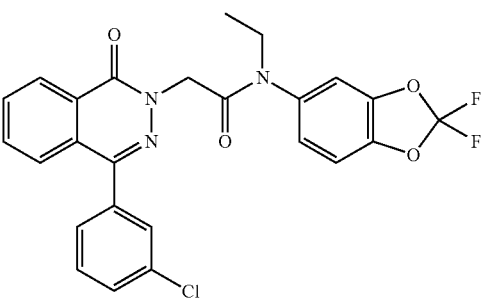 [SMILES: CCN(C(=O)Cn1nc(-c2cccc(Cl)c2)c2ccccc2c1=O)c1ccc2c(c1)OC(F)(F)O2] |
| 23. | 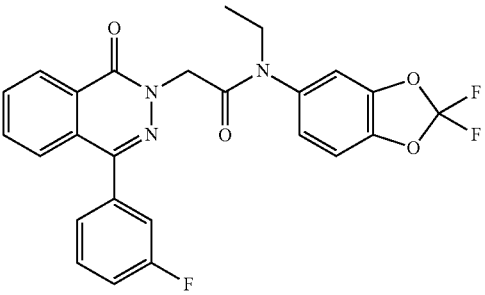 |
| 24. | 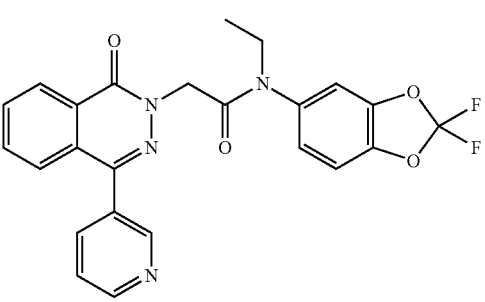 [SMILES: CCN(C(=O)Cn1nc(-c2cccnc2)c2ccccc2c1=O)c1ccc2c(c1)OC(F)(F)O2] |
| 25. | 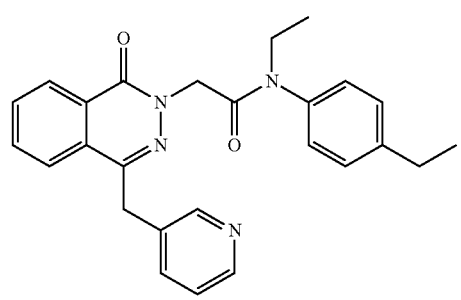 [SMILES: CCc1ccc(N(CC)C(=O)Cn2nc(Cc3cccnc3)c3ccccc3c2=O)cc1] |

TABLE A-continued
| Example No. | Structure |
|---|---|
| 26. | 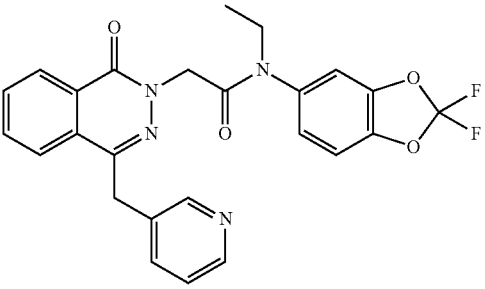 [SMILES: CCN(C(=O)Cn1nc(Cc2cccnc2)c2ccccc2c1=O)c1ccc2c(c1)OC(F)(F)O2] |
| 27. | 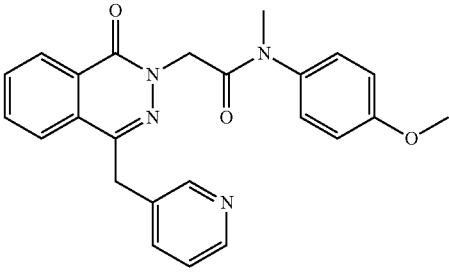 [SMILES: COc1ccc(N(C)C(=O)Cn2nc(Cc3cccnc3)c3ccccc3c2=O)cc1] |
| 28. | 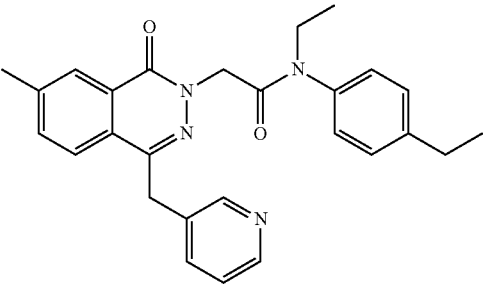 [SMILES: CCc1ccc(N(CC)C(=O)Cn2nc(Cc3cccnc3)c3ccc(C)cc3c2=O)cc1] |
| 29. | 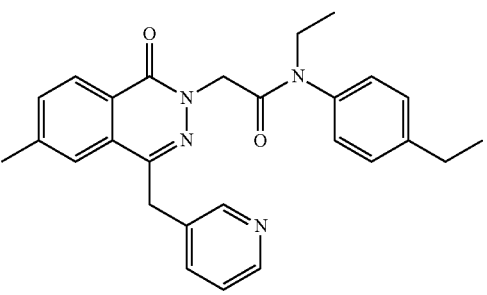 [SMILES: CCc1ccc(N(CC)C(=O)Cn2nc(Cc3cccnc3)c3cc(C)ccc3c2=O)cc1] |
| 30. | 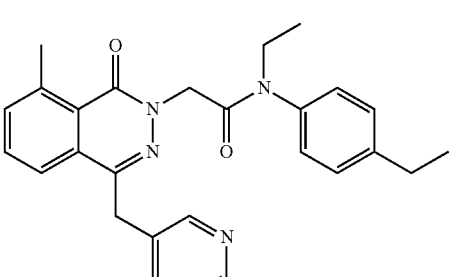 |

TABLE A-continued
| Example No. | Structure |
|---|---|
| 31. | 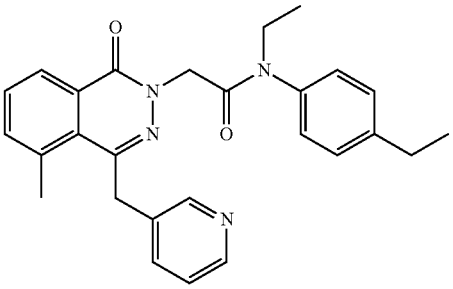 [SMILES: CCc1ccc(N(CC)C(=O)Cn2nc(Cc3cccnc3)c3c(C)cccc3c2=O)cc1] |
| 32. | 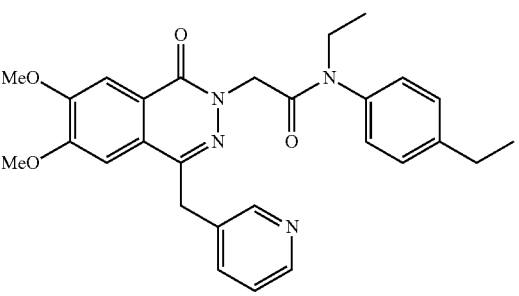 [SMILES: CCc1ccc(N(CC)C(=O)Cn2nc(Cc3cccnc3)c3cc(OC)c(OC)cc3c2=O)cc1] |
| 33. | 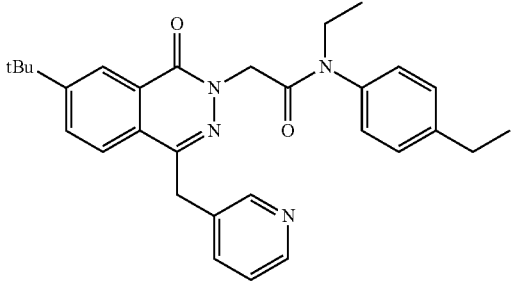 [SMILES: CCc1ccc(N(CC)C(=O)Cn2nc(Cc3cccnc3)c3ccc(C(C)(C)C)cc3c2=O)cc1] |
| 34. | 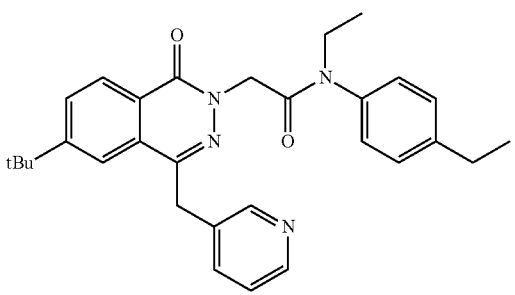 [SMILES: CCc1ccc(N(CC)C(=O)Cn2nc(Cc3cccnc3)c3cc(C(C)(C)C)ccc3c2=O)cc1] |
| 35. | 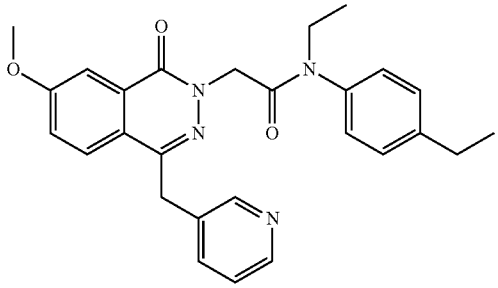 [SMILES: CCc1ccc(N(CC)C(=O)Cn2nc(Cc3cccnc3)c3ccc(OC)cc3c2=O)cc1] |

TABLE A-continued

| Example No. | Structure |
|---|---|
| 36. | (structure: 7-methoxy-4-(pyridin-3-ylmethyl)-phthalazin-1(2H)-one with N-ethyl-N-(4-ethylphenyl)acetamide substituent on N2) |
| 37. | (structure: 8-fluoro-4-(pyridin-3-ylmethyl)-phthalazin-1(2H)-one with N-ethyl-N-(4-ethylphenyl)acetamide substituent on N2) |
| 38. | (structure: 6,7-dichloro-4-(pyridin-3-ylmethyl)-phthalazin-1(2H)-one with N-ethyl-N-(4-ethylphenyl)acetamide substituent on N2) |
| 39. | (structure: 7-chloro-4-(pyridin-3-ylmethyl)-phthalazin-1(2H)-one with N-ethyl-N-(4-ethylphenyl)acetamide substituent on N2) |
| 40. | (structure: 6-chloro-4-(pyridin-3-ylmethyl)-phthalazin-1(2H)-one with N-ethyl-N-(4-ethylphenyl)acetamide substituent on N2) |

TABLE A-continued
| Example No. | Structure |
|---|---|
| 41. | 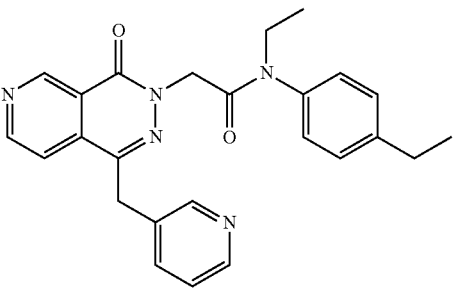 [SMILES: CCc1ccc(N(CC)C(=O)Cn2nc(Cc3cccnc3)c3ccncc3c2=O)cc1] |
| 42. | 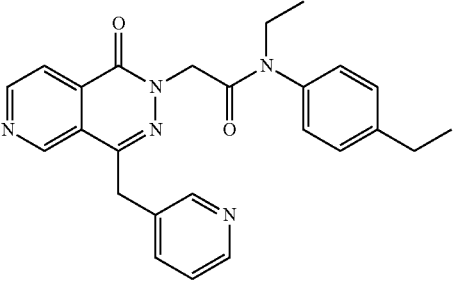 [SMILES: CCc1ccc(N(CC)C(=O)Cn2nc(Cc3cccnc3)c3cnccc3c2=O)cc1] |
| 43. | 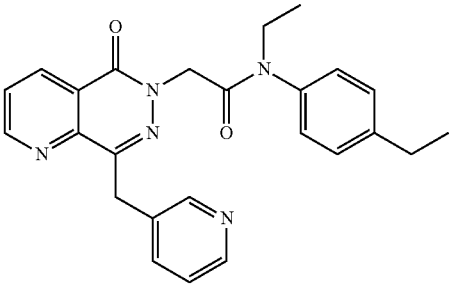 [SMILES: CCc1ccc(N(CC)C(=O)Cn2nc(Cc3cccnc3)c3ncccc3c2=O)cc1] |
| 44. | 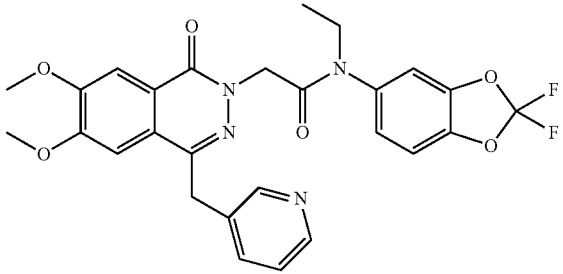 [SMILES: CCN(C(=O)Cn1nc(Cc2cccnc2)c2cc(OC)c(OC)cc2c1=O)c1ccc2c(c1)OC(F)(F)O2] |
| 45. | 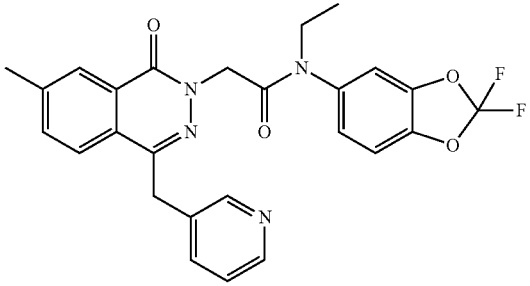 [SMILES: CCN(C(=O)Cn1nc(Cc2cccnc2)c2ccc(C)cc2c1=O)c1ccc2c(c1)OC(F)(F)O2] |

TABLE A-continued

| Example No. | Structure |
|---|---|
| 46. | (structure) |
| 47. | (structure) |
| 48. | (structure) |
| 49. | (structure) |
| 50. | (structure) |

TABLE A-continued

| Example No. | Structure |
|---|---|
| 51. | (structure) |
| 52. | (structure) |
| 53. | (structure) |
| 54. | (structure) |
| 55. | (structure) |

TABLE A-continued

| Example No. | Structure |
|---|---|
| 56. | 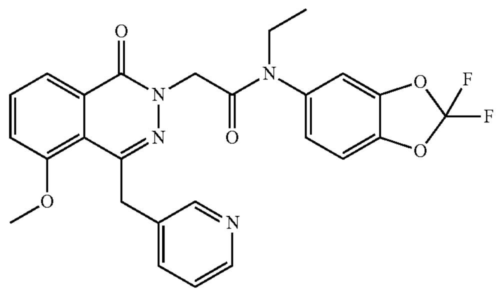 [SMILES: CCN(C(=O)Cn1nc(Cc2cccnc2)c2c(OC)cccc2c1=O)c1ccc2c(c1)OC(F)(F)O2] |
| 57. | 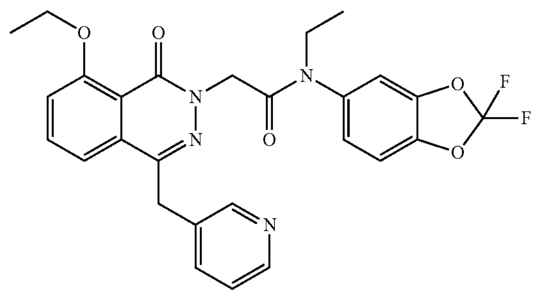 [SMILES: CCOc1cccc2c(Cc3cccnc3)nn(CC(=O)N(CC)c3ccc4c(c3)OC(F)(F)O4)c(=O)c12] |
| 58. | 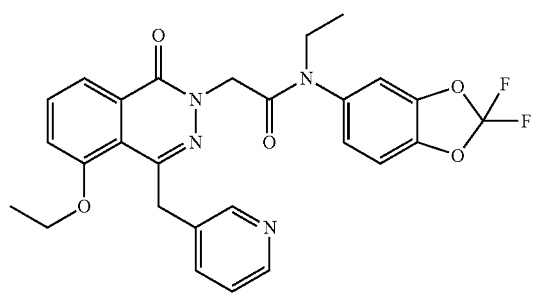 [SMILES: CCOc1cccc2c(=O)n(CC(=O)N(CC)c3ccc4c(c3)OC(F)(F)O4)nc(Cc3cccnc3)c12] |
| 59. | 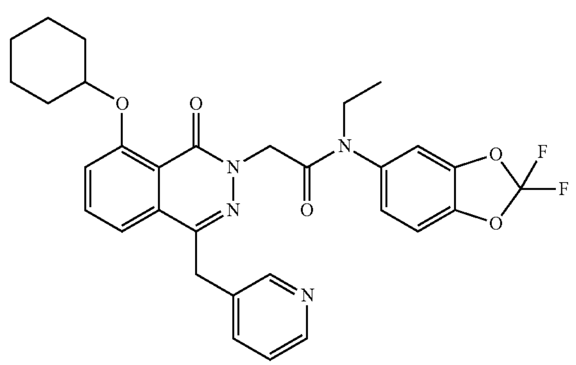 [SMILES: CCN(C(=O)Cn1nc(Cc2cccnc2)c2cccc(OC3CCCCC3)c2c1=O)c1ccc2c(c1)OC(F)(F)O2] |
| 60. | 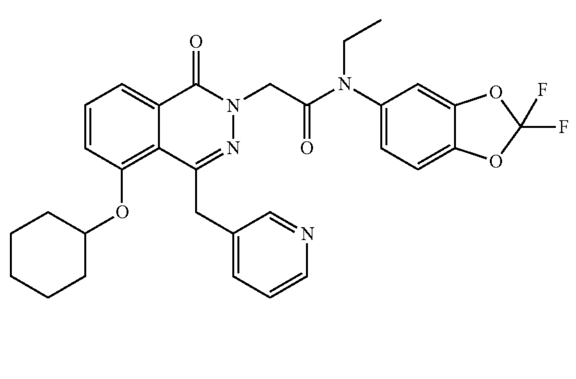 [SMILES: CCN(C(=O)Cn1nc(Cc2cccnc2)c2c(OC3CCCCC3)cccc2c1=O)c1ccc2c(c1)OC(F)(F)O2] |

TABLE A-continued
| Example No. | Structure |
|---|---|
| 61. | 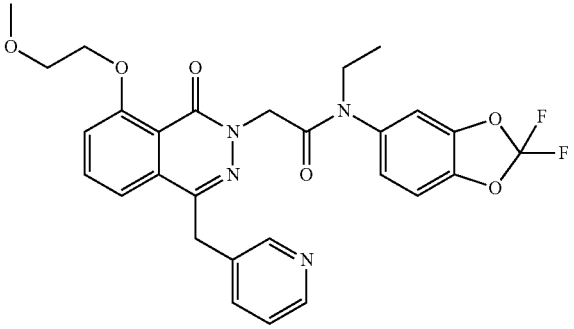 [SMILES: CCN(C(=O)Cn1nc(Cc2cccnc2)c2cccc(OCCOC)c2c1=O)c1ccc2c(c1)OC(F)(F)O2] |
| 62. | 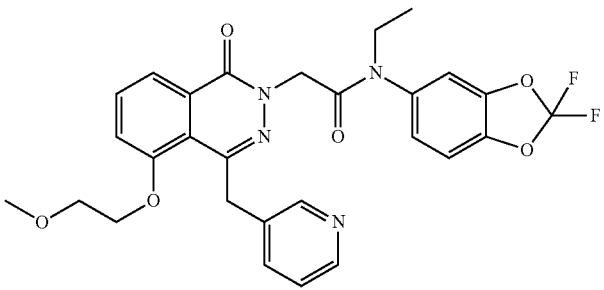 [SMILES: CCN(C(=O)Cn1nc(Cc2cccnc2)c2c(OCCOC)cccc2c1=O)c1ccc2c(c1)OC(F)(F)O2] |
| 63. | 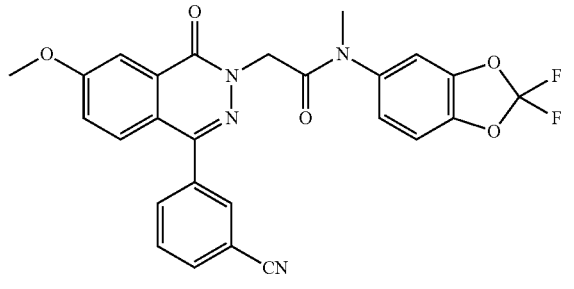 [SMILES: COc1ccc2c(-c3cccc(C#N)c3)nn(CC(=O)N(C)c3ccc4c(c3)OC(F)(F)O4)c(=O)c2c1] |
| 64. | 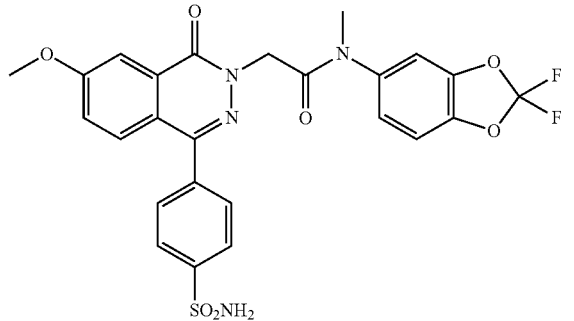 [SMILES: COc1ccc2c(-c3ccc(S(N)(=O)=O)cc3)nn(CC(=O)N(C)c3ccc4c(c3)OC(F)(F)O4)c(=O)c2c1] |
| 65. | 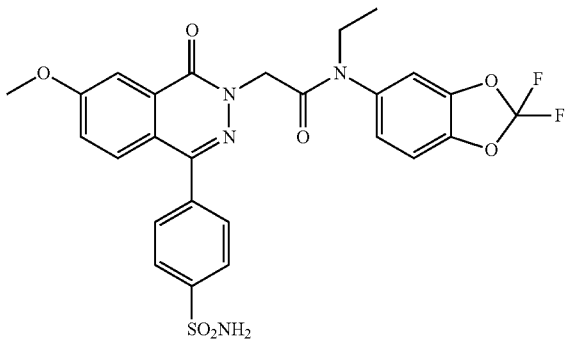 [SMILES: CCN(C(=O)Cn1nc(-c2ccc(S(N)(=O)=O)cc2)c2ccc(OC)cc2c1=O)c1ccc2c(c1)OC(F)(F)O2] |

TABLE A-continued

| Example No. | Structure |
|---|---|
| 66. | (structure) |
| 67. | (structure) |
| 68. | (structure) |
| 69. | (structure) |
| 70. | (structure) |

TABLE A-continued
| Example No. | Structure |
|---|---|
| 71. | 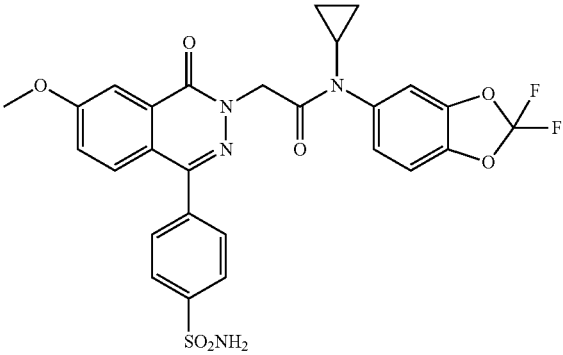 [SMILES: COc1ccc2c(-c3ccc(S(N)(=O)=O)cc3)nn(CC(=O)N(c3ccc4c(c3)OC(F)(F)O4)C3CC3)c(=O)c2c1] |
| 72. | 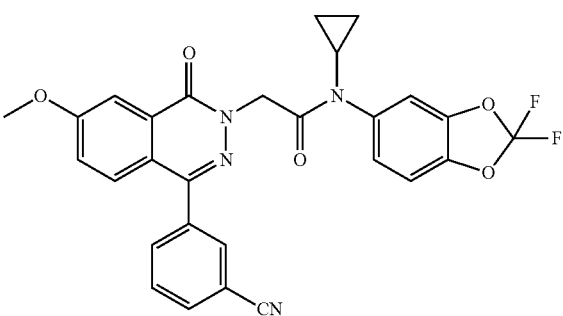 [SMILES: COc1ccc2c(-c3cccc(C#N)c3)nn(CC(=O)N(c3ccc4c(c3)OC(F)(F)O4)C3CC3)c(=O)c2c1] |
| 73. | 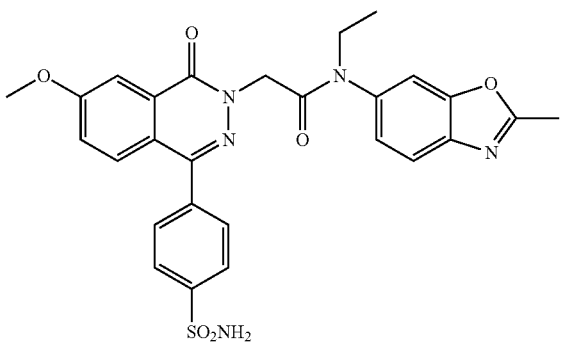 |
| 74. | 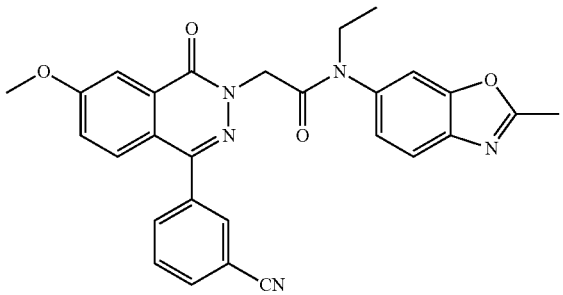 |

TABLE A-continued
| Example No. | Structure |
|---|---|
| 75. | 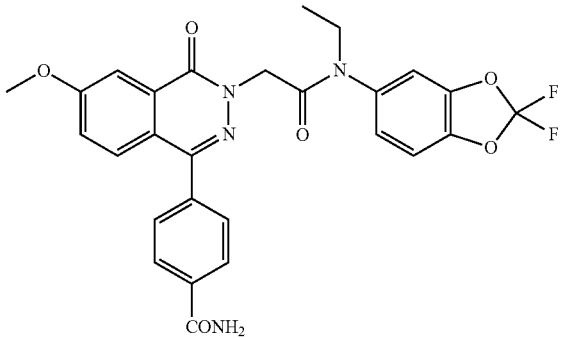 [SMILES: CCN(C(=O)Cn1nc(-c2ccc(C(N)=O)cc2)c2ccc(OC)cc2c1=O)c1ccc2c(c1)OC(F)(F)O2] |
| 76. | 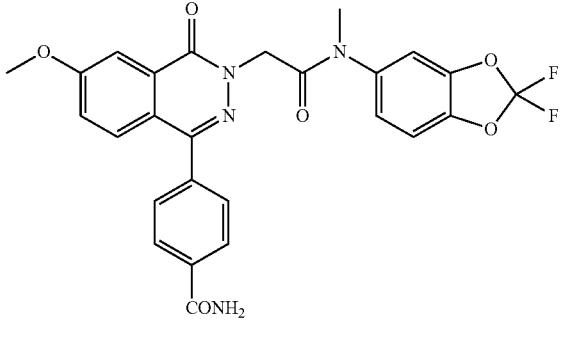 [SMILES: COc1ccc2c(-c3ccc(C(N)=O)cc3)nn(CC(=O)N(C)c3ccc4c(c3)OC(F)(F)O4)c(=O)c2c1] |
| 77. | 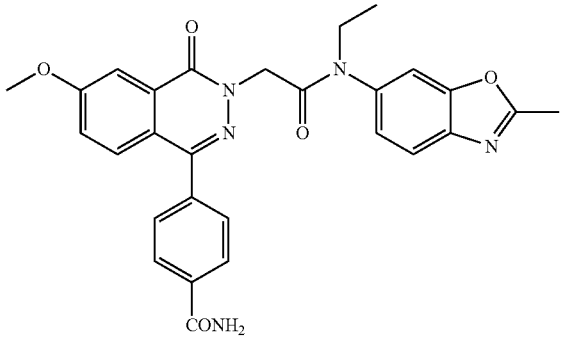 |
| 78. | 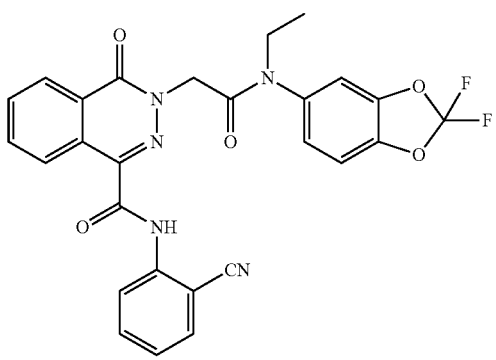 [SMILES: CCN(C(=O)Cn1nc(C(=O)Nc2ccccc2C#N)c2ccccc2c1=O)c1ccc2c(c1)OC(F)(F)O2] |

TABLE A-continued
| Example No. | Structure |
|---|---|
| 79. | 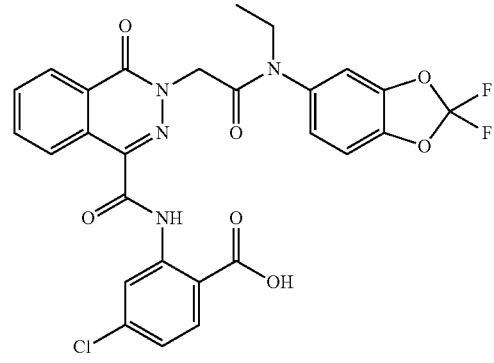 [SMILES: CCN(C(=O)Cn1nc(C(=O)Nc2cc(Cl)ccc2C(=O)O)c2ccccc2c1=O)c1ccc2c(c1)OC(F)(F)O2] |
| 80. | 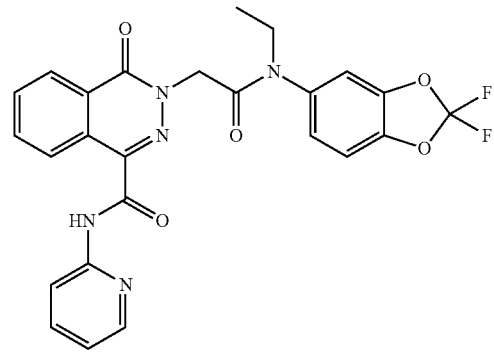 |
| 81. | 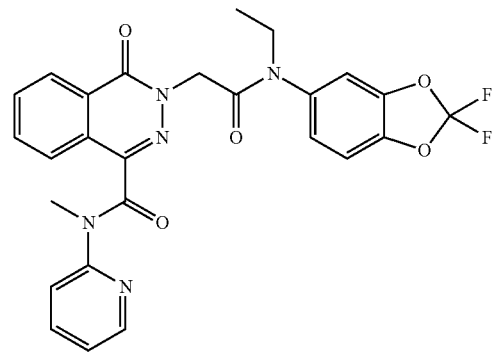 [SMILES: CCN(C(=O)Cn1nc(C(=O)N(C)c2ccccn2)c2ccccc2c1=O)c1ccc2c(c1)OC(F)(F)O2] |
| 82. | 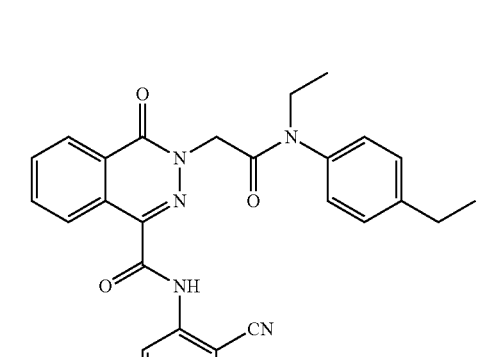 |

TABLE A-continued
| Example No. | Structure |
|---|---|
| 83. | 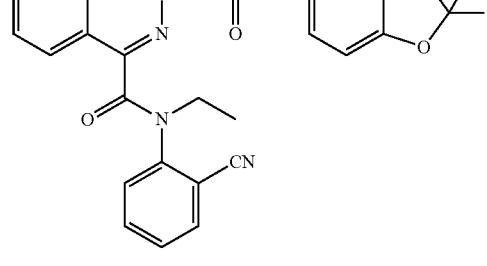 |
| 84. | 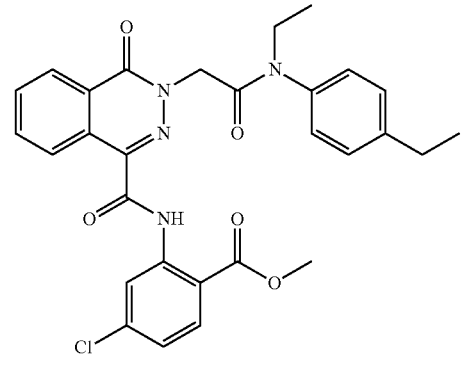 [SMILES: CCc1ccc(N(CC)C(=O)Cn2nc(C(=O)Nc3cc(Cl)ccc3C(=O)OC)c3ccccc3c2=O)cc1] |
| 85. | 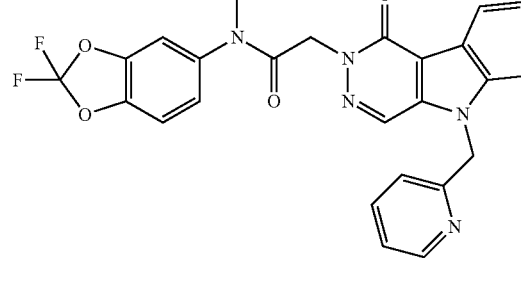 |
| 86. | 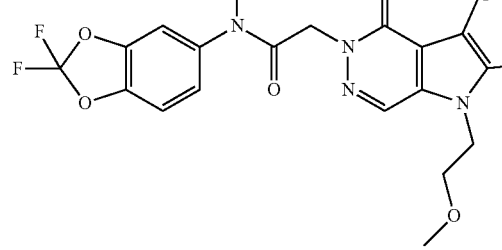 |

TABLE A-continued

| Example No. | Structure |
|---|---|
| 87. | 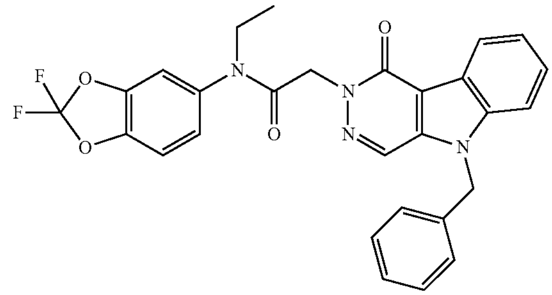 [SMILES: CCN(C(=O)Cn1ncc2c(c1=O)c1ccccc1n2Cc1ccccc1)c1ccc2c(c1)OC(F)(F)O2] |
| 88. | 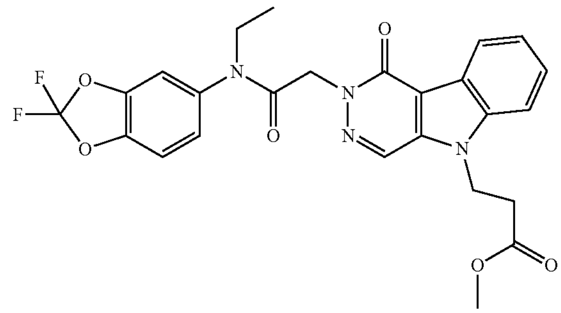 [SMILES: CCN(C(=O)Cn1ncc2c(c1=O)c1ccccc1n2CCC(=O)OC)c1ccc2c(c1)OC(F)(F)O2] |
| 89. | 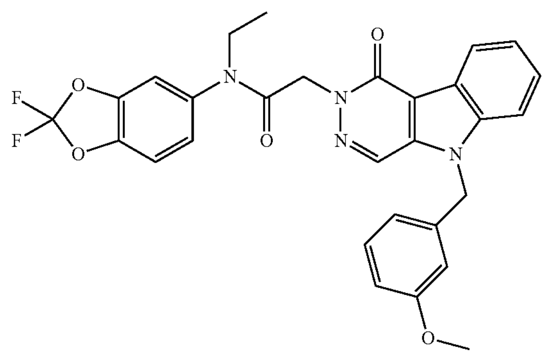 [SMILES: CCN(C(=O)Cn1ncc2c(c1=O)c1ccccc1n2Cc1cccc(OC)c1)c1ccc2c(c1)OC(F)(F)O2] |
| 90. | 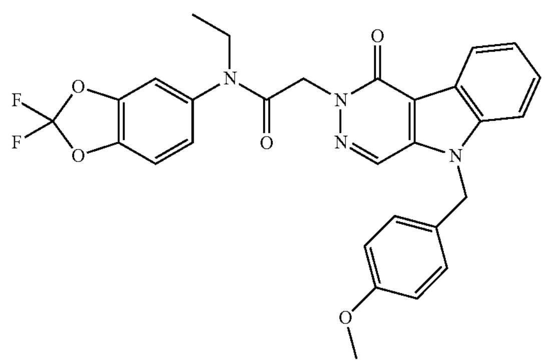 [SMILES: CCN(C(=O)Cn1ncc2c(c1=O)c1ccccc1n2Cc1ccc(OC)cc1)c1ccc2c(c1)OC(F)(F)O2] |
| 91. | 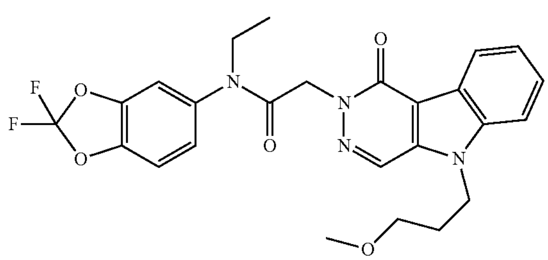 [SMILES: CCN(C(=O)Cn1ncc2c(c1=O)c1ccccc1n2CCCOC)c1ccc2c(c1)OC(F)(F)O2] |

TABLE A-continued
| Example No. | Structure |
|---|---|
| 92. | 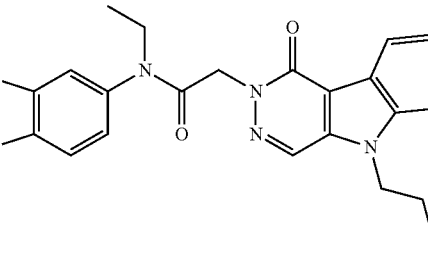 |
| 93. | 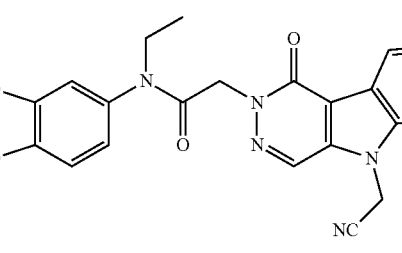 |
| 94. | 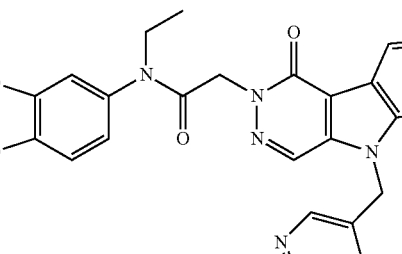 |
| 95. | 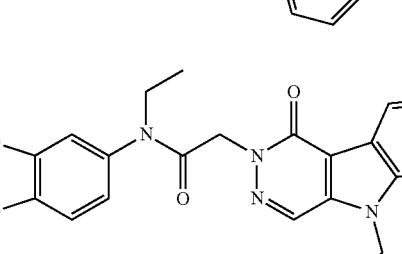 |
| 96. | 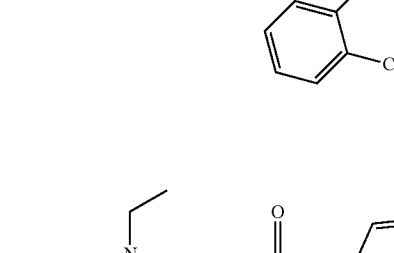 |

TABLE A-continued

| Example No. | Structure |
|---|---|
| 97. | (structure) |
| 98. | (structure) |
| 99. | (structure) |
| 100. | (structure) |
| 101. | (structure) |

TABLE A-continued
| Example No. | Structure |
| --- | --- |
| 102. | 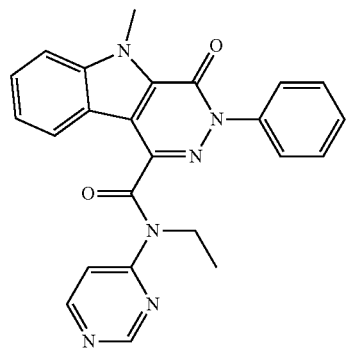 [SMILES: CCN(C(=O)c1nn(-c2ccccc2)c(=O)c2c1c1ccccc1n2C)c1ccncn1] |
| 103. | 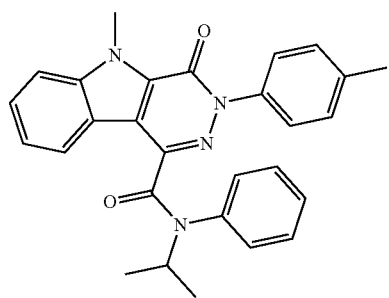 [SMILES: Cc1ccc(-n2nc(C(=O)N(c3ccccc3)C(C)C)c3c4ccccc4n(C)c3c2=O)cc1] |
| 104. | 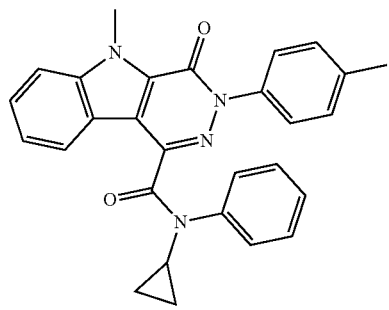 [SMILES: Cc1ccc(-n2nc(C(=O)N(c3ccccc3)C3CC3)c3c4ccccc4n(C)c3c2=O)cc1] |
| 105. | 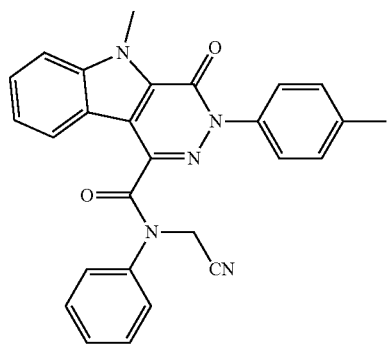 [SMILES: Cc1ccc(-n2nc(C(=O)N(CC#N)c3ccccc3)c3c4ccccc4n(C)c3c2=O)cc1] |

TABLE A-continued

| Example No. | Structure |
|---|---|
| 106. | 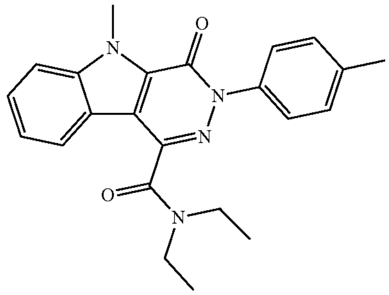 [SMILES: CCN(CC)C(=O)c1nn(-c2ccc(C)cc2)c(=O)c2c1c1ccccc1n2C] |
| 107. | 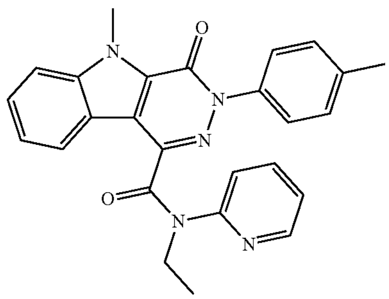 [SMILES: CCN(C(=O)c1nn(-c2ccc(C)cc2)c(=O)c2c1c1ccccc1n2C)c1ccccn1] |
| 108. | 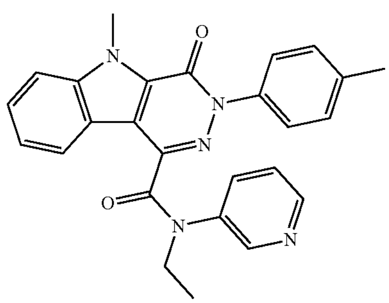 [SMILES: CCN(C(=O)c1nn(-c2ccc(C)cc2)c(=O)c2c1c1ccccc1n2C)c1cccnc1] |
| 109. | 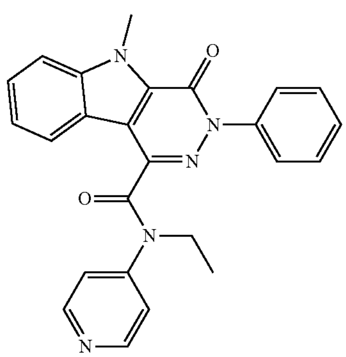 |
| 110. | 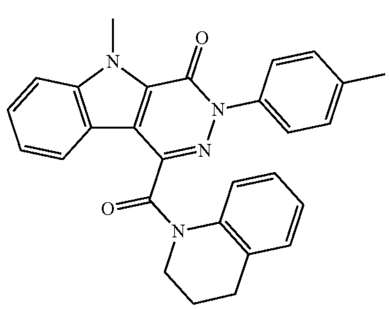 [SMILES: Cc1ccc(-n2nc(C(=O)N3CCCc4ccccc43)c3c4ccccc4n(C)c3c2=O)cc1] |

TABLE A-continued
| Example No. | Structure |
|---|---|
| 111. | 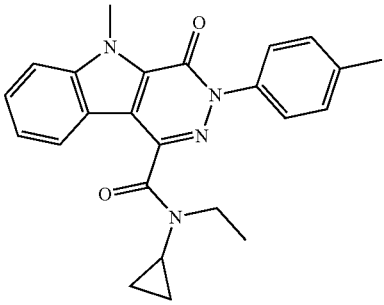 [SMILES: CCN(C(=O)c1nn(-c2ccc(C)cc2)c(=O)c2c1c1ccccc1n2C)C1CC1] |
| 112. | 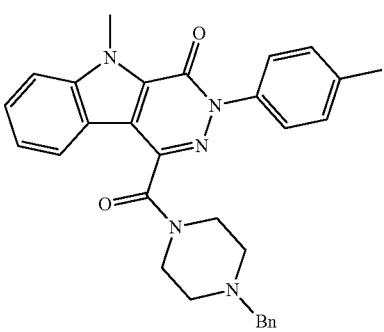 [SMILES: Cc1ccc(-n2nc(C(=O)N3CCN(Cc4ccccc4)CC3)c3c4ccccc4n(C)c3c2=O)cc1] |
| 113. | 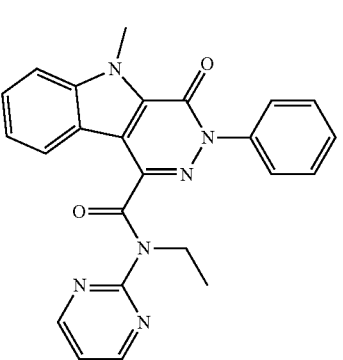 [SMILES: CCN(C(=O)c1nn(-c2ccccc2)c(=O)c2c1c1ccccc1n2C)c1ncccn1] |
| 114. | 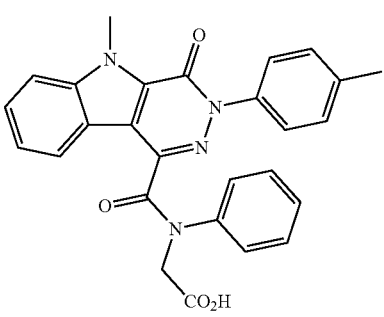 [SMILES: Cc1ccc(-n2nc(C(=O)N(CC(=O)O)c3ccccc3)c3c4ccccc4n(C)c3c2=O)cc1] |

TABLE A-continued
| Example No. | Structure |
|---|---|
| 115. | 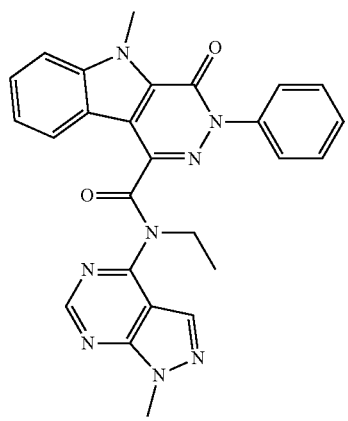 [SMILES: CCN(C(=O)c1nn(-c2ccccc2)c(=O)c2c1c1ccccc1n2C)c1ncnc2c1cnn2C] |
| 116. | 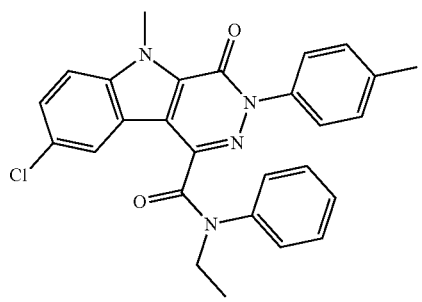 [SMILES: CCN(C(=O)c1nn(-c2ccc(C)cc2)c(=O)c2c1c1cc(Cl)ccc1n2C)c1ccccc1] |
| 117. | 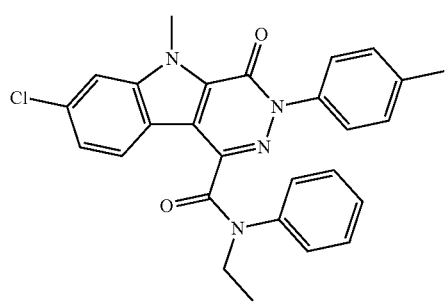 [SMILES: CCN(C(=O)c1nn(-c2ccc(C)cc2)c(=O)c2c1c1ccc(Cl)cc1n2C)c1ccccc1] |
| 118. | 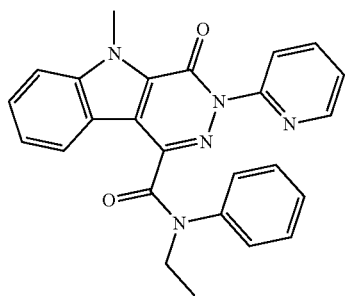 [SMILES: CCN(C(=O)c1nn(-c2ccccn2)c(=O)c2c1c1ccccc1n2C)c1ccccc1] |

TABLE A-continued
| Example No. | Structure |
|---|---|
| 119. | 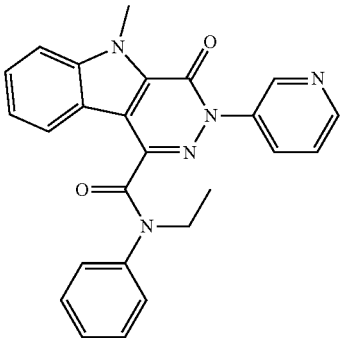 [SMILES: CCN(C(=O)c1nn(-c2cccnc2)c(=O)c2c1c1ccccc1n2C)c1ccccc1] |
| 120. | 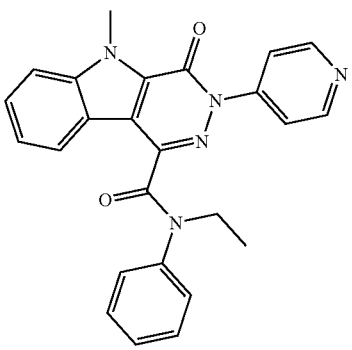 [SMILES: CCN(C(=O)c1nn(-c2ccncc2)c(=O)c2c1c1ccccc1n2C)c1ccccc1] |
| 121. | 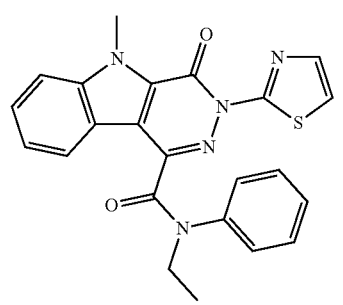 [SMILES: CCN(C(=O)c1nn(-c2nccs2)c(=O)c2c1c1ccccc1n2C)c1ccccc1] |
| 122. | 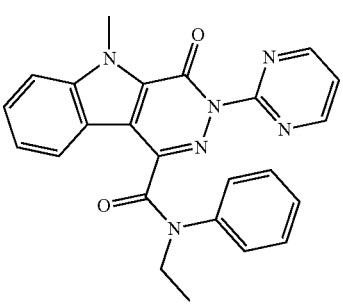 [SMILES: CCN(C(=O)c1nn(-c2ncccn2)c(=O)c2c1c1ccccc1n2C)c1ccccc1] |
| 123. | 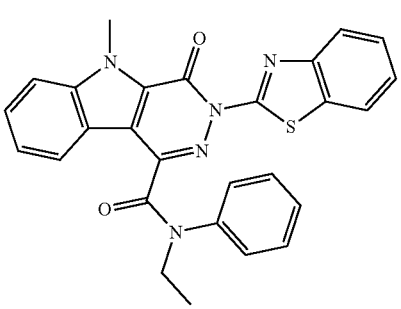 [SMILES: CCN(C(=O)c1nn(-c2nc3ccccc3s2)c(=O)c2c1c1ccccc1n2C)c1ccccc1] |

TABLE A-continued
| Example No. | Structure |
|---|---|
| 124. | 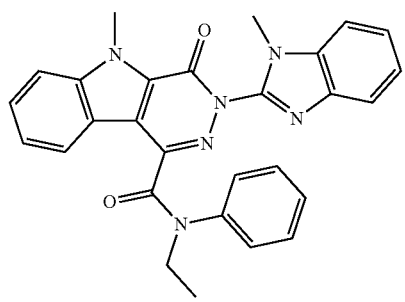 [SMILES: CCN(C(=O)c1nn(-c2nc3ccccc3n2C)c(=O)c2c1c1ccccc1n2C)c1ccccc1] |
| 125. | 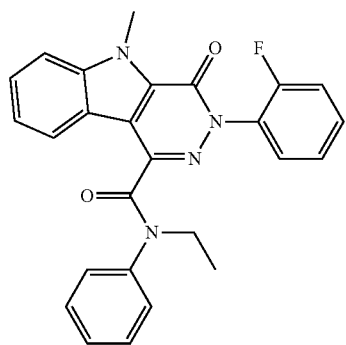 [SMILES: CCN(C(=O)c1nn(-c2ccccc2F)c(=O)c2c1c1ccccc1n2C)c1ccccc1] |
| 126. | 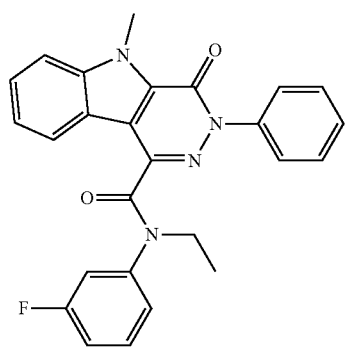 [SMILES: CCN(C(=O)c1nn(-c2ccccc2)c(=O)c2c1c1ccccc1n2C)c1cccc(F)c1] |
| 127. | 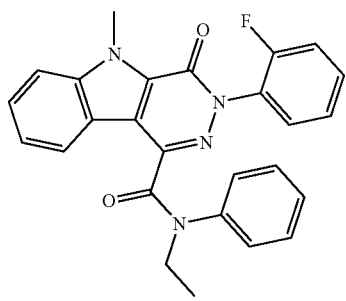 [SMILES: CCN(C(=O)c1nn(-c2ccccc2F)c(=O)c2c1c1ccccc1n2C)c1ccccc1] |

TABLE A-continued
| Example No. | Structure |
|---|---|
| 128. | 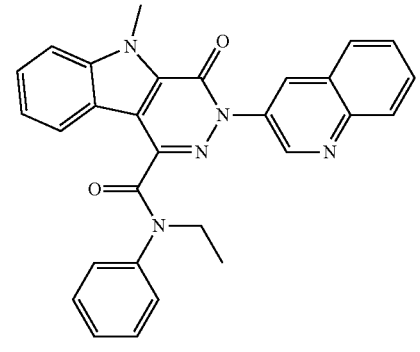 [SMILES: CCN(C(=O)c1nn(-c2cnc3ccccc3c2)c(=O)c2c1c1ccccc1n2C)c1ccccc1] |
| 129. | 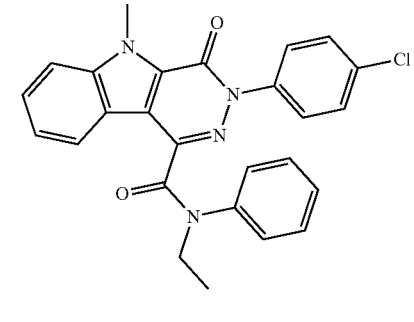 [SMILES: CCN(C(=O)c1nn(-c2ccc(Cl)cc2)c(=O)c2c1c1ccccc1n2C)c1ccccc1] |
| 130. | 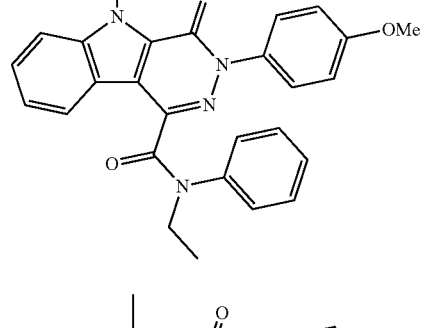 |
| 131. | 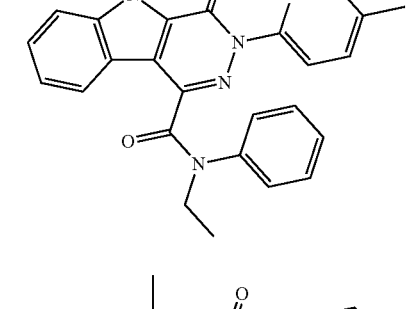 |
| 132. | 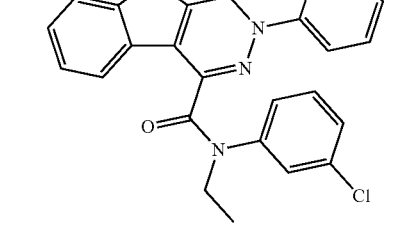 |

TABLE A-continued

| Example No. | Structure |
|---|---|
| 133. | 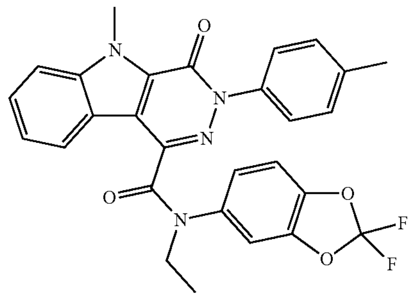 [SMILES: CCN(C(=O)c1nn(-c2ccc(C)cc2)c(=O)c2c1c1ccccc1n2C)c1ccc2c(c1)OC(F)(F)O2] |
| 134. | 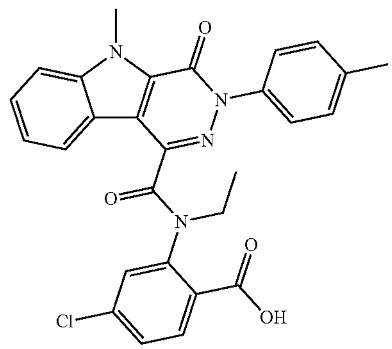 [SMILES: CCN(C(=O)c1nn(-c2ccc(C)cc2)c(=O)c2c1c1ccccc1n2C)c1cc(Cl)ccc1C(=O)O] |
| 135. | 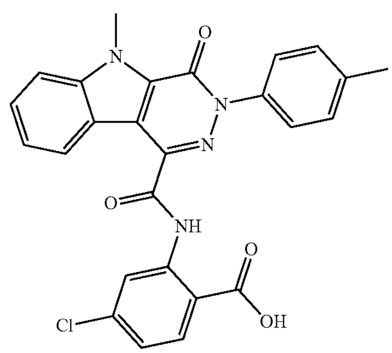 [SMILES: Cc1ccc(-n2nc(C(=O)Nc3cc(Cl)ccc3C(=O)O)c3c4ccccc4n(C)c3c2=O)cc1] |
| 136. | 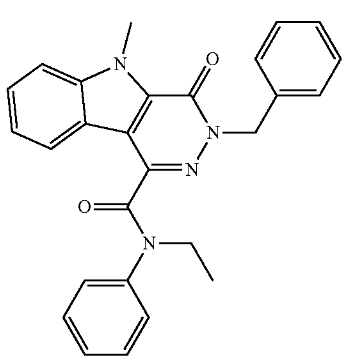 [SMILES: CCN(C(=O)c1nn(Cc2ccccc2)c(=O)c2c1c1ccccc1n2C)c1ccccc1] |

TABLE A-continued
| Example No. | Structure |
|---|---|
| 137. | 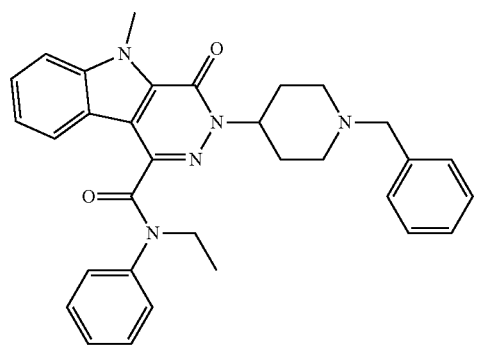 [SMILES: CCN(C(=O)c1nn(C2CCN(Cc3ccccc3)CC2)c(=O)c2c1c1ccccc1n2C)c1ccccc1] |
| 138. | 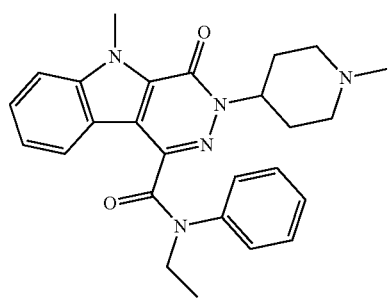 [SMILES: CCN(C(=O)c1nn(C2CCN(C)CC2)c(=O)c2c1c1ccccc1n2C)c1ccccc1] |
| 139. | 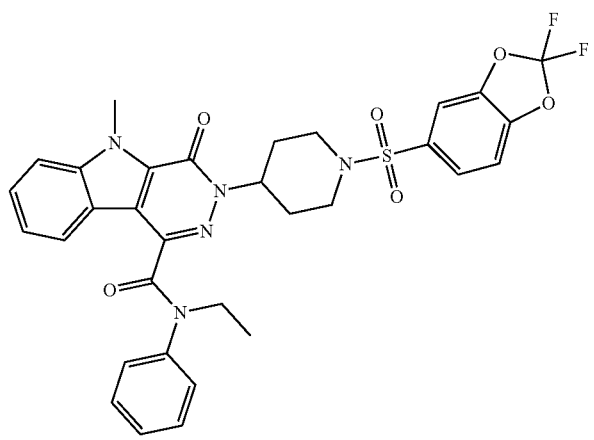 [SMILES: CCN(C(=O)c1nn(C2CCN(S(=O)(=O)c3ccc4c(c3)OC(F)(F)O4)CC2)c(=O)c2c1c1ccccc1n2C)c1ccccc1] |
| 140. | 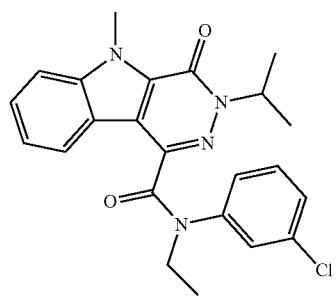 [SMILES: CCN(C(=O)c1nn(C(C)C)c(=O)c2c1c1ccccc1n2C)c1cccc(Cl)c1] |

TABLE A-continued
| Example No. | Structure |
|---|---|
| 141. | 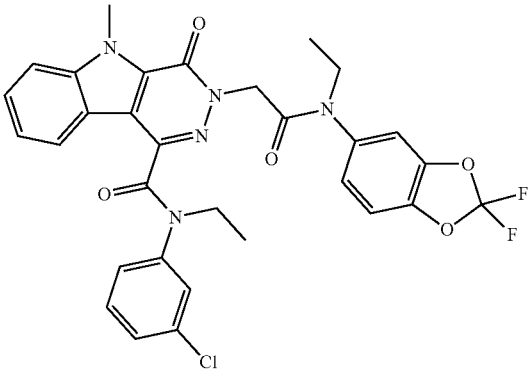 [SMILES: CCN(C(=O)Cn1nc(C(=O)N(CC)c2cccc(Cl)c2)c2c3ccccc3n(C)c2c1=O)c1ccc2c(c1)OC(F)(F)O2] |
| 142. | 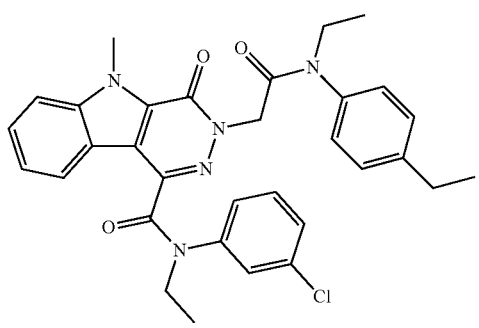 [SMILES: CCc1ccc(N(CC)C(=O)Cn2nc(C(=O)N(CC)c3cccc(Cl)c3)c3c4ccccc4n(C)c3c2=O)cc1] |
| 143. | 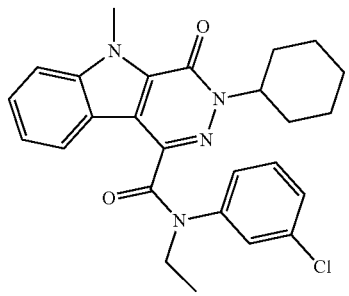 [SMILES: CCN(C(=O)c1nn(C2CCCCC2)c(=O)c2c1c1ccccc1n2C)c1cccc(Cl)c1] |
| 144. | 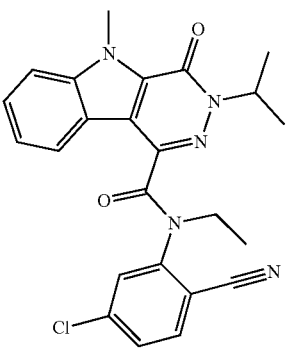 [SMILES: CCN(C(=O)c1nn(C(C)C)c(=O)c2c1c1ccccc1n2C)c1cc(Cl)ccc1C#N] |

TABLE A-continued

| Example No. | Structure |
|---|---|
| 145. | 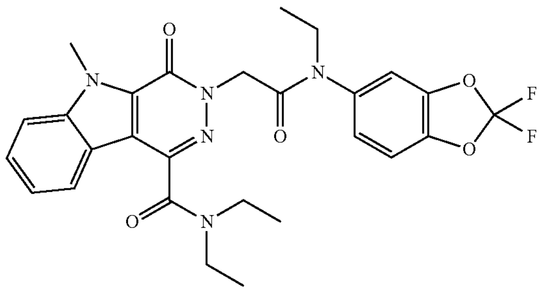 [SMILES: CCN(CC)C(=O)c1nn(CC(=O)N(CC)c2ccc3c(c2)OC(F)(F)O3)c(=O)c2c1c1ccccc1n2C] |
| 146. | 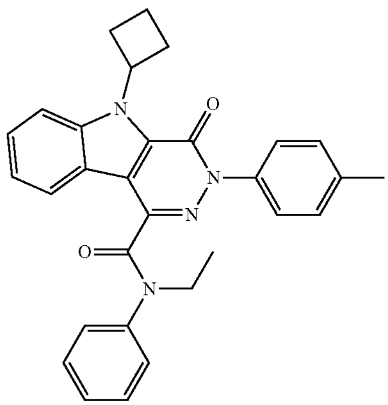 [SMILES: CCN(C(=O)c1nn(-c2ccc(C)cc2)c(=O)c2c1c1ccccc1n2C1CCC1)c1ccccc1] |
| 147. | 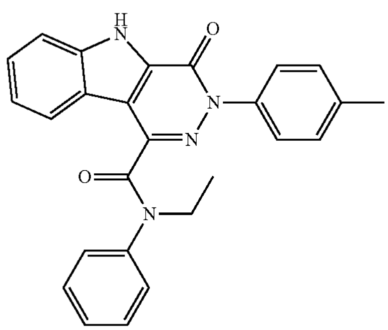 [SMILES: CCN(C(=O)c1nn(-c2ccc(C)cc2)c(=O)c2[nH]c3ccccc3c12)c1ccccc1] |
| 148. | 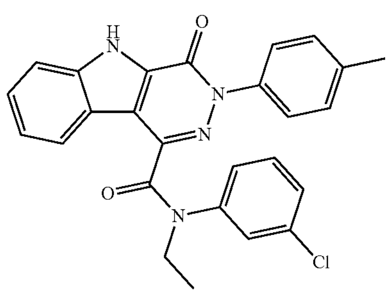 [SMILES: CCN(C(=O)c1nn(-c2ccc(C)cc2)c(=O)c2[nH]c3ccccc3c12)c1cccc(Cl)c1] |
| 149. | 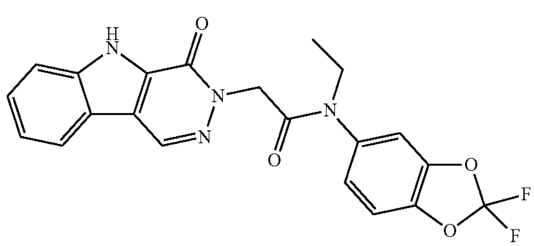 [SMILES: CCN(C(=O)Cn1ncc2c([nH]c3ccccc32)c1=O)c1ccc2c(c1)OC(F)(F)O2] |

TABLE A-continued
| Example No. | Structure |
|---|---|
| 150. | 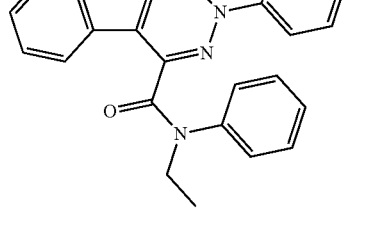 |
| 151. | 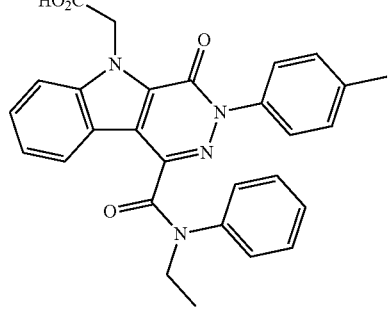 |
| 152. | 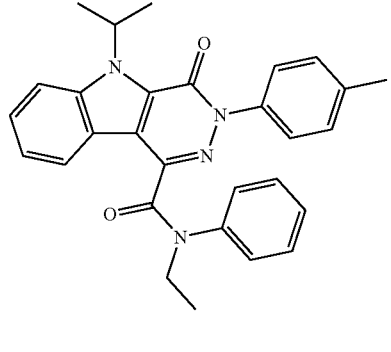 [SMILES: CCN(C(=O)c1nn(-c2ccc(C)cc2)c(=O)c2c1c1ccccc1n2C(C)C)c1ccccc1] |
| 153. | 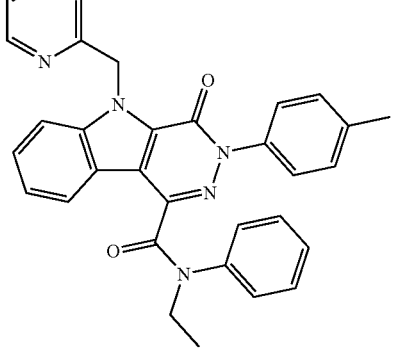 |

TABLE A-continued
| Example No. | Structure |
|---|---|
| 154. | 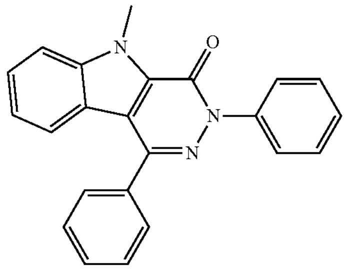 [SMILES: Cn1c2ccccc2c2c(-c3ccccc3)nn(-c3ccccc3)c(=O)c21] |
| 155. | 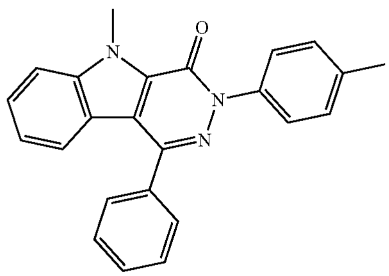 [SMILES: Cc1ccc(-n2nc(-c3ccccc3)c3c4ccccc4n(C)c3c2=O)cc1] |
| 156. | 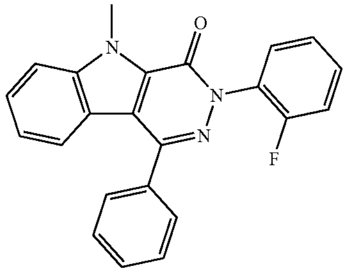 [SMILES: Cn1c2ccccc2c2c(-c3ccccc3)nn(-c3ccccc3F)c(=O)c21] |
| 157. | 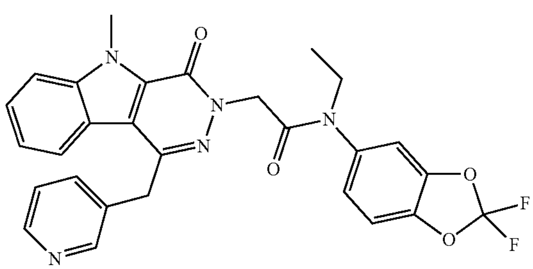 [SMILES: CCN(C(=O)Cn1nc(Cc2cccnc2)c2c3ccccc3n(C)c2c1=O)c1ccc2c(c1)OC(F)(F)O2] |
The compounds of this invention may be prepared by methods known in the art. Exemplary synthetic routes to prepare compounds of this invention are illustrated below: Schemes 1-10 illustrate processes for preparing compounds of formula I.
Scheme 1:
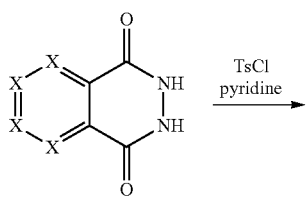
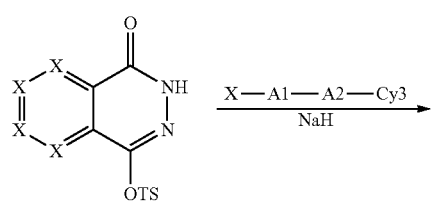
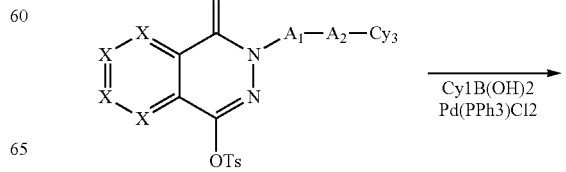

77
-continued
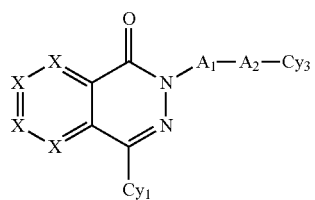
78
-continued
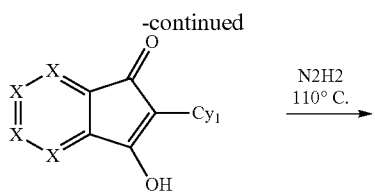
Scheme 2:
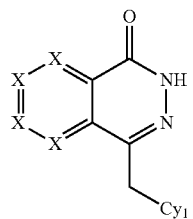
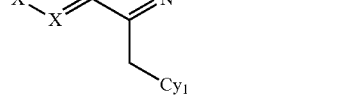
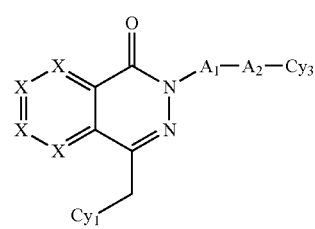
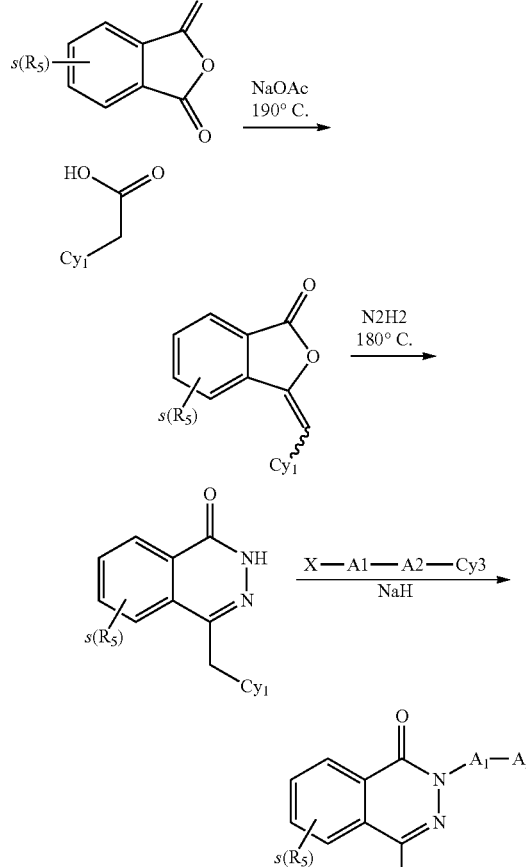
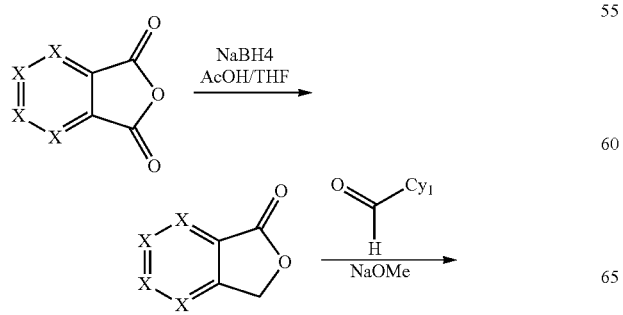
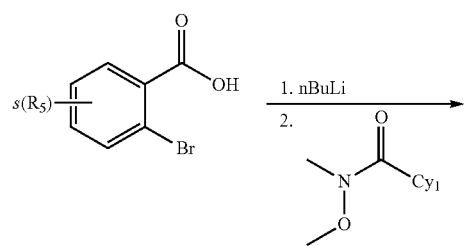
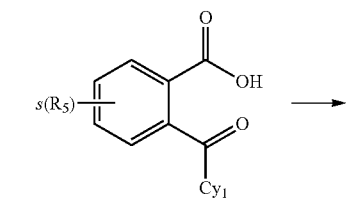
Scheme 3:
Scheme 4:
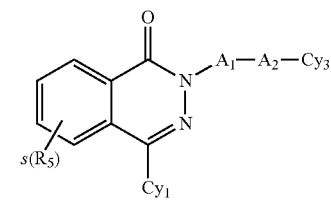

Scheme 5:
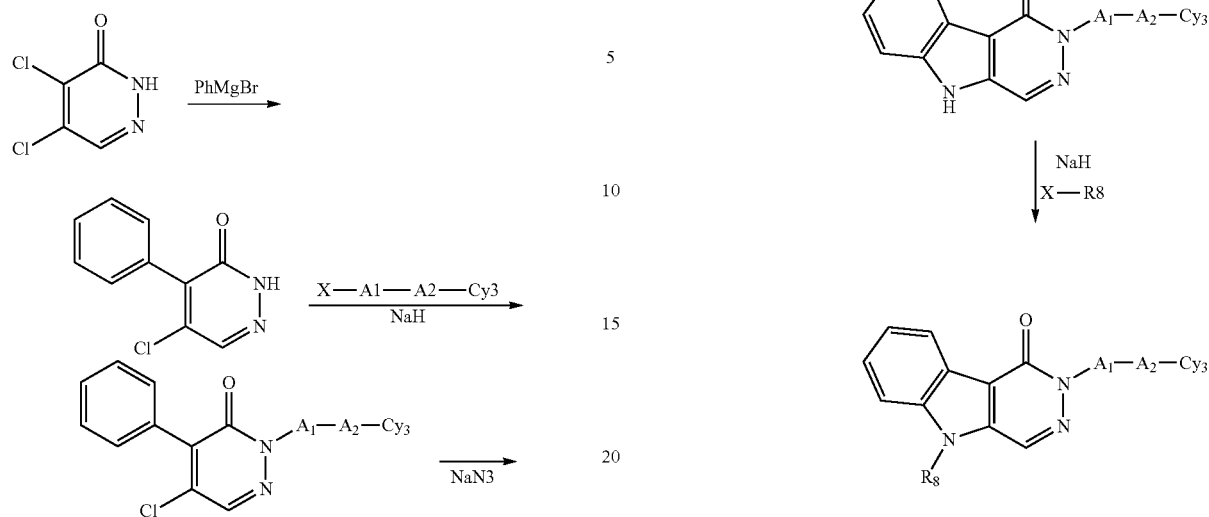
Scheme 6:
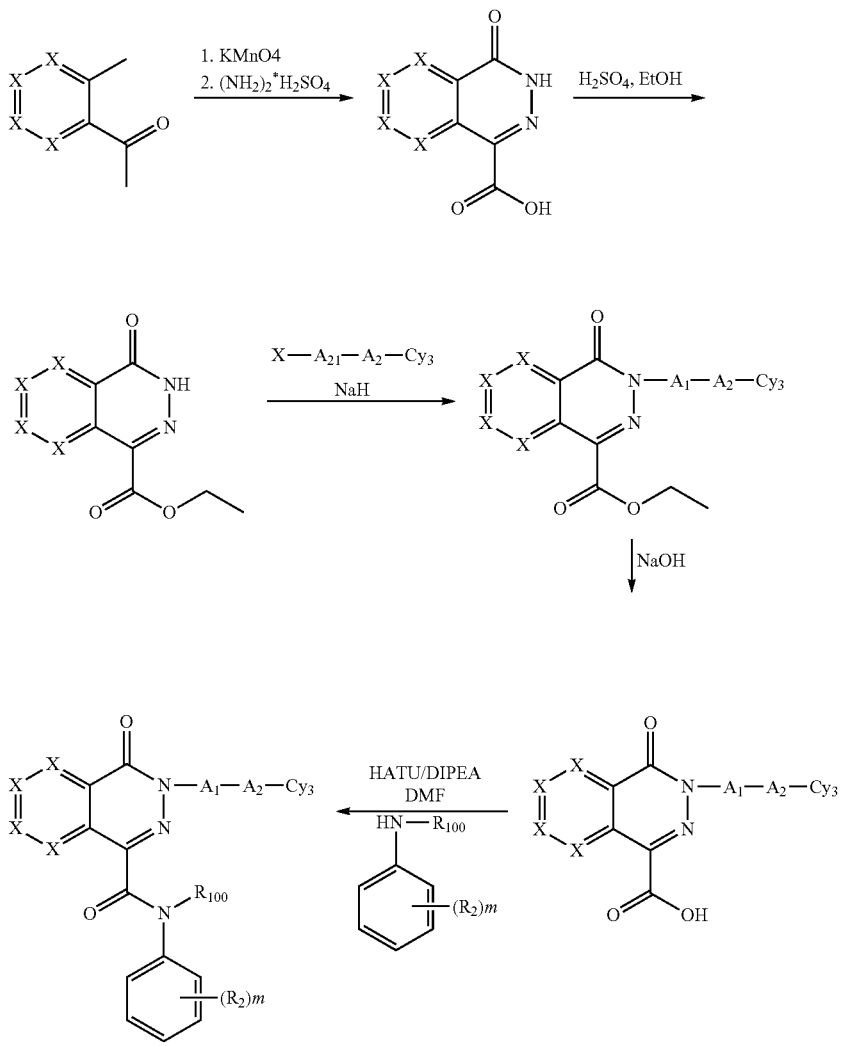

Scheme 7:
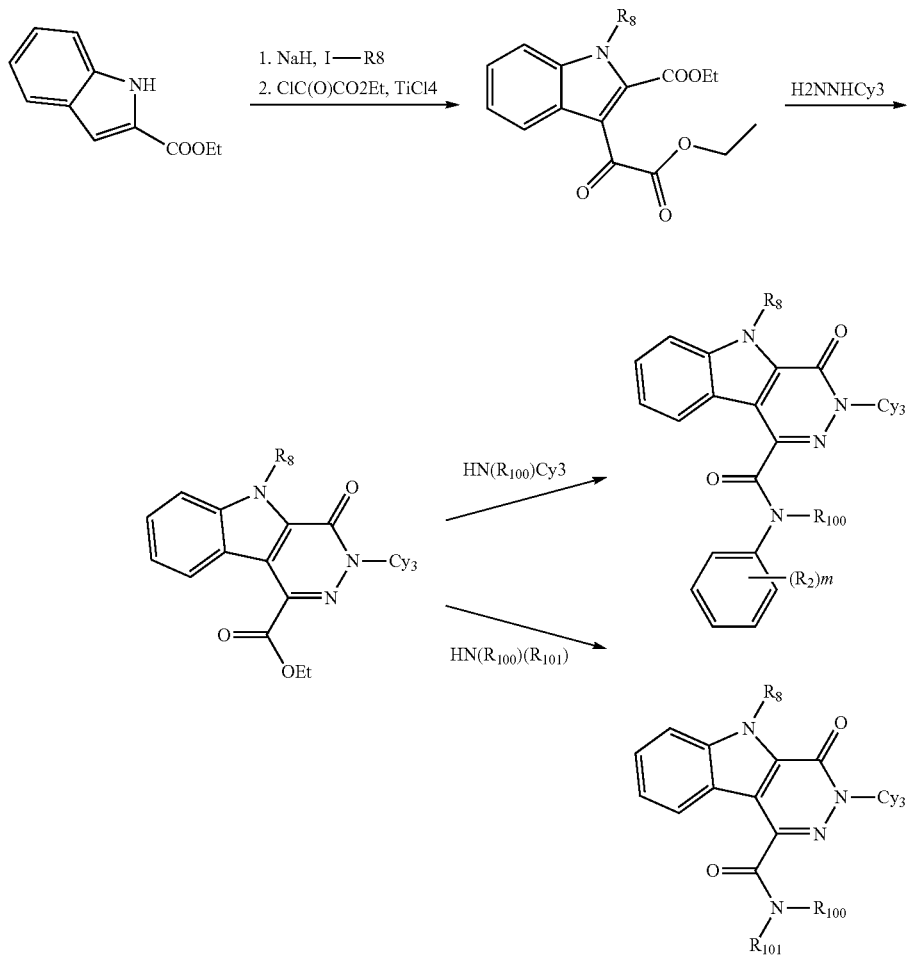
Scheme 8:
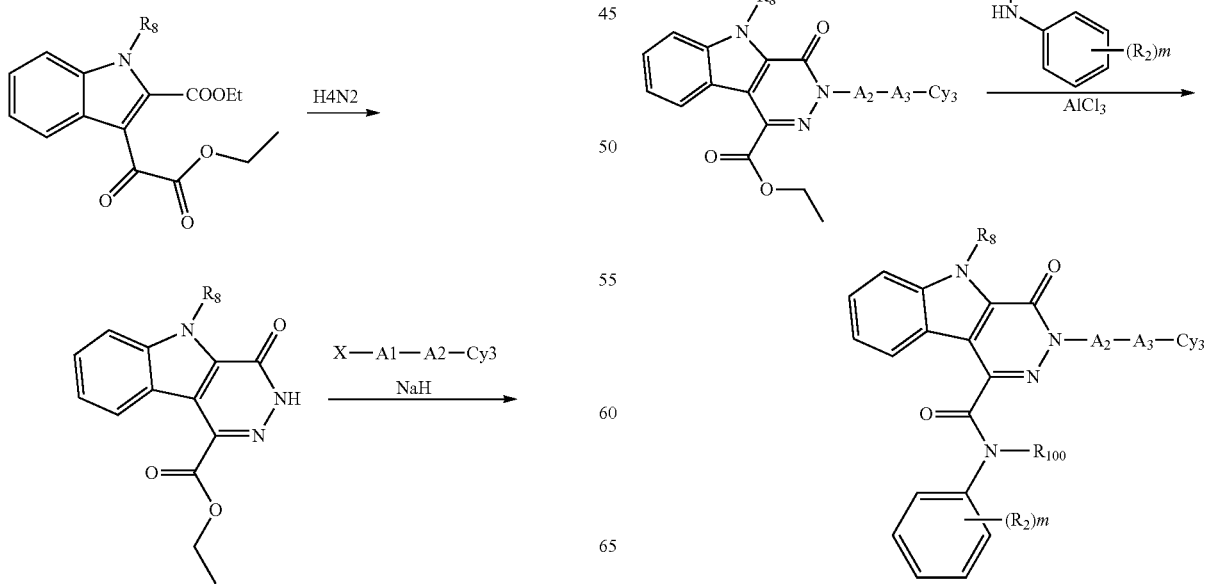

Scheme 9:

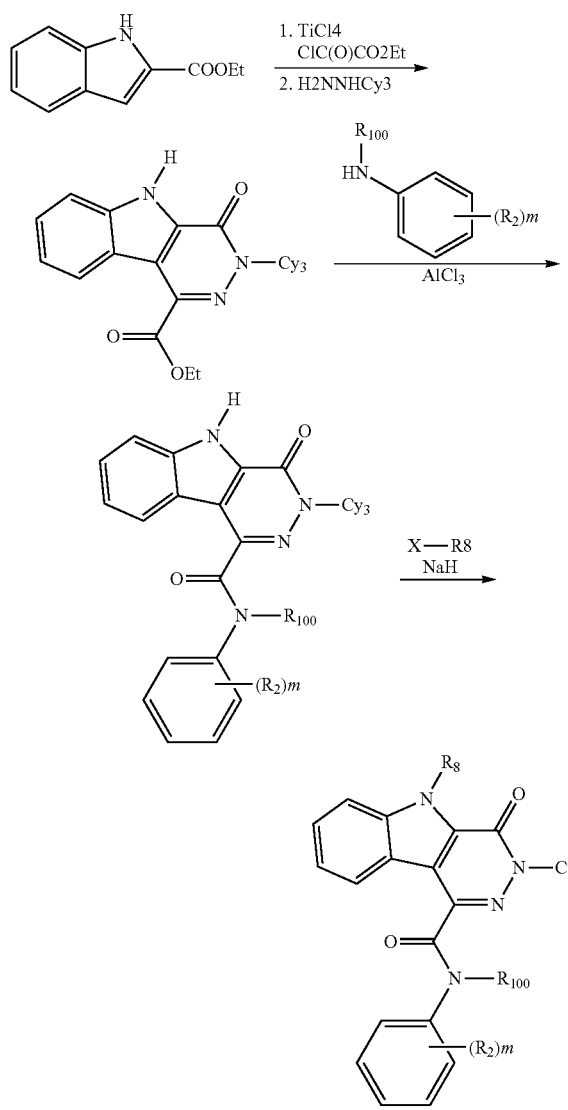

Scheme 10:

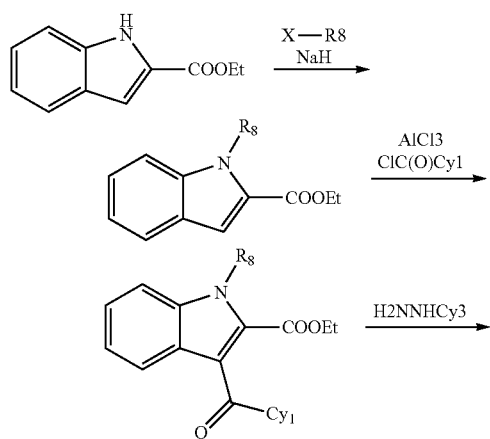

-continued

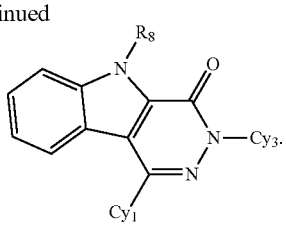

Compounds of the invention are useful as modulators of CFTR and treating diseases or disorders mediated by CFTR such as for the treatment of disease, disorders or conditions such as Cystic fibrosis, Hereditary emphysema, Hereditary hemochromatosis, Coagulation-Fibrinolysis deficiencies, such as Protein C deficiency, Type I hereditary angioedema, Lipid processing deficiencies, such as Familial hypercholesterolemia, Type 1 chylomicronemia, Abetalipoproteinemia, Lysosomal storage diseases, such as disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type I, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3—CH_2—$), or in other instances, a bivalent linking moiety can be "alkyl," in which case those skilled in the art will understand the alkyl to be a divalent radical (e.g., $—CH_2—CH_2—$), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug," and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

Example 1: Synthesis of N-ethyl-N-(4-ethylphenyl)-2-(1-oxo-4-phenylphthalazin-2(1H)-yl)acetamide

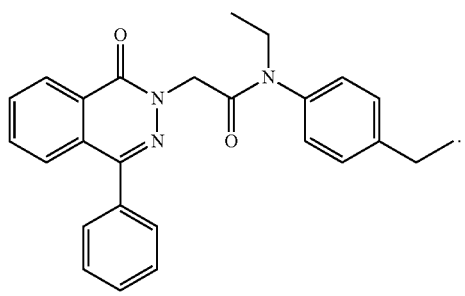 [SMILES: CCc1ccc(N(CC)C(=O)Cn2nc(-c3ccccc3)c3ccccc3c2=O)cc1]

2-bromo-N-ethyl-N-(4-ethylphenyl)acetamide

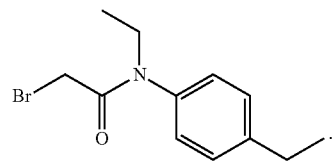

To a stirring solution of 4-ethylaniline (5.13 mL, 41.3 mmol) in THF (44 mL) at 0° C. was added a mixture of acetaldehyde (2.55 mL, 45.4 mmol), $H_2SO_4$ (3.09 mL, 12.38 mmol) and tetrahydrofuran (THF; 117 mL). The mixture formed a white slurry that was allowed to stir for 10 min before the addition of $NaBH_4$ (1.030 g, 27.2 mmol). After several hours, additional $NaBH_4$ (0.390 g, 10.32 mmol) was added and the reaction was monitored by TLC until the starting material was consumed. The reaction was quenched with $NH_4Cl$ (aq) and extracted with diethyl ether ($Et_2O$). The organic phase was washed with brine, dried over $MgSO_4$ and evaporated to dryness. Purification by silica gel chromatography (10-20% EtOAc/hexane) yielded 3.0 g (48%) of N, 4-diethylaniline. A round bottomed flask under $N_2$ was charged with 4-dimethylaminopyridine (DMAP; 0.018 g, 0.147 mmol), N, 4-diethylaniline (0.5 g, 2.95 mmol) and $CH_2Cl_2$ (29.5 mL). 2-Bromoacetic acid (0.975 g, 7.02 mmol) was added followed by ethylene dichloride (EDC; 1.357 g, 7.08 mmol). After stirring for 12 h, the reaction was diluted with DCM and washed with brine and 2 M NaOH. The organic layer was dried over $MgSO_4$ and purified by silica gel chromatography (10-20% EtOAc/pet. ether) to yield 650 mg of 2-bromo-N-ethyl-N-(4-ethylphenyl)acetamide.

4-oxo-3,4-dihydrophthalazin-1-yl 4-methylbenzenesulfonate

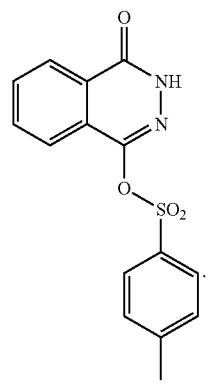 [SMILES: Cc1ccc(S(=O)(=O)Oc2n[nH]c(=O)c3ccccc23)cc1]

To a solution of 2,3-dihydrophthalazine-1,4-dione (10 g, 61.7 mmol) in pyridine (190 mL) was added 4-methylbenzene-1-sulfonyl chloride (11.76 g, 61.7 mmol). The reaction vessel was capped with a reflux condenser under $N_2$ and the mixture was stirred for 3 h at reflux then at rt overnight. The reaction was evaporated to dryness and the resulting thick white gel was taken up in 1:1 ethyl acetate (EtOAc) and $NaHCO_3$ (aq). A granular white solid was filtered and washed with water, EtOAc and $NaHCO_3$ (aq). The white solid was dried overnight to deliver 12.9 g (66% yield; LCMS m/z 317 [M+H]) of 4-oxo-3,4-dihydrophthalazin-1-yl 4-methylbenzenesulfonate.

3-(2-(ethyl(4-ethylphenyl)amino)-2-oxoethyl)-4-oxo-3,4-dihydrophthalazin-1-yl-4-methylbenzenesulfonate

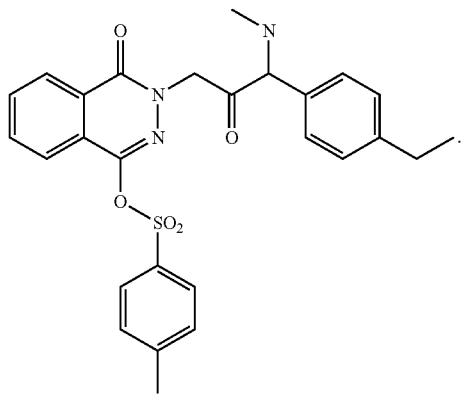 [SMILES: CCc1ccc(C(NC)C(=O)Cn2nc(OS(=O)(=O)c3ccc(C)cc3)c3ccccc3c2=O)cc1]

NaH (60%) (0.306 g, 7.64 mmol) was suspended in N,N-dimethyl formamide (DMF; 66.5 mL), then treated with 4-oxo-3,4-dihydrophthalazin-1-yl 4-methylbenzenesulfonate (2.102 g, 6.65 mmol) in portions over ~1 min. When the bubbling had subsided, 2-bromo-N-ethyl-N-(4-ethylphenyl)acetamide (1.5 g, 6.65 mmol) and NaI (0.498 g, 3.32 mmol) were added. After stirring 16 hr, the reaction was quenched by addition of ice, then diluted with DCM. The aq. layer was extracted with DCM (2×), and the combined organic layers were washed 4×5% LiCl (aq) and 1× brine, dried with MgSO$_4$, and evaporated onto silica del. The material was chromatographed (20% EtOAc/pet ether) to yield a white solid product 3-(2-(ethyl(4-ethylphenyl)amino)-2-oxoethyl)-4-oxo-3,4-dihydrophthalazin-1-yl 4-methylbenzenesulfonate (1.62 g, 48.2% yield; LCMS m/z 506 [M+H]).

Example 1: N-ethyl-N-(4-ethylphenyl)-2-(1-oxo-4-phenylphthalazin-2(1H)-yl)acetamide

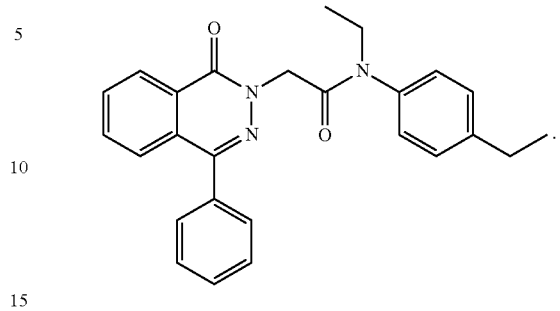

A microwave vial containing 3-(2-(ethyl(4-ethylphenyl)amino)-2-oxoethyl)-4-oxo-3,4-dihydrophthalazin-1-yl 4-methylbenzenesulfonate (50 mg, 0.099 mmol), phenylboronic acid (24.12 mg, 0.198 mmol), Na$_2$CO$_3$ (26.2 mg, 0.247 mmol), and bis(triphenylphosphine)palladium (II) chloride (4.86 mg, 6.92 µmol) was flushed with N$_2$, then THF (1.5 mL) and water (0.5 mL) were added. The mixture was heated in the microwave at 155° C. for 45 min. The reaction was filtered and the product was extracted 3×EtOAc. The combined organic layers were washed with water and brine, dried over MgSO$_4$, and evaporated to dryness. The resulting material was purified by reverse phase HPLC. The pure fractions were combined and evaporated to deliver pure N-ethyl-N-(4-ethylphenyl)-2-(1-oxo-4-phenylphthalazin-2 (1H)-yl)acetamide (8.8 mg, LCMS m/z 412 [M+H]).

Representative compounds of the invention were prepared in a similar manner to Example 1 (scheme 1) using the appropriate commercially available boronic acid or boronic ester.

| Example No. | Structure | IUPAC Name | LCMS m/z |
|---|---|---|---|
| 2. | 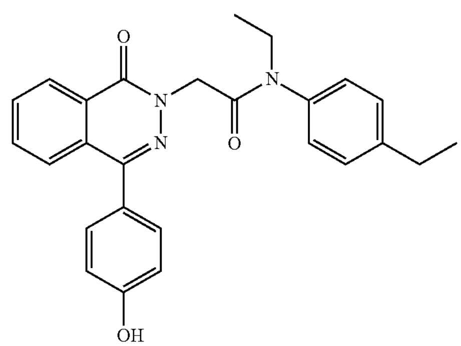 [SMILES: CCc1ccc(N(CC)C(=O)Cn2nc(-c3ccc(O)cc3)c3ccccc3c2=O)cc1] | N-ethyl-N-(4-ethylphenyl)-2-(4-(4-hydroxyphenyl)-1-oxophthalazin-2(1H)-yl)acetamide: | 428 [M + H] |
| 3. | 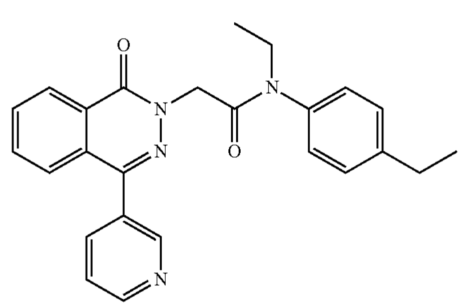 | N-ethyl-N-(4-ethylphenyl)-2-(1-oxo-4-(pyridin-3-yl)phthalazin-2(1H)-yl)acetamide | 413 [M + H] |

-continued

| Example No. | Structure | IUPAC Name | LCMS m/z |
|---|---|---|---|
| 4. | 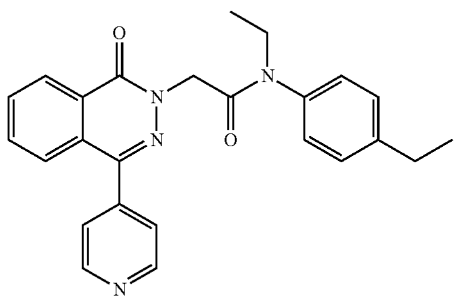 [SMILES: CCc1ccc(N(CC)C(=O)Cn2nc(-c3ccncc3)c3ccccc3c2=O)cc1] | N-ethyl-N-(4-ethylphenyl)-2-(1-oxo-4-(pyridin-4-yl)phthalazin-2(1H)-yl)acetamide | 413 [M + H] |
| 5. | 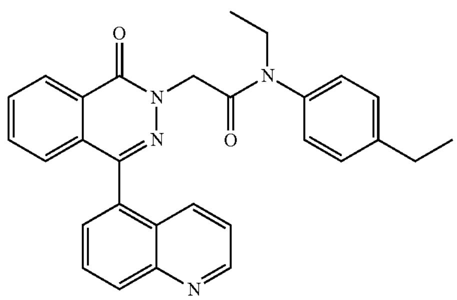 [SMILES: CCc1ccc(N(CC)C(=O)Cn2nc(-c3cccc4ncccc34)c3ccccc3c2=O)cc1] | N-ethyl-N-(4-ethylphenyl)-2-(1-oxo-4-(quinolin-5-yl)phthalazin-2(1H)-yl)acetamide | 463 [M + H] |
| 6. | 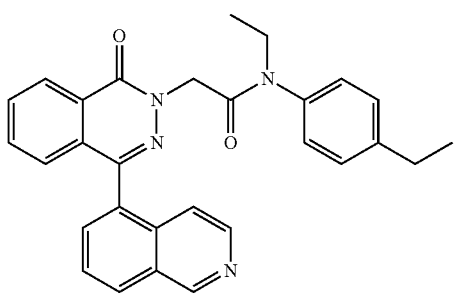 [SMILES: CCc1ccc(N(CC)C(=O)Cn2nc(-c3cccc4cnccc34)c3ccccc3c2=O)cc1] | N-ethyl-N-(4-ethylphenyl)-2-(4-(isoquinolin-5-yl)-1-oxophthalazin-2(1H)-yl)acetamide | 463 [M + H] |
| 7. | 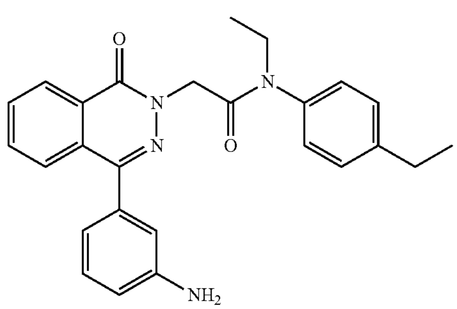 [SMILES: CCc1ccc(N(CC)C(=O)Cn2nc(-c3cccc(N)c3)c3ccccc3c2=O)cc1] | 2-(4-(3-aminophenyl)-1-oxophthalazin-2(1H)-yl)-N-ethyl-N-(4-ethylphenyl)acetamide | 427 [M + H] |
| 8. | 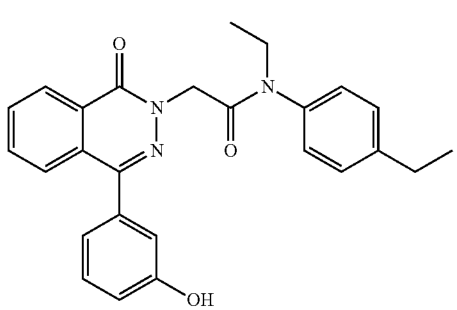 [SMILES: CCc1ccc(N(CC)C(=O)Cn2nc(-c3cccc(O)c3)c3ccccc3c2=O)cc1] | N-ethyl-N-(4-ethylphenyl)-2-(4-(3-hydroxyphenyl)-1-oxophthalazin-2(1H)-yl)acetamide | 428 [M + H] |

-continued

| Example No. | Structure | IUPAC Name | LCMS m/z |
|---|---|---|---|
| 9. | 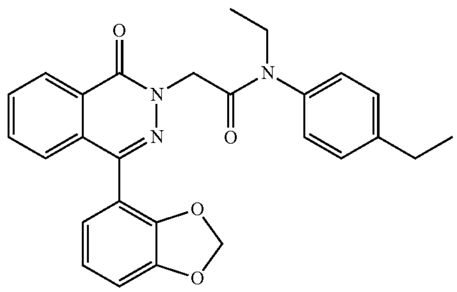 [SMILES: CCc1ccc(N(CC)C(=O)Cn2nc(-c3cccc4c3OCO4)c3ccccc3c2=O)cc1] | 2-(4-(benzo[d][1,3]dioxol-4-yl)-1-oxophthalazin-2(1H)-yl)-N-ethyl-N-(4-ethylphenyl)acetamide | 456 [M + H] |
| 10. | 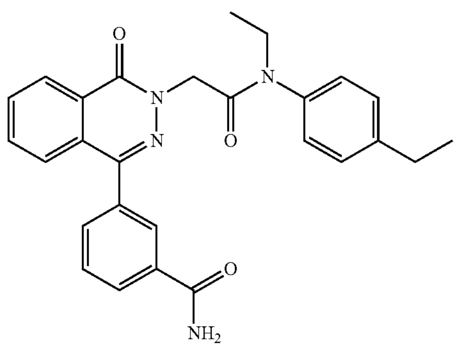 [SMILES: CCc1ccc(N(CC)C(=O)Cn2nc(-c3cccc(C(N)=O)c3)c3ccccc3c2=O)cc1] | 3-(3-(2-(ethyl(4-ethylphenyl)amino)-2-oxoethyl)-4-oxo-3,4-dihydrophthalazin-1-yl)benzamide | 455 [M + H] |
| 11. | 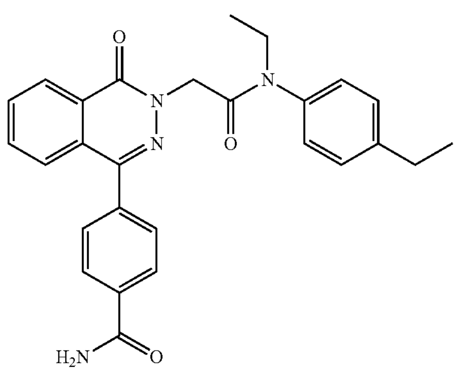 [SMILES: CCc1ccc(N(CC)C(=O)Cn2nc(-c3ccc(C(N)=O)cc3)c3ccccc3c2=O)cc1] | 4-(3-(2-(ethyl(4-ethylphenyl)amino)-2-oxoethyl)-4-oxo-3,4-dihydrophthalazin-1-yl)benzamide | 455 [M + H] |
| 12. | 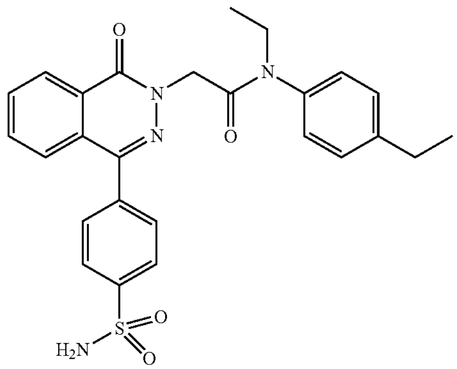 [SMILES: CCc1ccc(N(CC)C(=O)Cn2nc(-c3ccc(S(N)(=O)=O)cc3)c3ccccc3c2=O)cc1] | N-ethyl-N-(4-ethylphenyl)-2-(1-oxo-4-(4-sulfamoylphenyl)phthalazin-2(1H)-yl)acetamide | 491 [M + H] |

-continued

| Example No. | Structure | IUPAC Name | LCMS m/z |
|---|---|---|---|
| 13. | 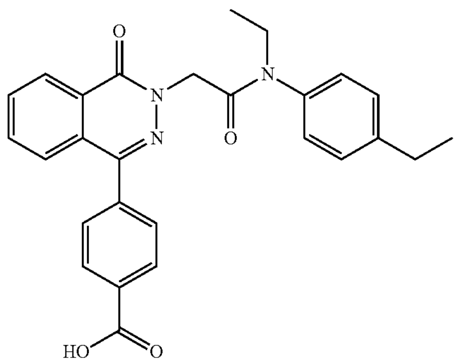 [SMILES: CCc1ccc(N(CC)C(=O)Cn2nc(-c3ccc(C(=O)O)cc3)c3ccccc3c2=O)cc1] | 4-(3-(2-(ethyl(4-ethylphenyl)amino)-2-oxoethyl)-4-oxo-3,4-dihydrophthalazin-1-yl)benzoic acid | 456 [M + H] |
| 14. | 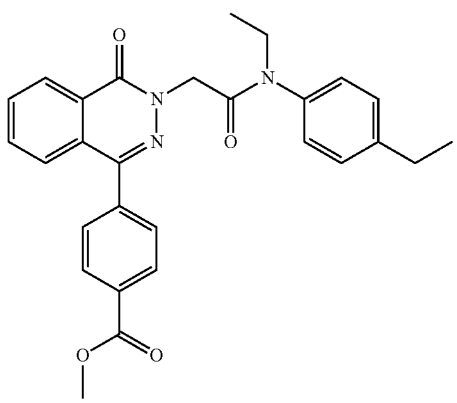 [SMILES: CCc1ccc(N(CC)C(=O)Cn2nc(-c3ccc(C(=O)OC)cc3)c3ccccc3c2=O)cc1] | methyl 4-(3-(2-(ethyl(4-ethylphenyl)amino)-2-oxoethyl)-4-oxo-3,4-dihydrophthalazin-1-yl)benzoate | 470 [M + H] |
| 15. | 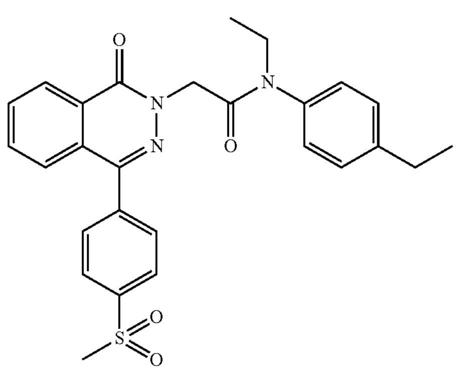 [SMILES: CCc1ccc(N(CC)C(=O)Cn2nc(-c3ccc(S(C)(=O)=O)cc3)c3ccccc3c2=O)cc1] | N-ethyl-N-(4-ethylphenyl)-2-(4-(4-(methylsulfonyl)phenyl)-1-oxophthalazin-2(1H)-yl)acetamide | 490 [M + H] |
| 16. | 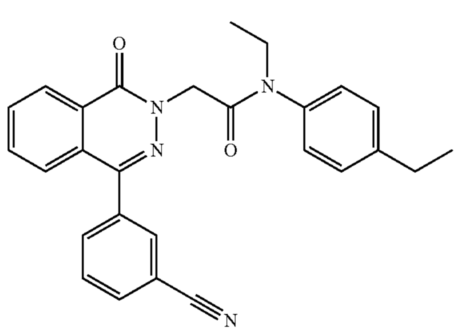 [SMILES: CCc1ccc(N(CC)C(=O)Cn2nc(-c3cccc(C#N)c3)c3ccccc3c2=O)cc1] | 2-(4-(3-cyanophenyl)-1-oxophthalazin-2(1H)-yl)-N-ethyl-N-(4-ethylphenyl)acetamide | 437 [M + H] |

-continued

| Example No. | Structure | IUPAC Name | LCMS m/z |
|---|---|---|---|
| 17. | 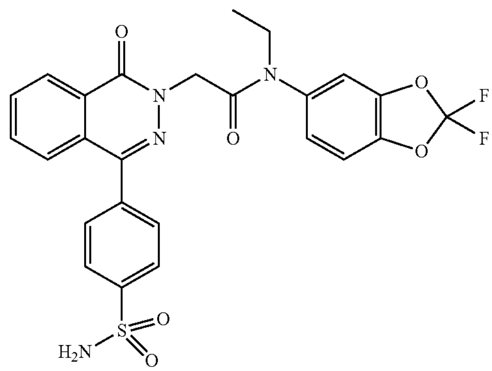 [SMILES: CCN(C(=O)Cn1nc(-c2ccc(S(N)(=O)=O)cc2)c2ccccc2c1=O)c1ccc2c(c1)OC(F)(F)O2] | N-(2,2-difluorobenzo[d][1,3]dioxol-5-yl)-N-ethyl-2-(1-oxo-4-(4-sulfamoyl-phenyl)phthalazin-2(1H)-yl)acetamide | 543 [M + H] |
| 18. | 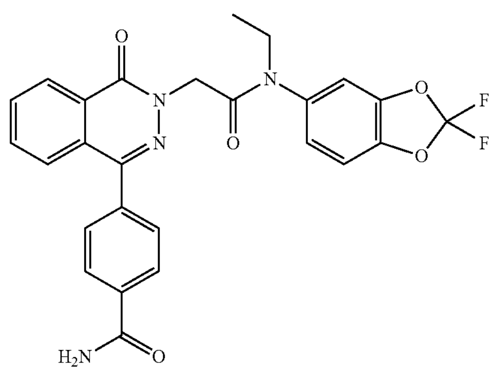 [SMILES: CCN(C(=O)Cn1nc(-c2ccc(C(N)=O)cc2)c2ccccc2c1=O)c1ccc2c(c1)OC(F)(F)O2] | 4-(3-(2-((2,2-difluorobenzo[d][1,3]dioxol-5-yl)(ethyl)amino)-2-oxoethyl)-4-oxo-3,4-dihydro-phthalazin-1-yl)benzamide | 507 [M + H] |
| 19. | 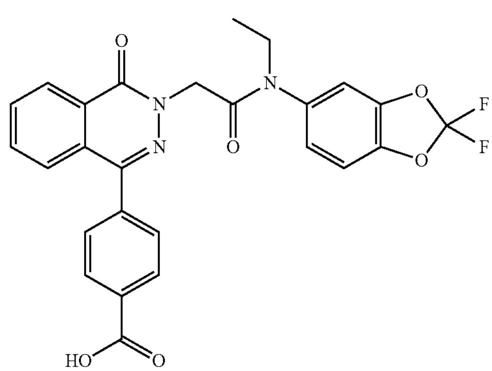 [SMILES: CCN(C(=O)Cn1nc(-c2ccc(C(=O)O)cc2)c2ccccc2c1=O)c1ccc2c(c1)OC(F)(F)O2] | 4-(3-(2-((2,2-difluorobenzo[d][1,3]dioxol-5-yl)(ethyl)amino)-2-oxoethyl)-4-oxo-3,4-dihydrophthalazin-1-yl)benzoic acid | 508 [M + H] |
| 20 | 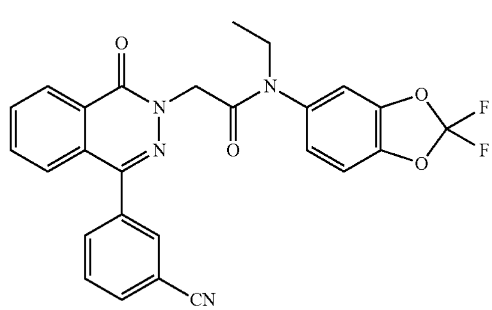 [SMILES: CCN(C(=O)Cn1nc(-c2cccc(C#N)c2)c2ccccc2c1=O)c1ccc2c(c1)OC(F)(F)O2] | 2-(4-(3-cyanophenyl)-1-oxophthalazin-2(1H)-yl)-N-(2,2-difluorobenzo[d][1,3]dioxol-5-yl)-N-ethylacetamide | 489 [M + H] |

| Example No. | Structure | IUPAC Name | LCMS m/z |
|---|---|---|---|
| 21. | 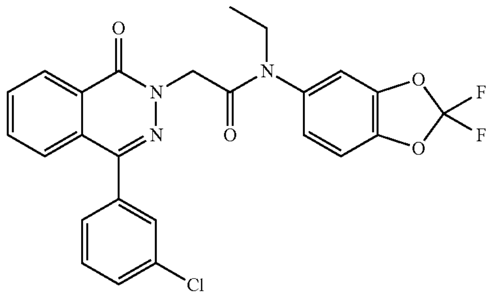 [SMILES: CCN(C(=O)Cn1nc(-c2cccc(Cl)c2)c2ccccc2c1=O)c1ccc2c(c1)OC(F)(F)O2] | 2-(4-(3-chlorophenyl)-1-oxophthalazin-2(1H)-yl)-N-(2,2-difluorobenzo[d][1,3]dioxol-5-yl)-N-ethylacetamide | |
| 22. | 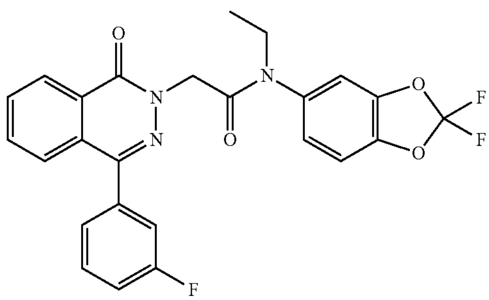 | N-(2,2-difluorobenzo[d][1,3]dioxol-5-yl)-N-ethyl-2-(4-(3-fluorophenyl)-1-oxophthalazin-2(1H)-yl)acetamide | |
| 23. | 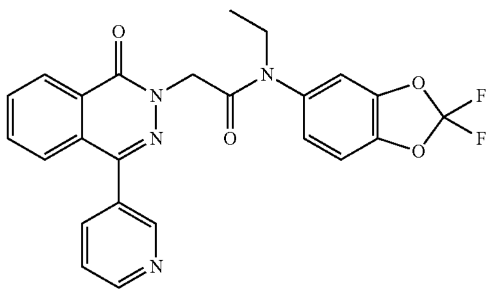 [SMILES: CCN(C(=O)Cn1nc(-c2cccnc2)c2ccccc2c1=O)c1ccc2c(c1)OC(F)(F)O2] | N-(2,2-difluorobenzo[d][1,3]dioxol-5-yl)-N-ethyl-2-(1-oxo-4-(pyridin-3-yl)phthalazin-2(1H)-yl)acetamide | |

N-ethyl-2,2-difluorobenzo[d][1,3]dioxol-5-amine

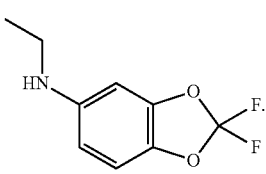

To a solution of 2,2-difluoro-5-aminobenzo[d][1,3]dioxole (7.45 g, 43.0 mmol) in DMF (60 mL) was added K$_2$CO$_3$ (17.8 g, 129.0 mmol) and the reaction mixture was stirred at rt for 1 hr. The reaction was cooled to 0° C. and EtI (3.52 mL, 43.0 mmol) was added dropwise. After stirring at rt for 16 hr, the reaction mixture was diluted with water (500 mL) and the product extracted with EtOAc (3×100 mL). The combined organics were washed with brine (200 mL) dried over Na$_2$SO$_4$, and concentrated. The crude product was purified by chromatography (0-10% EtOAc/hexane) to yield EtOAcN-ethyl-2,2-difluorobenzo[d][1,3]dioxol-5-amine (5.98 g, 202.39 [M+H]).

2-Bromo-N-(2,2-difluorobenzo[d][1,3]dioxol-5-yl)-N-ethylacetamide

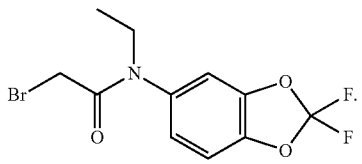

A solution of N-ethyl-2,2-difluorobenzo[d][1,3]dioxol-5-amine (8.0 g, 3.9 mmol) in DCM (100 mL) was treated with 2-bromoaceticacid (13.2 g, 9.4 mmol), EDC.HCL (14.8 g, 93.6 mmol) and DMAP (238 mg, 19.5 mmol), then stirred at rt for 16 hr. The reaction mixture was diluted with water (500 mL) and the product extracted with DCM (3×100 mL). The combined organics were washed with brine, dried over Na$_2$SO$_4$, and concentrated. The crude product was purified by chromatography (0-7% EtOAc/hexane) to yield EtOAc 2-bromo-N-(2,2-difluorobenzo[d][1,3]dioxol-5-yl)-N-ethylacetamide (11.0 g, 322.01 [M+H]). $^1$H NMR: (400 MHz, DMSO) δ: 1.03-1.00 (t, J=14.4, 3H), 3.68-3.63 (m, 2H), 4.03 (s, 2H) 7.26-7.23 (d, J=8.4, 1H), 7.53-7.50 (d, J=8.4, 1H), 7.57 (s, 1H).

3-(2-((2,2-difluorobenzo[d][1,3]dioxol-5-yl)(ethyl)
amino)-2-oxoethyl)-4-oxo-3,4-dihydrophthalazin-1-
yl-4-methylbenzenesulfonate

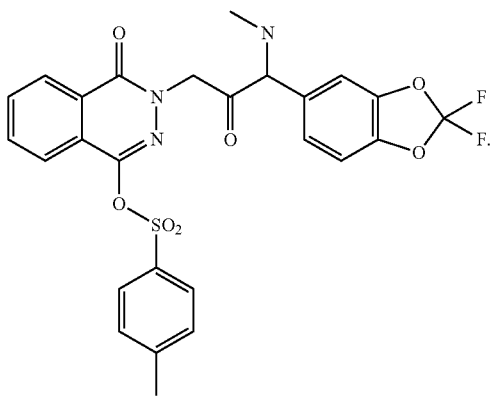 [SMILES: CNC(C(=O)Cn1nc(OS(=O)(=O)c2ccc(C)cc2)c2ccccc2c1=O)c1ccc2c(c1)OC(F)(F)O2]

A 0° C. solution of 4-oxo-3,4-dihydrophthalazin-1-yl 4-methylbenzenesulfonate (0.3751 g, 1.186 mmol) in DMF (5.93 mL) was treated with NaHMDS (2M in THF, 0.65 mL, 1.30 mmol). After stirring for 20 min, a solution of 2-bromo-N-(2,2-difluorobenzo[d][1,3]dioxol-5-yl)-N-ethylacetamide (0.458 g, 1.423 mmol) in DMF (1.0 mL) was added and the mixture stirred overnight. The reaction was quenched with 5% LiCl (aq) and extracted with EtOAc. The combined organics were over MgSO$_4$ and concentrated. The crude product was purified by chromatography (10-100% EtOAc/ pet ether) to yield 3-(2-((2,2-difluorobenzo[d][1,3]dioxol-5-yl)(ethyl)amino)-2-oxoethyl)-4-oxo-3,4-dihydrophthalazin-1-yl 4-methylbenzenesulfonate (479 mg, 558 [M+H]).

Example 25: Synthesis of N-ethyl-N-(4-ethylphenyl)-2-(1-oxo-4-(pyridin-3-ylmethyl)phthalazin-2(1H)-yl)acetamide

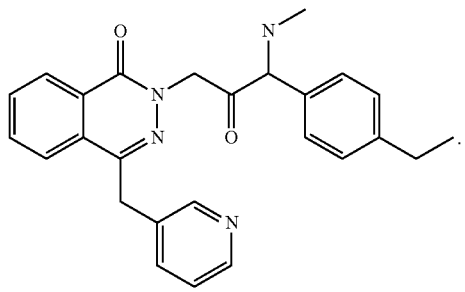 [SMILES: CCc1ccc(C(NC)C(=O)Cn2nc(Cc3cccnc3)c3ccccc3c2=O)cc1]

3-(pyridin-3-ylmethylene)isobenzofuran-1(3H)-one

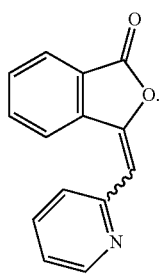 [SMILES: O=C1OC(=Cc2ccccn2)c2ccccc21]

A mixture of 3-(carboxymethyl)pyridin-1-ium chloride (13 g, 74.9 mmol), isobenzofuran-1,3-dione (11.09 g, 74.9 mmol), and sodium acetate (0.246 g, 3.00 mmol) was placed into a round bottom flask and warmed to 190° C. for 30 minutes. The mixture extracted with DCM and washed with NaHCO$_3$ (aq). The organic phase was dried over MgSO$_4$ and evaporated to give 3-(pyridin-3-ylmethylene) isobenzofuran-1(3H)-one (8.5 g).

4-(pyridin-3-ylmethyl)phthalazin-1(2H)-one

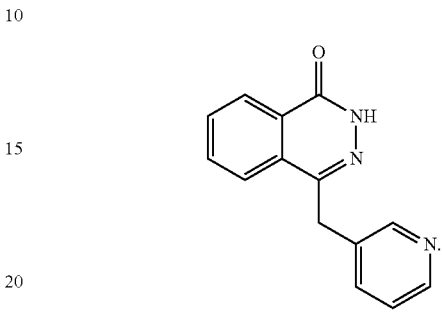

Two N$_2$ purged microwave vials, each containing 3-(pyridin-3-ylmethylene)isobenzofuran-1(3H)-one (1.5 g, 6.72 mmol), hydrazine sulfate (0.874 g, 6.72 mmol), water (6.5 mL), ethanol (1.9 mL) and 2M NaOH (1.9 mL, aqueous), were warmed in a microwave to 180° C. for 15 min. The resulting mixtures were cooled to room temp and placed in the freezer to precipitate solid. The product was diluted with water and filtered to provide a solid that was dried in a desiccator overnight to deliver 4-(pyridin-3-ylmethyl) phthalazin-1(2H)-one (2.36 g, 238 [M+H]).

N-ethyl-N-(4-ethylphenyl)-2-(1-oxo-4-(pyridin-3-ylmethyl)phthalazin-2(1H)-yl)acetamide

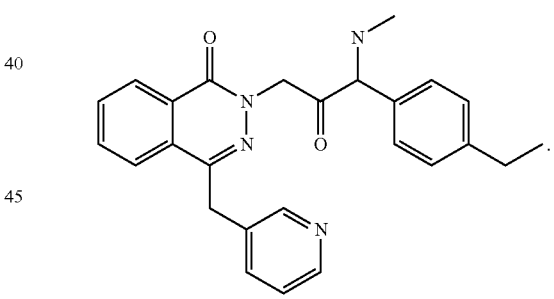

To a vial stirring at 0° C. containing NaH (60%) (6.49 mg, 0.162 mmol) and DMF (738 µL) was added a solution of 4-(pyridin-3-ylmethyl)phthalazin-1(2H)-one (35 mg, 0.148 mmol) in DMF (369 µL). After 10 min, 2-bromo-N-ethyl-N-(4-ethylphenyl)acetamide (39.9 mg, 0.148 mmol) in DMF (369 µL) was added. The reaction was allowed to stir overnight. Aqueous NH$_4$Cl was added and the product was extracted with EtOAc. The organic phase was washed with brine, dried over MgSO$_4$ and evaporated. The crude product was purified by chromatography (0-5% MeOH/ EtOAc) to give N-ethyl-N-(4-ethylphenyl)-2-(1-oxo-4-(pyridin-3-ylmethyl)phthalazin-2(1H)-yl)acetamide (20 mg, 427 [M+H]).

Representative compounds of the invention were prepared in a similar manner to example 22 (scheme 2).

| Example No. | Structure | IUPAC Name | LCMS m/z |
|---|---|---|---|
| 26. | 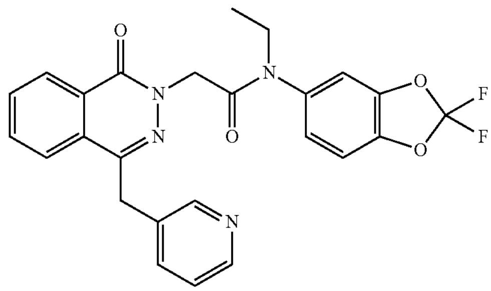 [SMILES: CCN(C(=O)Cn1nc(Cc2cccnc2)c2ccccc2c1=O)c1ccc2c(c1)OC(F)(F)O2] | N-(2,2-difluorobenzo[d][1,3]dioxol-5-yl)-N-ethyl-2-(1-oxo-4-(pyridin-3-ylmethyl)phthalazin-2(1H)-yl)acetamide | 479 [M + H] |
| 27. | 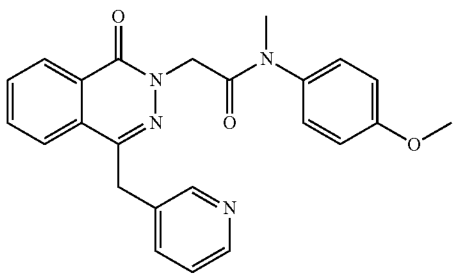 [SMILES: COc1ccc(N(C)C(=O)Cn2nc(Cc3cccnc3)c3ccccc3c2=O)cc1] | N-(4-methoxyphenyl)-N-methyl-2-(1-oxo-4-(pyridin-3-ylmethyl)phthalazin-2(1H)-yl)acetamide | 415 [M + H] |

2-chloro-N-(4-methoxyphenyl)-N-methylacetamide

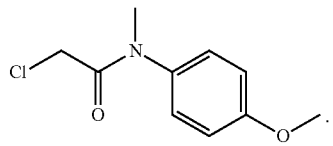

A solution of DMAP (0.022 g, 0.182 mmol), 4-methoxy-N-methylaniline (0.5 g, 3.64 mmol) and DCM (36.4 mL) under N₂ was treated with 2-bromoacetic acid (1.205 g, 8.67 mmol) and EDC hydrochloride (1.677 g, 8.75 mmol), then stirred overnight at rt. The reaction was diluted with DCM and washed with brine and 2 M NaOH. The organic layer was dried over MgSO₄ and evaporated to dryness. The crude product was purified by chromatography (10-20% EtOAc/pet ether) to give 2-chloro-N-(4-methoxyphenyl)-N-methylacetamide (446 mg).

Examples 28 and 29

Synthesis of N-ethyl-N-(4-ethylphenyl)-2-(7-methyl-1-oxo-4-(pyridin-3-ylmethyl)phthalazin-2(1H)-yl)acetamide and N-ethyl-N-(4-ethylphenyl)-2-(6-methyl-1-oxo-4-(pyridin-3-ylmethyl)phthalazin-2(1H)-yl)acetamide

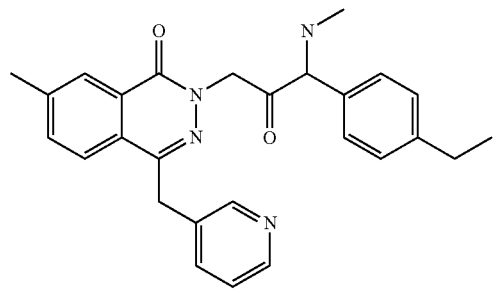

-continued

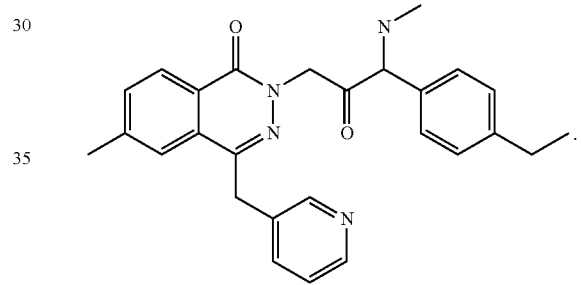

Preparation of 6-methylisobenzofuran-1(3H)-one and 5-methylisobenzofuran-1(3H)-one

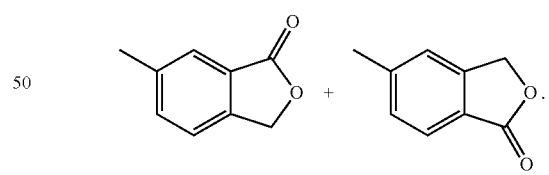

To a stirred solution of 4-methyl phthalic anhydride (5.0 g, 30.8 mmol) in THF (35 mL) were added HOAc (3.43 mL, 61.6 mmol) and NaBH₄ (1.13 g, 30.8 mmol) at 15° C. The mixture was stirred at 15° C. for 30 min and then at rt for 4 hr, and then concentrated under vacuum. HOAc (15 mL) and Ac₂O (15 mL) were added and the mixture heated at 110° C. for 3 hr. Reaction mixture was concentrated, quenched with NH₄Cl (aq) (500 mL) and then extracted with EtOAc (2×250 mL). The organic layer was washed with brine, dried over Na₂SO₄, and concentrated. The crude product was purified by chromatography (0-15% EtOAc/hexane) to obtain 6-methylisobenzofuran-1(3H)-one and 5-methylisobenzofuran-1(3H)-one (2.0 g) as a 1:4.4 isomeric mixture (LCMS: 238 nM $R_T$ 2.659 min and 2.716 min, 149 [M+H]).

3-hydroxy-6-methyl-2-(pyridin-3-yl)-1H-inden-1-one

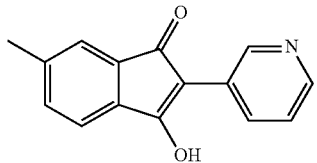

The mixture of 6-methylisobenzofuran-1(3H)-one and 5-methylisobenzofuran-1(3H)-one (2.0 g, 13.5 mmol) was dissolved in EtOAc (10 mL) and MeOH (20 mL), then treated with 3-pyridine carboxaldehyde (1.44 g, 13.5 mmol) and NaOMe (2.18 g, 40.0 mmol) portionwise at 0° C. The reaction mixture stirred for 30 min at 0° C. and then was heated at 60° C. for 3 h. The reaction mixture was concentrated under vacuum, diluted with water (50 mL) and acidified with acetic acid (10 mL). The resulting precipitate was filtered and dried to obtained 3-hydroxy-6-methyl-2-(pyridin-3-yl)-1-H-inden-1-one (1.54 g, 238 [M+H]). $^1$H NMR: (400 MHz, DMSO) δ: 2.358 (s, 3H), 7.206-7.146 (t, 1H), 7.225 (s, 1H), 7.813-7.778 (d, J=8.8 Hz, 1H), 8.225-8.206 (d, J=7.6, 1H), 9.470-9.441 (d, J=11.6 Hz, 1H), 9.733 (s, 1H), 14.910 (s, 1H).

7-methyl-4-(pyridin-3-ylmethyl)phthalazin-1(2H)-one and 6-methyl-4-(pyridin-3-ylmethyl)phthalazin-1(2H)-one

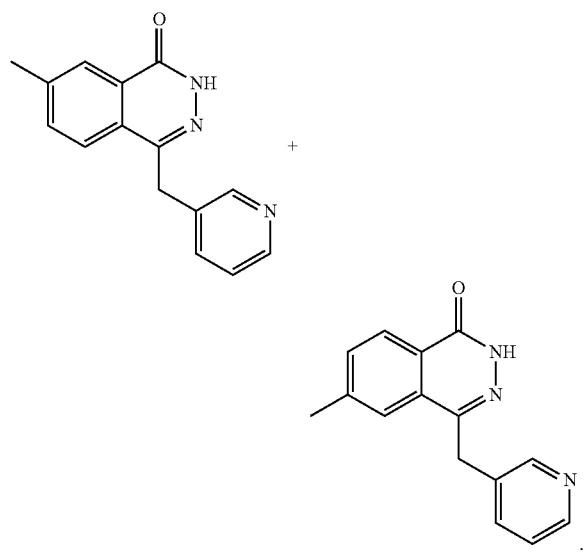

A solution of 3-hydroxy-6-methyl-2-(pyridin-3-yl)-1-H-inden-1-one (1.2 g, 5.0 mmol) in hydrazine hydrate (10 mL) was heated at 110° C. for 16 h. The reaction mixture was diluted with water (50 mL) and the resulting precipitate filtered and dried to obtained 7-methyl-4-(pyridin-3-yl-methyl)-phthalazine-1(2H)-one and 6-methyl-4-(pyridin-3-yl-methyl)-phthalazine-1(2H)-one (5.01 g, 252 [M+H]) as a 1:1 isomeric mixture. $^1$H NMR: (400 MHz, DMSO) δ: 2.486 (s, 6H), 4.300-4.325 (d, J=2 4H), 7.341-7.294 (m, 2H), 7.740-7.660 (m, 5H), 7.850 (s, 1H), 7.920-7.899 (d, J=8.4, 1H), 8.167-8.147 (d, J=8, 1H), 8.417-8.413 (m, 1H), 8.434-8.425 (m, 2H), 8.605-8.438 (m, 2H), 12.512 (s, 2H).

N-ethyl-N-(4-ethylphenyl)-2-(7-methyl-1-oxo-4-(pyridin-3-ylmethyl)phthalazin-2(1H)-yl)acetamide and N-ethyl-N-(4-ethylphenyl)-2-(6-methyl-1-oxo-4-(pyridin-3-ylmethyl)phthalazin-2(1H)-yl)acetamide Example 28

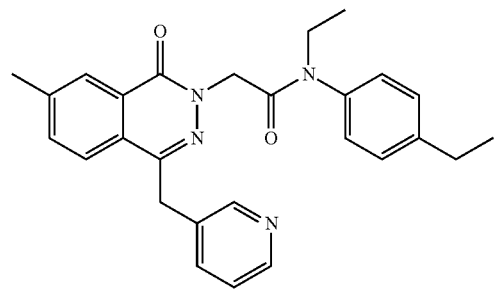

Example 29

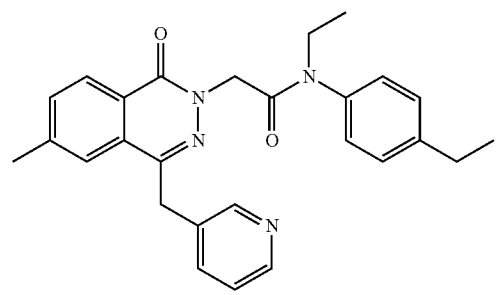

To a solution of 7-methyl-4-(pyridin-3-yl-methyl)-phthalazine-1(2H)-one and 6-methyl-4-(pyridin-3-yl-methyl)-phthalazine-1(2H)-one (0.5 g, 1.9 mmol) in THF (15 mL) was added NaH (0.087 g, 2.1 mmol) portion wise at 0° C. and the reaction mixture stirred for 30 min at 0° C. A solution of 2-bromo-N-ethyl-N-(4-ethylphenyl)acetamide (0.537 g, 1.9 mmol) in THF (5 mL) was added dropwise and the reaction mixture was stirred for 16 h at rt. The reaction was diluted with satd aq NH$_4$Cl (25 mL) and extracted with EtOAc (50 mL×2). The extract was washed with brine (50 mL), dried over anhydrous sodium sulfate and concentrated to give crude which was purified by preparative HPLC to obtain the separable isomers N-ethyl-N-(4-ethylphenyl)-2-(7-methyl-1-oxo-4-(pyridine-3-ylmethyl)-phthalazine-2(1H)-yl)acetamide (0.024 g, 441 [M+H]) and N-ethyl-N-(4-ethylphenyl)-2-(6-methyl-1-oxo-4-(pyridine-3-ylmethyl)-phthalazine-2(1H)-yl)acetamide (0.034 g, 441 [M+H]).

$^1$H NMR:

Example 28 (400 MHz, DMSO) δ: 1.050-1.009 (m, 3H), 1.233-1.195 (t, 3H), 2.518-2.483 (m, 3H), 2.689-2.632 (m, 2H), 3.688-3.635 (m, 2H), 4.318 (s, 2H), 4.559 (s, 2H), 7.367-7.284 (m, 5H), 7.721-7.661 (m, 2H), 7.877-7.856 (d, J=8.4, 1H), 8.036 (s, 1H), 8.157 (s, 1H), 8.597-8.407 (m, 1H), 8.601 (s, 1H).

Example 29 (400 MHz, DMSO) δ: 1.042-1.006 (t, 3H), 1.233-1.195 (t, 3H), 2.501 (s, 3H), 2.689-2.633 (m, 2H), 3.684-3.631 (m, 2H), 4.326 (s, 2H), 4.540 (s, 2H), 7.367-7.298 (m, 5H), 7.711-7.660 (m, 2H), 7.806 (s, 1H), 8.140-8.120 (d, J=8, 1H), 8.433-8.418 (m, 1H), 8.621-8.617 (d, J=1.6, 1H).

Representative compounds of the invention were prepared in a similar manner to examples 25 and 26 from the corresponding phthalic anhydride or isobenzofuran-1(3H)-one and the appropriate alkylating agent (scheme 3).

| Example No. | Structure | IUPAC Name | LCMS m/z |
| --- | --- | --- | --- |
| 30. | 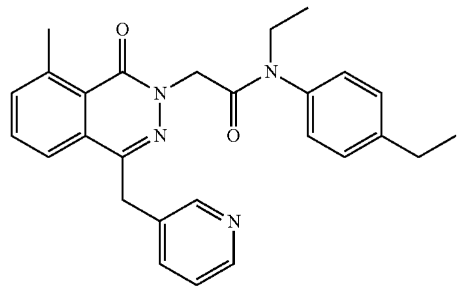 [SMILES: CCc1ccc(N(CC)C(=O)Cn2nc(Cc3cccnc3)c3cccc(C)c3c2=O)cc1] | N-ethyl-N-(4-ethylphenyl)-2-(8-methyl-1-oxo-4-(pyridin-3-ylmethyl)phthalazin-2(1H)-yl)acetamide | 441 [M + H] |
| 31. | 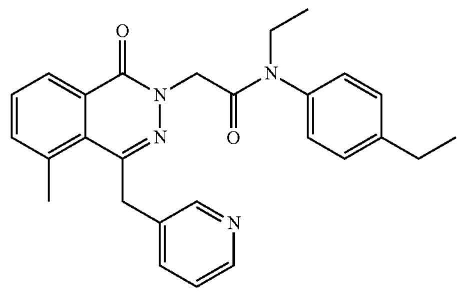 [SMILES: CCc1ccc(N(CC)C(=O)Cn2nc(Cc3cccnc3)c3c(C)cccc3c2=O)cc1] | N-ethyl-N-(4-ethylphenyl)-2-(5-methyl-1-oxo-4-(pyridin-3-ylmethyl)phthalazin-2(1H)-yl)acetamide | 441 [M + H] |
| 32. | 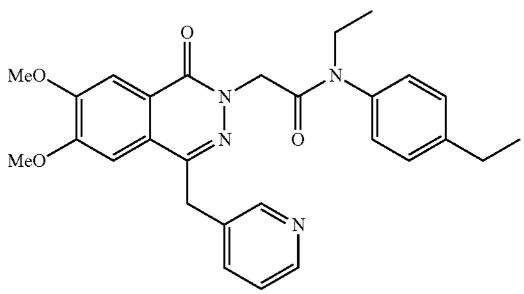 [SMILES: CCc1ccc(N(CC)C(=O)Cn2nc(Cc3cccnc3)c3cc(OC)c(OC)cc3c2=O)cc1] | 2-(6,7-dimethoxy-1-oxo-4-(pyridin-3-ylmethyl)phthalazin-2(1H)-yl)-N-ethyl-N-(4-ethylphenyl)acetamide | 487 [M + H] |
| 33. | 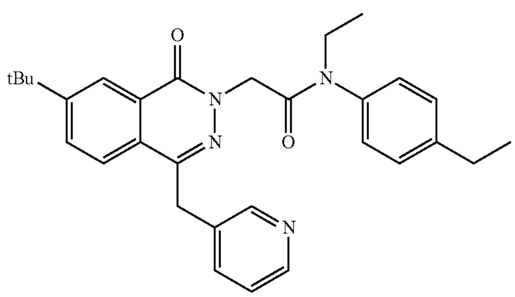 [SMILES: CCc1ccc(N(CC)C(=O)Cn2nc(Cc3cccnc3)c3ccc(C(C)(C)C)cc3c2=O)cc1] | 2-(7-(tert-butyl)-1-oxo-4-(pyridin-3-ylmethyl)phthalazin-2(1H)-yl)-N-ethyl-N-(4-ethylphenyl)acetamide | 483 [M + H] |
| 34. | 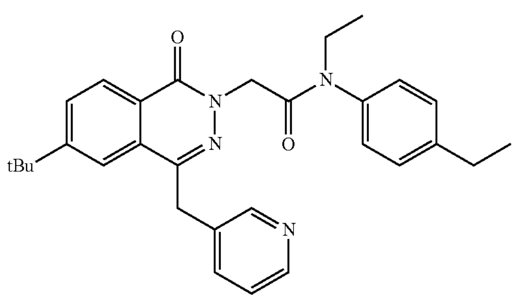 [SMILES: CCc1ccc(N(CC)C(=O)Cn2nc(Cc3cccnc3)c3cc(C(C)(C)C)ccc3c2=O)cc1] | 2-(6-(tert-butyl)-1-oxo-4-(pyridin-3-ylmethyl)phthalazin-2(1H)-yl)-N-ethyl-N-(4-ethylphenyl)acetamide | 483 [M + H] |

-continued

| Example No. | Structure | IUPAC Name | LCMS m/z |
|---|---|---|---|
| 35. | 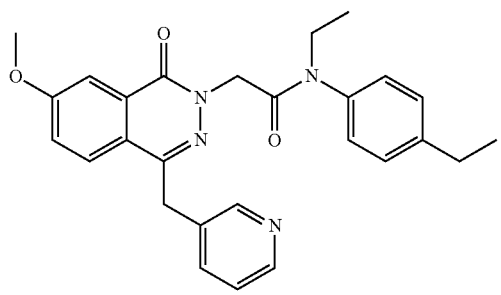 [SMILES: CCc1ccc(N(CC)C(=O)Cn2nc(Cc3cccnc3)c3ccc(OC)cc3c2=O)cc1] | N-ethyl-N-(4-ethylphenyl)-2-(7-methoxy-1-oxo-4-(pyridin-3-ylmethyl)phthalazin-2(1H)-yl)acetamide | 457 [M + H] |
| 36. | 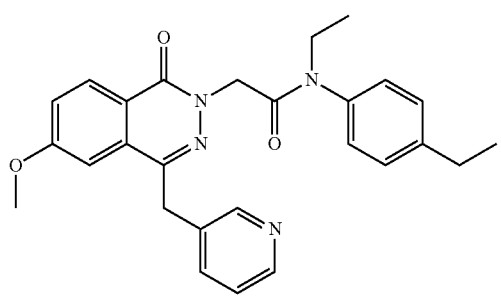 [SMILES: CCc1ccc(N(CC)C(=O)Cn2nc(Cc3cccnc3)c3cc(OC)ccc3c2=O)cc1] | N-ethyl-N-(4-ethylphenyl)-2-(6-methoxy-1-oxo-4-(pyridin-3-ylmethyl)phthalazin-2(1H)-yl)acetamide | 457 [M + H] |
| 37. | 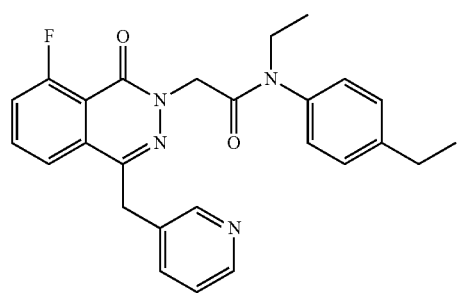 [SMILES: CCc1ccc(N(CC)C(=O)Cn2nc(Cc3cccnc3)c3cccc(F)c3c2=O)cc1] | N-ethyl-N-(4-ethylphenyl)-2-(8-fluoro-1-oxo-4-(pyridin-3-ylmethyl)phthalazin-2(1H)-yl)acetamide | 445 [M + H] |
| 38. | 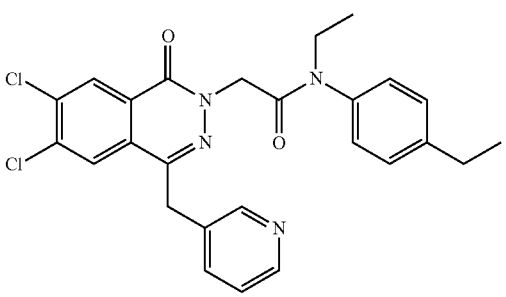 [SMILES: CCc1ccc(N(CC)C(=O)Cn2nc(Cc3cccnc3)c3cc(Cl)c(Cl)cc3c2=O)cc1] | 2-(6,7-dichloro-1-oxo-4-(pyridin-3-ylmethyl)phthalazin-2(1H)-yl)-N-ethyl-N-(4-ethylphenyl)acetamide | 495 [M + H] |
| 39. | 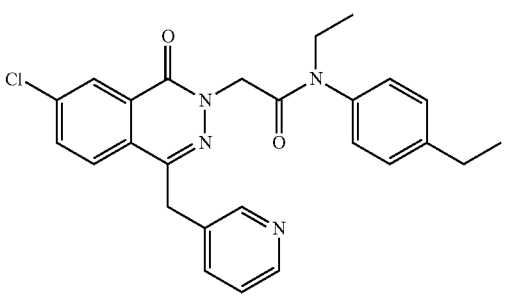 [SMILES: CCc1ccc(N(CC)C(=O)Cn2nc(Cc3cccnc3)c3ccc(Cl)cc3c2=O)cc1] | 2-(7-chloro-1-oxo-4-(pyridin-3-ylmethyl)phthalazin-2(1H)-yl)-N-ethyl-N-(4-ethylphenyl)acetamide | 461 [M + H] |

-continued

| Example No. | Structure | IUPAC Name | LCMS m/z |
|---|---|---|---|
| 40. | 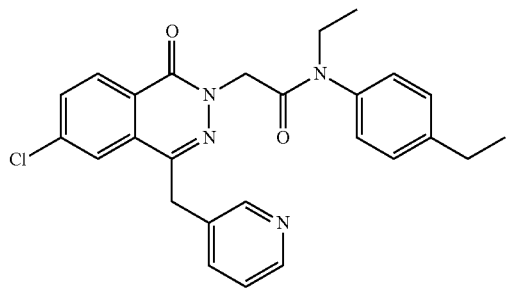 [SMILES: CCc1ccc(N(CC)C(=O)Cn2nc(Cc3cccnc3)c3cc(Cl)ccc3c2=O)cc1] | 2-(6-chloro-1-oxo-4-(pyridin-3-ylmethyl)phthalazin-2(1H)-yl)-N-ethyl-N-(4-ethylphenyl)acetamide | 461 [M + H] |
| 41. | 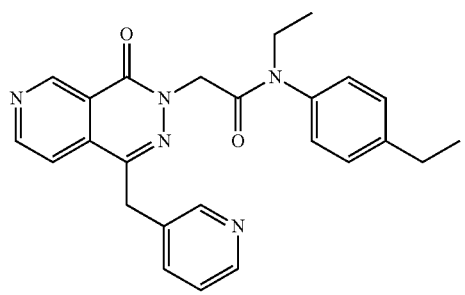 [SMILES: CCc1ccc(N(CC)C(=O)Cn2nc(Cc3cccnc3)c3ccncc3c2=O)cc1] | N-ethyl-N-(4-ethylphenyl)-2-(4-oxo-1-(pyridin-3-ylmethyl)pyrido[3,4-d]pyridazin-3(4H)-yl)acetamide | 428 [M + H] |
| 42. | 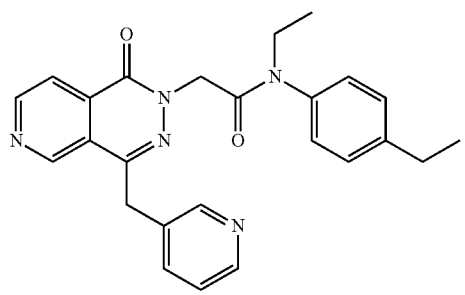 [SMILES: CCc1ccc(N(CC)C(=O)Cn2nc(Cc3cccnc3)c3cnccc3c2=O)cc1] | N-ethyl-N-(4-ethylphenyl)-2-(1-oxo-4-(pyridin-3-ylmethyl)pyrido[3,4-d]pyridazin-2(1H)-yl)acetamide | 428 [M + H] |
| 43. | 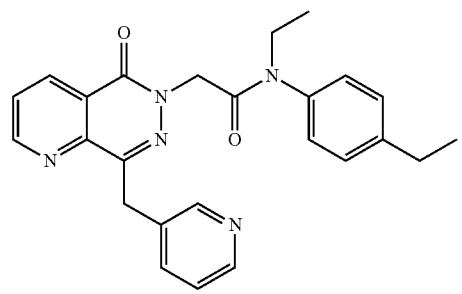 [SMILES: CCc1ccc(N(CC)C(=O)Cn2nc(Cc3cccnc3)c3ncccc3c2=O)cc1] | N-ethyl-N-(4-ethylphenyl)-2-(5-oxo-8-(pyridin-3-ylmethyl)pyrido[2,3-d]pyridazin-6(5H)-yl)acetamide | 428 [M + H] |
| 44. | 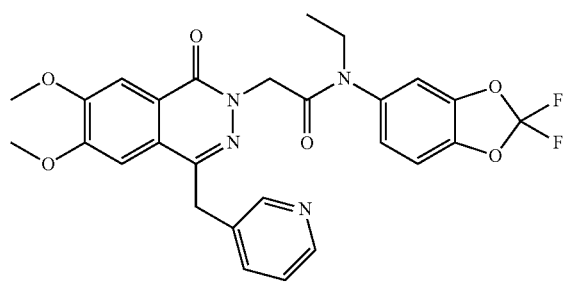 [SMILES: CCN(C(=O)Cn1nc(Cc2cccnc2)c2cc(OC)c(OC)cc2c1=O)c1ccc2c(c1)OC(F)(F)O2] | N-(2,2-difluorobenzo[d][1,3]dioxol-5-2-(6,7-dimethoxy-1-oxo-4-(pyridin-3-ylmethyl)phthalazin-2(1H)-yl)-N-ethylacetamide | 539 [M + H] |

-continued

| Example No. | Structure | IUPAC Name | LCMS m/z |
|---|---|---|---|
| 45. | 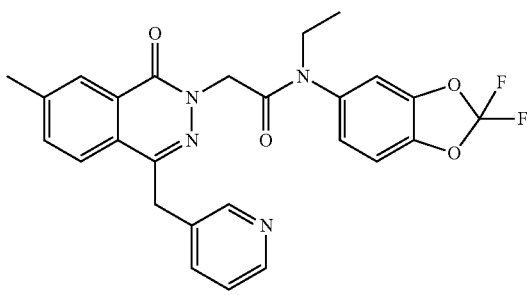 [SMILES: CCN(C(=O)Cn1nc(Cc2cccnc2)c2ccc(C)cc2c1=O)c1ccc2c(c1)OC(F)(F)O2] | N-(2,2-difluorobenzo[d][1,3]dioxol-5-yl)-N-ethyl-2-(7-methyl-1-oxo-4-(pyridin-3-ylmethyl)phthalazin-2(1H)-yl)acetamide | 493 [M + H] |
| 46. | 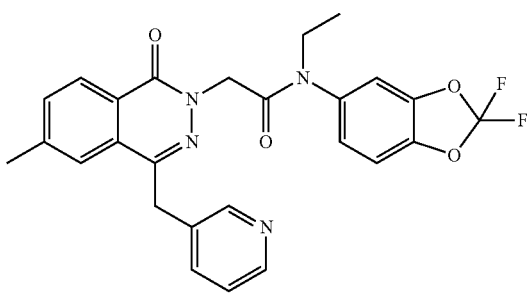 [SMILES: CCN(C(=O)Cn1nc(Cc2cccnc2)c2cc(C)ccc2c1=O)c1ccc2c(c1)OC(F)(F)O2] | N-(2,2-difluorobenzo[d][1,3]dioxol-5-yl)-N-ethyl-2-(6-methyl-1-oxo-4-(pyridin-3-ylmethyl)phthalazin-2(1H)-yl)acetamide | 493 [M + H] |
| 47. | 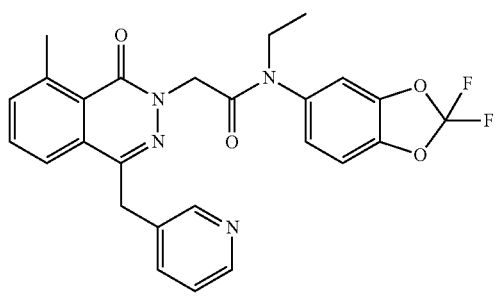 [SMILES: CCN(C(=O)Cn1nc(Cc2cccnc2)c2cccc(C)c2c1=O)c1ccc2c(c1)OC(F)(F)O2] | N-(2,2-difluorobenzo[d][1,3]dioxol-5-yl)-N-ethyl-2-(8-methyl-1-oxo-4-(pyridin-3-ylmethyl)phthalazin-2(1H)-yl)acetamide | 493 [M + H] |
| 48. | 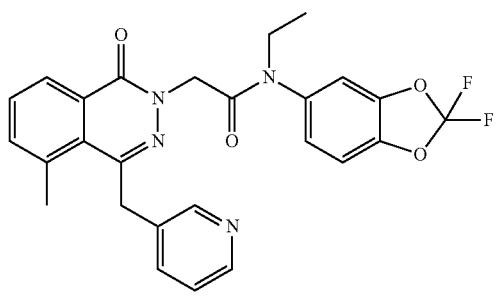 [SMILES: CCN(C(=O)Cn1nc(Cc2cccnc2)c2c(C)cccc2c1=O)c1ccc2c(c1)OC(F)(F)O2] | N-(2,2-difluorobenzo[d][1,3]dioxol-5-yl)-N-ethyl-2-(5-methyl-1-oxo-4-(pyridin-3-ylmethyl)phthalazin-2(1H)-yl)acetamide | 493 [M + H] |
| 49. | 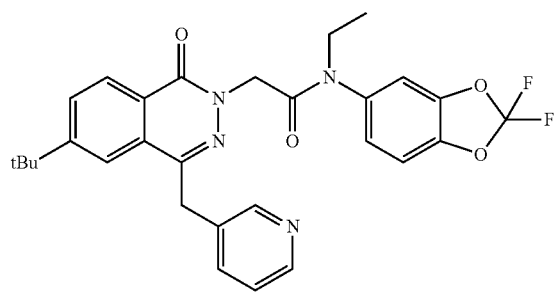 [SMILES: CCN(C(=O)Cn1nc(Cc2cccnc2)c2cc(C(C)(C)C)ccc2c1=O)c1ccc2c(c1)OC(F)(F)O2] | 2-(6-(tert-butyl)-1-oxo-4-(pyridin-3-ylmethyl)phthalazin-2(1H)-yl)-N-(2,2-difluorobenzo[d][1,3]dioxol-5-yl)-N-ethylacetamide | 535 [M + H] |

-continued

| Example No. | Structure | IUPAC Name | LCMS m/z |
|---|---|---|---|
| 50. | 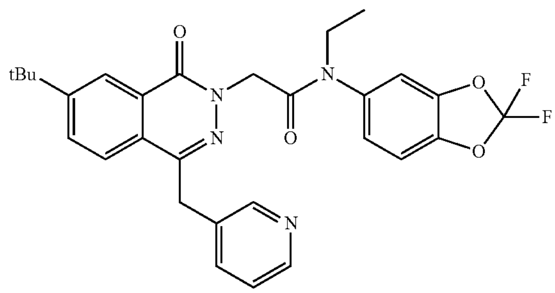 [SMILES: CCN(C(=O)Cn1nc(Cc2cccnc2)c2ccc(C(C)(C)C)cc2c1=O)c1ccc2c(c1)OC(F)(F)O2] | 2-(7-(tert-butyl)-1-oxo-4-(pyridin-3-ylmethyl)phthalazin-2(1H)-yl)-N-(2,2-difluorobenzo[d][1,3]dioxol-5-yl)-N-ethylacetamide | 535 [M + H] |
| 51. | 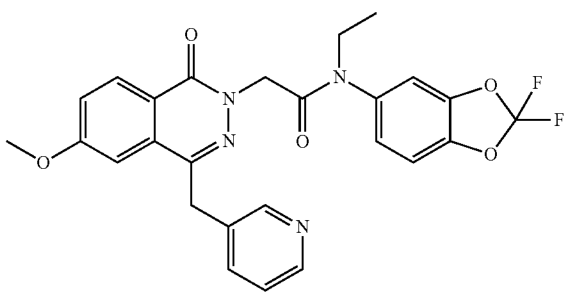 [SMILES: CCN(C(=O)Cn1nc(Cc2cccnc2)c2cc(OC)ccc2c1=O)c1ccc2c(c1)OC(F)(F)O2] | N-(2,2-difluorobenzo[d][1,3]dioxol-5-yl)-N-ethyl-2-(6-methoxy-1-oxo-4-(pyridin-3-ylmethyl)phthalazin-2(1H)-yl)acetamide | 509 [M + H] |
| 52. | 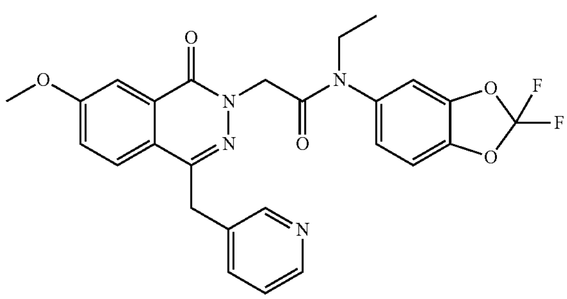 [SMILES: CCN(C(=O)Cn1nc(Cc2cccnc2)c2ccc(OC)cc2c1=O)c1ccc2c(c1)OC(F)(F)O2] | N-(2,2-difluorobenzo[d][1,3]dioxol-5-yl)-N-ethyl-2-(7-methoxy-1-oxo-4-(pyridin-3-ylmethyl)phthalazin-2(1H)-yl)acetamide | 509 [M + H] |
| 53. | 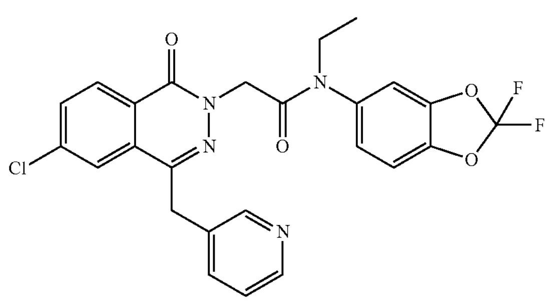 [SMILES: CCN(C(=O)Cn1nc(Cc2cccnc2)c2cc(Cl)ccc2c1=O)c1ccc2c(c1)OC(F)(F)O2] | 2-(6-chloro-1-oxo-4-(pyridin-3-ylmethyl)phthalazin-2(1H)-yl)-N-(2,2-difluorobenzo[d][1,3]dioxol-5-yl)-N-ethylacetamide | 513 [M + H] |
| 54. | 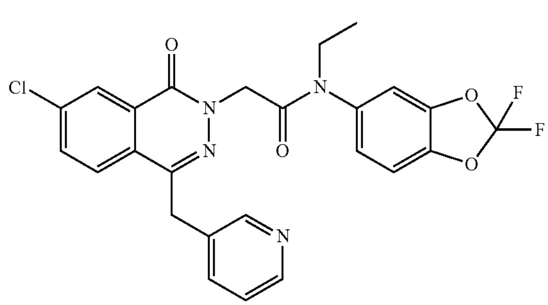 [SMILES: CCN(C(=O)Cn1nc(Cc2cccnc2)c2ccc(Cl)cc2c1=O)c1ccc2c(c1)OC(F)(F)O2] | 2-(7-chloro-1-oxo-4-(pyridin-3-ylmethyl)phthalazin-2(1H)-yl)-N-(2,2-difluorobenzo[d][1,3]dioxol-5-yl)-N-ethylacetamide | 513 [M + H] |

| Example No. | Structure | IUPAC Name | LCMS m/z |
|---|---|---|---|
| 55. | 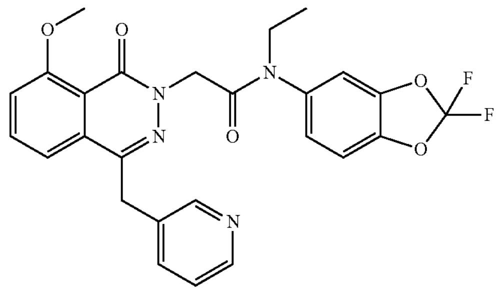 [SMILES: CCN(C(=O)Cn1nc(Cc2cccnc2)c2cccc(OC)c2c1=O)c1ccc2c(c1)OC(F)(F)O2] | N-(2,2-difluorobenzo[d][1,3]dioxol-5-yl)-N-ethyl-2-(8-methoxy-1-oxo-4-(pyridin-3-ylmethyl)phthalazin-2(1H)-yl)acetamide | 509 [M + H] |
| 56. | 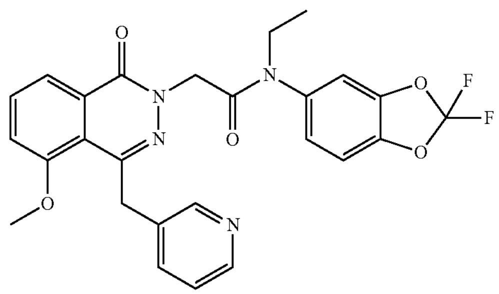 [SMILES: CCN(C(=O)Cn1nc(Cc2cccnc2)c2c(OC)cccc2c1=O)c1ccc2c(c1)OC(F)(F)O2] | N-(2,2-difluorobenzo[d][1,3]dioxol-5-yl)-N-ethyl-2-(5-methoxy-1-oxo-4-(pyridin-3-ylmethyl)phthalazin-2(1H)-yl)acetamide | 509 [M + H] |
| 57. | 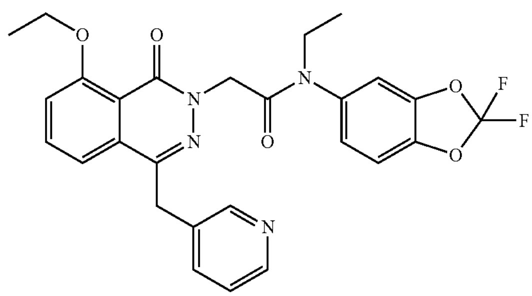 [SMILES: CCOc1cccc2c(Cc3cccnc3)nn(CC(=O)N(CC)c3ccc4c(c3)OC(F)(F)O4)c(=O)c12] | N-(2,2-difluorobenzo[d][1,3]dioxol-5-yl)-N-ethyl-2-(8-ethoxy-1-oxo-4-(pyridin-3-ylmethyl)phthalazin-2(1H)-yl)acetamide | 523 [M + H] |
| 58. | 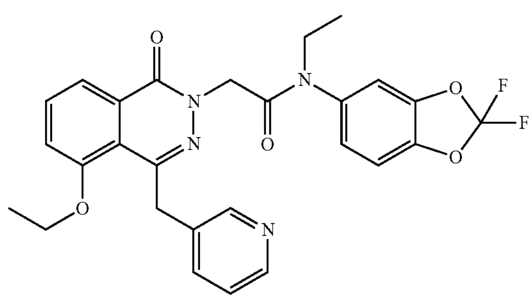 [SMILES: CCOc1cccc2c(=O)n(CC(=O)N(CC)c3ccc4c(c3)OC(F)(F)O4)nc(Cc3cccnc3)c12] | N-(2,2-difluorobenzo[d][1,3]dioxol-5-yl)-N-ethyl-2-(5-ethoxy-1-oxo-4-(pyridin-3-ylmethyl)phthalazin-2(1H)-yl)acetamide | 523 [M + H] |
| 59. | 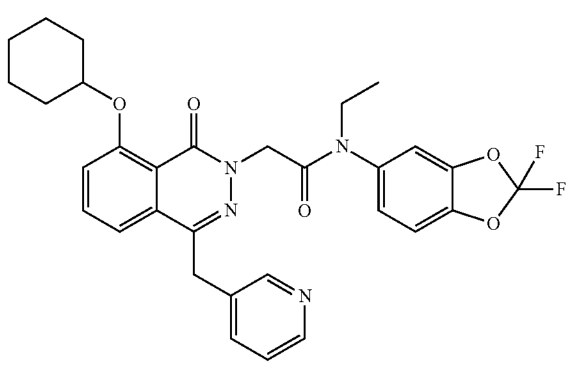 [SMILES: CCN(C(=O)Cn1nc(Cc2cccnc2)c2cccc(OC3CCCCC3)c2c1=O)c1ccc2c(c1)OC(F)(F)O2] | 2-(8-(cyclohexyloxy)-1-oxo-4-(pyridin-3-ylmethyl)phthalazin-2(1H)-yl)-N-(2,2-difluorobenzo[d][1,3]dioxol-5-yl)-N-ethylacetamide | 577 [M + H] |

| Example No. | Structure | IUPAC Name | LCMS m/z |
|---|---|---|---|
| 60. | 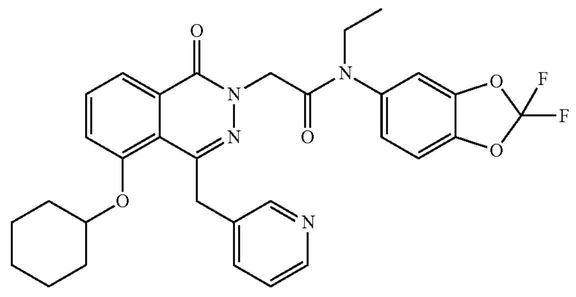 [SMILES: CCN(C(=O)Cn1nc(Cc2cccnc2)c2c(OC3CCCCC3)cccc2c1=O)c1ccc2c(c1)OC(F)(F)O2] | 2-(5-(cyclohexyloxy)-1-oxo-4-(pyridin-3-ylmethyl)phthalazin-2(1H)-yl)-N-(2,2-difluorobenzo[d][1,3]dioxol-5-yl)-N-ethylacetamide | 577 [M + H] |
| 61. | 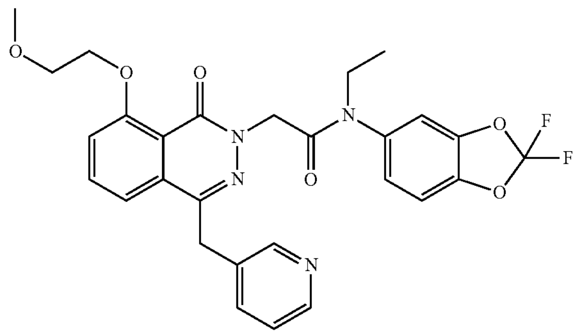 [SMILES: CCN(C(=O)Cn1nc(Cc2cccnc2)c2cccc(OCCOC)c2c1=O)c1ccc2c(c1)OC(F)(F)O2] | N-(2,2-difluorobenzo[d][1,3]dioxol-5-yl)-N-ethyl-2-(8-(2-methoxyethoxy)-1-oxo-4-(pyridin-3-ylmethyl)phthalazin-2(1H)-yl)acetamide | 553 [M + H] |
| 62. | 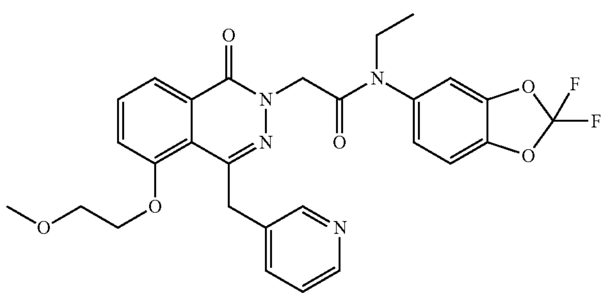 [SMILES: CCN(C(=O)Cn1nc(Cc2cccnc2)c2c(OCCOC)cccc2c1=O)c1ccc2c(c1)OC(F)(F)O2] | N-(2,2-difluorobenzo[d][1,3]dioxol-5-yl)-N-ethyl-2-(5-(2-methoxyethoxy)-1-oxo-4-(pyridin-3-ylmethyl)phthalazin-2(1H)-yl)acetamide | 553 [M + H] |

4-hydroxyisobenzofuran-1(3H)-one

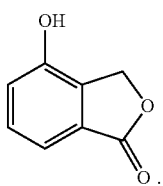 [SMILES: O=C1OCc2c(O)cccc21]

To a stirred solution of 3-hydroxy benzoic acid (1.0 g, 7.24 mmol) in 40% formaldehyde (20 mL) was added conc. hydrochloric acid (20 mL) and conc. sulphuric acid (1 mL) at rt. The mixture was stirred at rt for 16 hr. The reaction mixture was concentrated and quenched with saturated solution of ammonium chloride (50 mL) and extracted with EtOAc (25 mL×2). The organic layer was washed with brine, dried over sodium sulfate, and concentrated. The crude product was purified by silica gel chromatography (0-25% EtOAc/hexane) to give 6-hydroxyisobenzofuran-1(3H)-one (0.850 g, 151 [M+H]). $^1$H NMR (400 MHz, DMSO) δ: 5.312 (s, 2H), 7.283-7.301 (d, J=7.2, 1H), 7.397-7.435 (t, 1H), 7.465-7.487 (dd, J=4.0, 1H), 10.254 (s, 1H).

4-methoxyisobenzofuran-1(3H)-one and 7-methoxyisobenzofuran-1(3H)-one

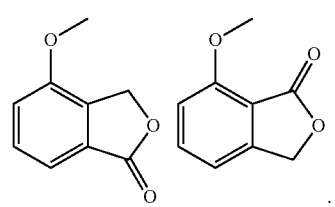

To a stirred solution of 6-hydroxyisobenzofuran-1(3H)-one (4.0 g, 26.0 mmol) in acetone (40 mL) was added $K_2CO_3$ (14.7 g, 106.6 mmol) was added at rt. The mixture was stirred at rt under nitrogen for 30 min, then dimethyl sulfate (11 mL, 106.6 mmol) was added and reaction mixture was stirred at rt for 16 h. The reaction mixture was concentrated and quenched with saturated solution of ammonium chloride (500 mL) and extracted with EtOAc (50 mL×2). The organic layer was washed with brine, dried over sodium sulfate, and concentrated. The crude product was purified by silica gel chromatography (0-60% EtOAc/hexane) to give a ~1:1 isomeric mixture by LCMS analysis of 4-methoxyisobenzofuran-1(3H)-one and 7-methoxyisobenzofuran-1(3H)-one (3.5 g, LCMS: $R_T$ 1.283 min and 1.383 min at 214 nM, 165 [M+H]).

4-ethoxyisobenzofuran-1(3H)-one

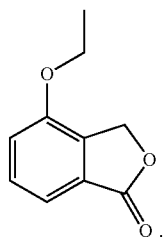

To a stirred solution of 6-hydroxyisobenzofuran-1(3H)-one (4.0 g, 26.0 mmol) in acetone (40 mL) was added $K_2CO_3$ (14.7 g, 106.6 mmol) at rt. The mixture was stirred at rt under nitrogen for 30 min, then diethylsulfate (14 mL, 106.6 mmol) was added and reaction mixture was stirred at rt for 16 h. Reaction mixture was concentrated and quenched with saturated solution of ammonium chloride (500 mL) and extracted with EtOAc (50 mL×2). The organic layer was washed with brine, dried over sodium sulfate, and concentrated. The crude product was purified by silica gel chromatography (0-60% EtOAc/hexane) to give 4-ethoxyisobenzofuran-1(3H)-one (3.5 g, 179 [M+H]).

4-(cyclohexyloxy)isobenzofuran-1(3H)-one

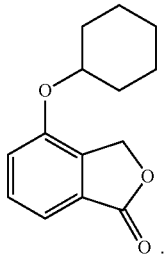 [SMILES: O=C1OCc2c(OC3CCCCC3)cccc21]

To a stirred solution of 6-hydroxyisobenzofuran-1(3H)-one (4.0 g, 26.6 mmol) in DMSO (30 mL) was added K-OtBu (8.9 g, 79.9 mmol) at rt and the mixture stirred for 30 min. Cyclohexyl bromide (20.0 mL, 159.9 mmol) was added and reaction mixture was stirred at 110° C. for 16 hr. The reaction mixture was concentrated and quenched with saturated solution of ammonium chloride (500 mL) and extracted with EtOAc (100 mL×2). The organic layer was washed with brine, dried over sodium sulfate, and concentrated. The crude product was purified by silica gel chromatography (0-5% EtOAc/hexane) to give 4-(cyclohexyloxy)isobenzofuran-1(3H)-one (2.0 g, 233 [M+H]).

4-(2-methoxyethoxy)isobenzofuran-1(3H)-one

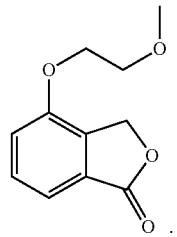

To a stirred solution of 6-hydroxyisobenzofuran-1(3H)-one (3.0 g, 20.0 mmol) in DMF (50 mL) was added NaH (1.44 g, 20.0 mmol) at rt. The mixture was stirred at rt for 30 min, then 2-bromo ethyl methyl ether (3.0 g, 20.0 mmol) was added and reaction mixture stirred at rt for 16 hr. The reaction mixture was concentrated and quenched with saturated solution of ammonium chloride (500 mL) and extracted with EtOAc (100 mL×2). The organic layer was washed with brine, dried over sodium sulfate, and concentrated. The crude product was purified by silica gel chromatography (0-20% EtOAc/hexane) to give 4-(2-methoxyethoxy)isobenzofuran-1(3H)-one (3.2 g, 209 [M+H]).

Example 63: Synthesis of 2-(4-(3-cyanophenyl)-7-methoxy-1-oxophthalazin-2(1H)-yl)-N-(2,2-difluorobenzo[d][1,3]dioxol-5-yl)-N-methylacetamide

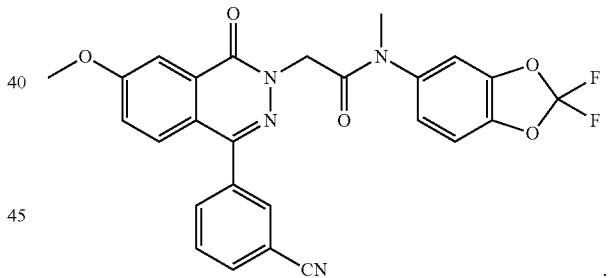

3-cyano-N-methoxy-N-methylbenzamide

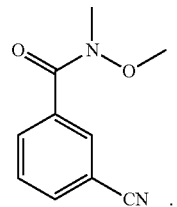

To a 0° C., stirred solution of 3-cyano benzoic acid (5.0 g, 33.9 mmol) in DMF (30 mL) was added triethylamine (14.8 mL, 101.7 mmol) and EDC.HCl (9.77 g, 12.24 mmol). The mixture was stirred at rt for 30 minutes. The reaction was cooled back to 0° C., N—O-dimethylhydroxylamine. HCl (4.97 g, 50.98 mmol) was added and the mixture stirred at rt for 16 hr. The reaction was quenched with water (300 mL) and extracted with EtOAc (100 mL×2). The organic layers was washed with brine, dried over sodium sulfate, and concentrated. The crude product was purified by silica gel chromatography (0-25% EtOAc/hexane) to give 3-cyano-N-methoxy-N-methylbenzamide (3.2 g, 191 [M+H]). $^1$H NMR: (400 MHz, DMSO) δ: 3.286 (s, 3H), 3.550 (s, 3H), 7.659-7.699 (t, 1H), 7.896-7.903 (d, J=2.4, 1H), 7.961-7.975 (d, J=5.6, 1H), 8.037 (s, 1H).

2-(3-cyanobenzoyl)-5-methoxybenzoic acid

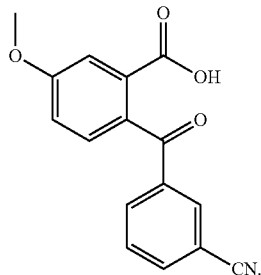 [SMILES: COc1ccc(C(=O)c2cccc(C#N)c2)c(C(=O)O)c1]

To a solution of 2-bromo-5-methoxybenzoic acid (3.69 g, 15.0 mmol) in THF (15 mL) was added n-BuLi ((1.6M in hexane, 21 mL, 33.6 mmol) dropwise at −78° C. The reaction mixture was stirred for 1 hr at −78° C. and then a solution of 3-cyano-N-methoxy-N-methylbenzamide (3.2 g, 16.8 mmol) in THF (15 mL) was added dropwise at −78° C. The reaction was stirred for 1 hr at −78° C. and then for 16 hr at rt. The reaction mixture was diluted with water (30 mL) and acidified with 5N HCl solution (10 mL) and extracted with EtOAc (100 mL×2). The organic layer was washed with brine, dried over sodium sulfate, and concentrated to obtain 2-(3-cynobenzoyl)-5-methoxybenzoic acid (3.8 g, 282 [M+H]). $^1$H NMR: (400 MHz, DMSO) δ: 3.924 (s, 3H), 7.311-7.324 (t, 2H), 7.439-7.451 (t, 2H), 7.560 (s, 1H), 7.716-7.720 (d, J=1.6, 1H), 8.100-8.103 (d, J=1.2, 1H), 12.703 (s, 1H).

3-(6-methoxy-4-oxo-3,4-dihydrophthalazin-1-yl)benzonitrile

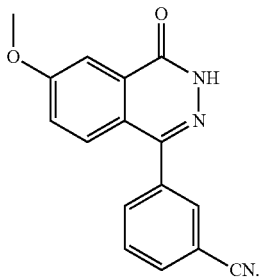 [SMILES: COc1ccc2c(-c3cccc(C#N)c3)n[nH]c(=O)c2c1]

A solution of 2-(3-cyanobenzoyl)-5-methoxybenzoic acid (4.0 g, 14.2 mmol) in hydrazine hydrate (8 mL) and EtOH (40 mL) was heated at 110° C. for 2 hr. The reaction mixture was diluted with water (100 mL) and the precipitated solid was filtered and dried to obtained 3-(6-methoxy-4-oxo-3,4-dihydrophthalazin-1-yl)benzonitrile (1.1 g, 278 [M+H]) as a white solid. $^1$H NMR: (400 MHz, DMSO) δ: 3.967 (s, 3H), 7.287-7.333 (dd, J=2.0 1H), 7.600-7.622 (d, J=8.8, 1H), 7.739-7.788 (m, 2H), 7.927-7.947 (d, J=8.0, 1H), 8.012-8.032 (d, J=8.0, 1H), 8.071 (s, 1H), 12.835 (s, 1H).

2,2-difluoro-N-methylbenzo[d][1,3]dioxol-5-amine

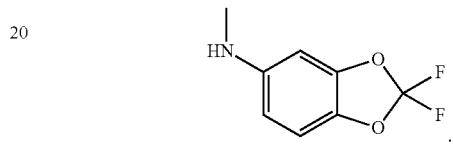

To a solution of 2,2-difluoro-5-aminobenzo[d][1,3]dioxole (2.0 g, 11.5 mmol) in DMF (15 mL) was added K$_2$CO$_3$ (4.7 g, 11.5 mmol) at rt and the reaction mixture stirred for 1 hr. Methyl iodide (0.72 mL, 0.011 mmol) was then added dropwise to at 0° C. and the reaction stirred for 16 hr at rt. The reaction mixture was diluted with water (50 mL) and the product extracted in EtOAc (100 mL×2). The extract was washed with brine, dried over anhydrous sodium sulfate and concentrated to obtain a residue which was purified by silica gel (60-120 mesh) column chromatography (0-10% EtOAc/hexane) to give N-methyl-2,2-difluorobenzo[d][1,3]dioxol-5-amine (1.416 g, 188 [M+H]).

2-bromo-N-(2,2-difluorobenzo[d][1,3]dioxol-5-yl)-N-methylacetamide

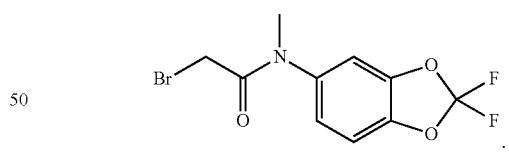

To a stirred solution of N-methyl-2,2-difluorobenzo[d][1,3]dioxol-5-amine (1.0 g, 5.3 mmol) in DCM (30 mL) was added 2-bromoacetic acid (1.70 g, 12.2 mmol), EDC.HCL (2.45 g, 12.3 mmol) and DMAP (32 mg, 0.26 mmol) under N$_2$. The reaction was stirred for 16 h at rt and then diluted with water (100 mL). The product was extracted in DCM (100 mL×3), washed with brine, dried over anhydrous sodium sulfate and concentrated to obtain a residue which was purified by chromatography (0-7% EtOAc/hexane) to give 2-bromo-N-(2,2-difluorobenzo[d][1,3]dioxol-5-yl)-N-methylacetamide (1.1 g, 310 [M+H]), $^1$H NMR: (400 MHz, DMSO) δ: 3.286 (s, 3H), 4.222 (s, 2H), 7.304 (s, 1H) 7.496-7.517 (d, J=8.4, 1H), 7.613 (s, 1H).

2-(4-(3-cyanophenyl)-7-methoxy-1-oxophthalazin-2(1H)-yl)-N-(2,2-difluorobenzo[d][1,3]dioxol-5-yl)-N-methylacetamide

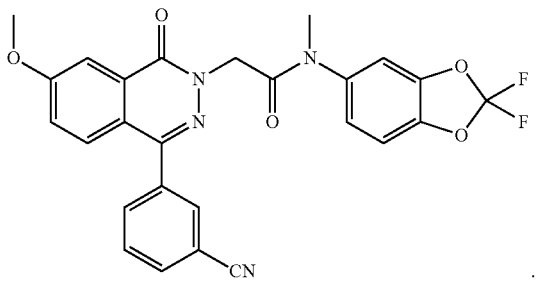 [SMILES: COc1ccc2c(-c3cccc(C#N)c3)nn(CC(=O)N(C)c3ccc4c(c3)OC(F)(F)O4)c(=O)c2c1]

To a solution of 3-(6-methoxy-4-oxo-3,4-dihydrophthalazin-1-yl)benzonitrile (0.1 g, 0.36 mmol) in DMF (10 mL) was added NaH (0.021 g, 0.36 mmol) portionwise at 0° C. The reaction mixture was stirred for 30 min at 0° C. 2-Bromo-N-(2,2-difluorobenzo[d][1,3]dioxol-5-yl-N-methylacetamide (0.111 g, 0.54 mmol) in DMF (2 mL) was added dropwise at 0° C. and the reaction stirred for 16 hr at rt. The reaction mixture was diluted with satd ammonium chloride solution (25 mL) and extracted with EtOAc (25 mL×2). The extract was washed with brine (50 mL), dried over anhydrous sodium sulfate and concentrated to give crude which was purified by column chromatography (0-10% EtOAc/DCM) to obtain 2-(4(3-cyanophenyl)-7-methoxy-1-oxophthalazine-2(1H)-yl)-N-(2,2-difluorobenzo[d][1,3]dioxol-5-yl)-N-methylacetamide (0.045 g, 505 [M+H]) as white solid. $^1$H NMR: (400 MHz, DMSO) δ: 3.193 (s, 3H), 3.967 (s, 3H), 4.779 (s, 2H), 7.347-7.366 (d, J=7.6, 1H), 7.490-7.527 (m, 2H), 7.648-7.698 (t, 3H), 7.766-7.806 (t, 1H), 7.917-7.937 (d, J=8.0, 1H), 8.035-8.058 (m, 2H).

Representative compounds of the invention were prepared in a similar manner to example 57 from the corresponding benzoic acid and the appropriate alkylating agent (scheme 4).

| Example No. | Structure | IUPAC Name | LCMS m/z |
|---|---|---|---|
| 64. | 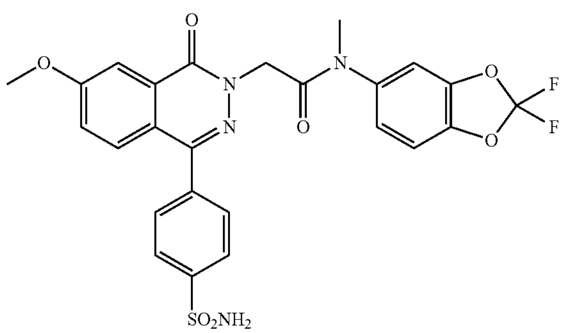 [SMILES: COc1ccc2c(-c3ccc(S(N)(=O)=O)cc3)nn(CC(=O)N(C)c3ccc4c(c3)OC(F)(F)O4)c(=O)c2c1] | N-(2,2-difluorobenzo[d][1,3]dioxol-5-yl)-2-(7-methoxy-1-oxo-4-(4-sulfamoylphenyl)phthalazin-2(1H)-yl)-N-methylacetamide | 559 [M + H] |
| 65. | 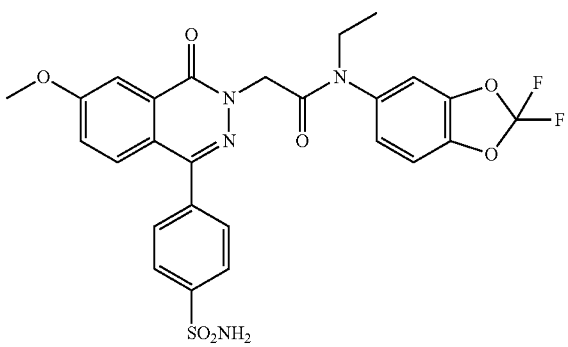 [SMILES: CCN(C(=O)Cn1nc(-c2ccc(S(N)(=O)=O)cc2)c2ccc(OC)cc2c1=O)c1ccc2c(c1)OC(F)(F)O2] | N-(2,2-difluorobenzo[d][1,3]dioxol-5-yl)-N-ethyl-2-(7-methoxy-1-oxo-4-(4-sulfamoylphenyl)phthalazin-2(1H)-yl)acetamide | 573 [M + H] |
| 66. | 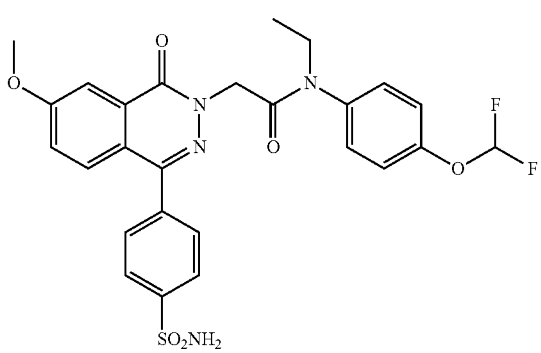 [SMILES: CCN(C(=O)Cn1nc(-c2ccc(S(N)(=O)=O)cc2)c2ccc(OC)cc2c1=O)c1ccc(OC(F)F)cc1] | N-(4-(difluoromethoxy)phenyl)-N-ethyl-2-(7-methoxy-1-oxo-4-(4-sulfamoylphenyl)phthalazin-2(1H)-yl)acetamide | 559 [M + H] |

-continued

| Example No. | Structure | IUPAC Name | LCMS m/z |
|---|---|---|---|
| 67. | 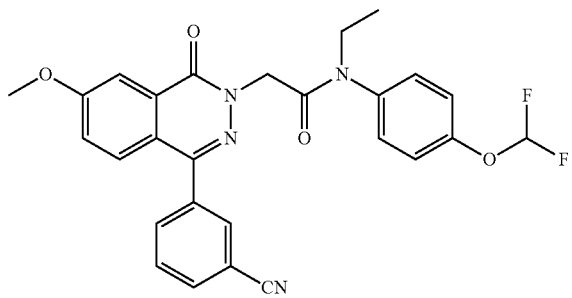 [SMILES: CCN(C(=O)Cn1nc(-c2cccc(C#N)c2)c2ccc(OC)cc2c1=O)c1ccc(OC(F)F)cc1] | 2-(4-(3-cyanophenyl)-7-methoxy-1-oxophthalazin-2(1H)-yl)-N-(4-(difluoromethoxy)phenyl)-N-ethylacetamide | 505 [M + H] |
| 68. | 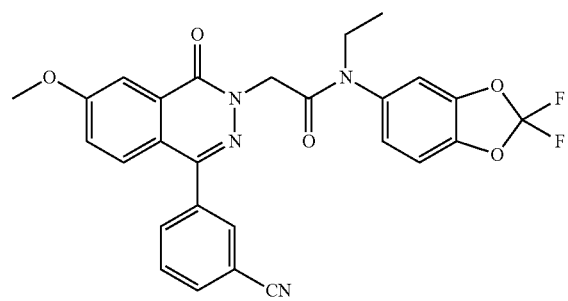 [SMILES: CCN(C(=O)Cn1nc(-c2cccc(C#N)c2)c2ccc(OC)cc2c1=O)c1ccc2c(c1)OC(F)(F)O2] | 2-(4-(3-cyanophenyl)-7-methoxy-1-oxophthalazin-2(1H)-yl)-N-(2,2-difluorobenzo[d][1,3]dioxol-5-yl)-N-ethylacetamide | 519 [M + H] |
| 69. | 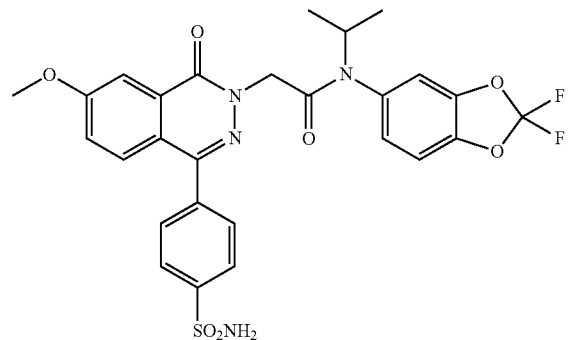 [SMILES: COc1ccc2c(-c3ccc(S(N)(=O)=O)cc3)nn(CC(=O)N(c3ccc4c(c3)OC(F)(F)O4)C(C)C)c(=O)c2c1] | N-(2,2-difluorobenzo[d][1,3]dioxol-5-yl)-N-isopropyl-2-(7-methoxy-1-oxo-4-(4-sulfamoylphenyl)phthalazin-2(1H)-yl)acetamide | 587 [M + H] |
| 70. | 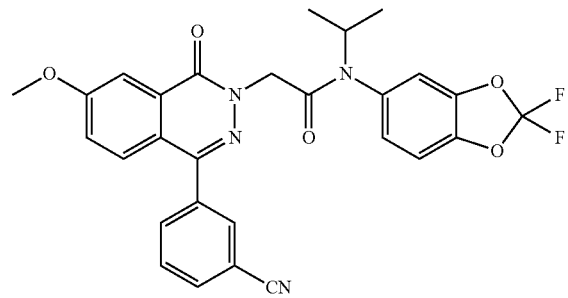 | 2-(4-(3-cyanophenyl)-7-methoxy-1-oxophthalazin-2(1H)-yl)-N-(2,2-difluorobenzo[d][1,3]dioxol-5-yl)-N-isopropylacetamide | 533 [M + H] |

| Example No. | Structure | IUPAC Name | LCMS m/z |
|---|---|---|---|
| 71. | 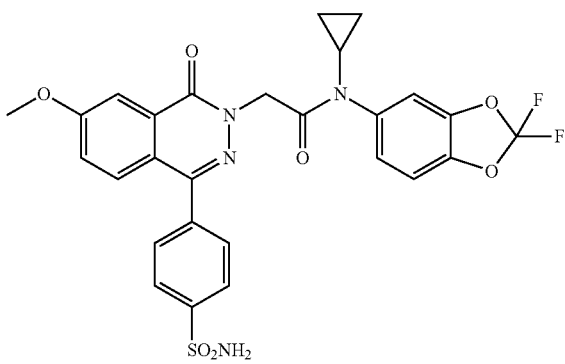 [SMILES: COc1ccc2c(-c3ccc(S(N)(=O)=O)cc3)nn(CC(=O)N(c3ccc4c(c3)OC(F)(F)O4)C3CC3)c(=O)c2c1] | N-cyclopropyl-N-(2,2-difluorobenzo[d][1,3]dioxol-5-yl)-2-(7-methoxy-1-oxo-4-(4-sulfamoylphenyl)phthalazin-2(1H)-yl)acetamide | 585 [M + H] |
| 72. | 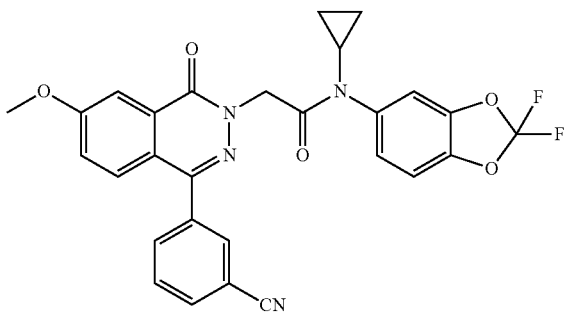 [SMILES: COc1ccc2c(-c3cccc(C#N)c3)nn(CC(=O)N(c3ccc4c(c3)OC(F)(F)O4)C3CC3)c(=O)c2c1] | 2-(4-(3-cyanophenyl)-7-methoxy-1-oxophthalazin-2(1H)-yl)-N-cyclopropyl-N-(2,2-difluorobenzo[d][1,3]dioxol-5-yl)acetamide | 531 [M + H] |
| 73. | 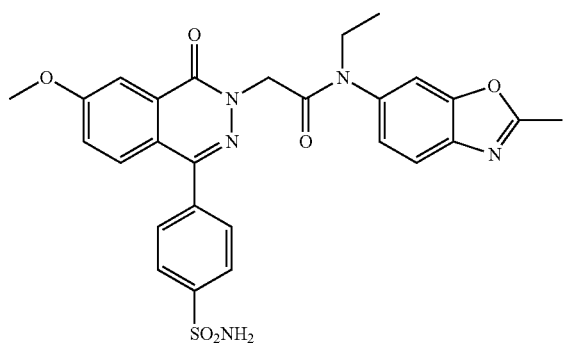 | N-ethyl-2-(7-methoxy-1-oxo-4-(4-sulfamoylphenyl)phthalazin-2(1H)-yl)-N-(2-methylbenzo[d]oxazol-6-yl)acetamide | 548 [M + H] |
| 74. | 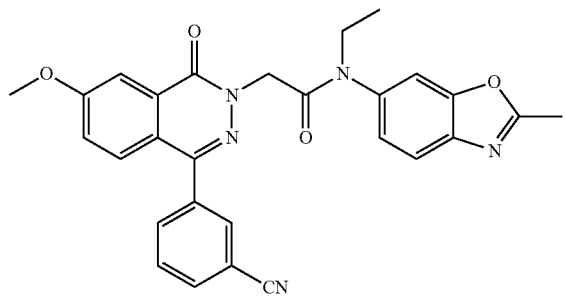 | 2-(4-(3-cyanophenyl)-7-methoxy-1-oxophthalazin-2(1H)-yl)-N-ethyl-N-(2-methylbenzo[d]oxazol-6-yl)acetamide | 494 [M + H] |

| Example No. | Structure | IUPAC Name | LCMS m/z |
|---|---|---|---|
| 75. | 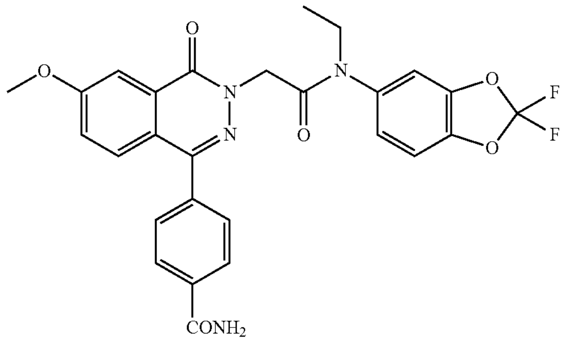 [SMILES: CCN(C(=O)Cn1nc(-c2ccc(C(N)=O)cc2)c2ccc(OC)cc2c1=O)c1ccc2c(c1)OC(F)(F)O2] | 4-(3-(2-((2,2-difluorobenzo[d][1,3]dioxol-5-yl)(ethyl)amino)-2-oxoethyl)-6-methoxy-4-oxo-3,4-dihydrophthalazin-1-yl)benzamide | 537 [M + H] |
| 76. | 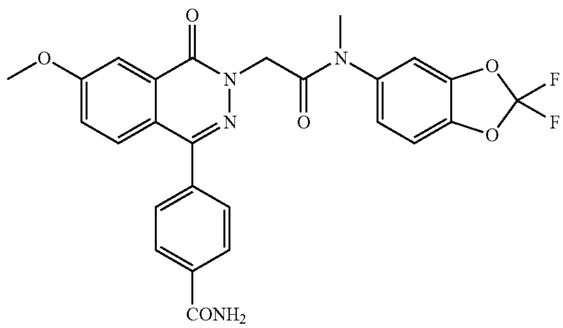 [SMILES: COc1ccc2c(-c3ccc(C(N)=O)cc3)nn(CC(=O)N(C)c3ccc4c(c3)OC(F)(F)O4)c(=O)c2c1] | 4-(3-(2-((2,2-difluorobenzo[d][1,3]dioxol-5-yl)(methyl)amino)-2-oxoethyl)-6-methoxy-4-oxo-3,4-dihydrophthalazin-1-yl)benzamide | 523 [M + H] |
| 77. | 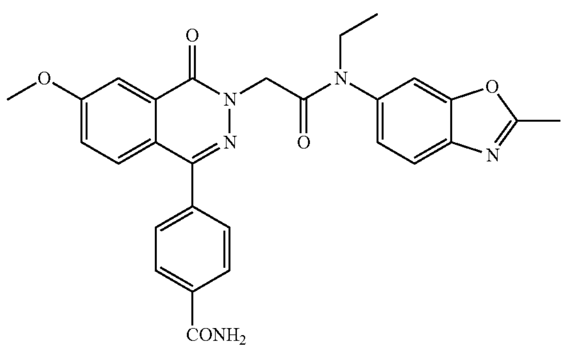 | 4-(3-(2-(ethyl(2-methylbenzo[d]oxazol-6-yl)amino)-2-oxoethyl)-6-methoxy-4-oxo-3,4-dihydrophthalazin-1-yl)benzamide | 512 [M + H] |

Example 78: Synthesis of N-(2-cyanophenyl)-3-(2-((2,2-difluorobenzo[d][1,3]dioxol-5-yl)(ethyl)amino)-2-oxoethyl)-4-oxo-3,4-dihydrophthalazine-1-carboxamide

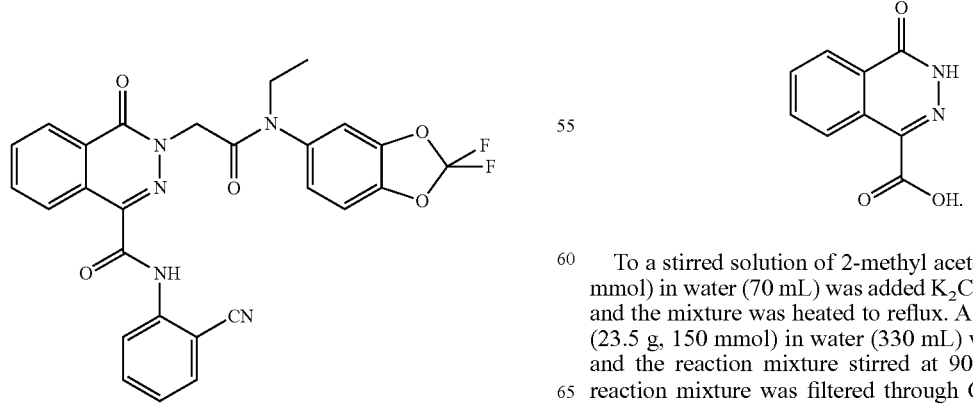

4-Oxo-3,4-dihydrophthalazine-1-carboxylic acid

To a stirred solution of 2-methyl acetophenone (5.0 g, 37 mmol) in water (70 mL) was added $K_2CO_3$ (3.0 g, 22 mmol) and the mixture was heated to reflux. A solution of $KMnO_4$ (23.5 g, 150 mmol) in water (330 mL) was added dropwise and the reaction mixture stirred at 90° C. for 16 h. The reaction mixture was filtered through Celite. The aqueous layer was distilled to half volume, the pH was adjusted by addition of 2N HCl (8 mL) to pH=8, and the reaction mixture was heated at 90° C. Hydrazine sulfate (4.8 g, 37 mmol) and NaOH (1.66 g, 41 mmol) were added and the heating was continued at 90° C. for 16 h. The reaction volume was reduced to half volume and solid was filtered. The aqueous layered was acidified with 2N HCl and the resulting white precipitate was filtered and dried to give 4-oxo-3,4-dihydrophthalazine-1-carboxylic acid (1.5 g). ¹H NMR: (400 MHz, DMSO) δ: 7.420-7.263 (m, 2H), 7.919-7.803 (m, 2H), 8.466 (s, 1H), 12.859 (s, 1H).

Ethyl 4-oxo-3,4-dihydrophthalazine-1-carboxylate

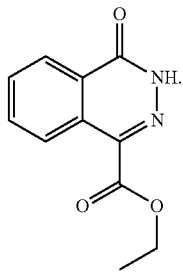 [SMILES: CCOC(=O)c1n[nH]c(=O)c2ccccc12]

To a solution of 4-oxo-3,4-dihydrophthalazine-1-carboxylic acid (16 g, 84.2 mmol) in EtOH was added conc.H₂SO₄ (40 mL) dropwise. The reaction was heated to 80° C. for 16 h. The EtOH was distilled off and water (200 mL) added. The solution was neutralized with sodium bicarbonate and then extracted with EtOAc (200 mL×3). The organic layer was dried over anhydrous Na₂SO₄ and concentrate to give ethyl 4-oxo-3,4-dihydrophthalazine-1-carboxylate (15 g, 219 [M+H]). ¹H NMR: (400 MHz, DMSO) δ: 1.377-1.353 (t, 3H), 4.426-4.373 (m, 2H), 7.930-7.889 (m, 1H), 8.021-7.979 (m, 1H), 8.313-8.289 (m, 1H), 8.536-8.511 (m, 1H), 13.188 (s, 1H).

Ethyl 3-(2-((2,2-difluorobenzo[d][1,3]dioxol-5-yl)(ethyl)amino)-2-oxoethyl)-4-oxo-3,4-dihydrophthalazine-1-carboxylate

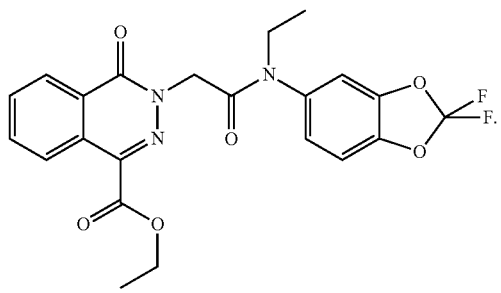 [SMILES: CCOC(=O)c1nn(CC(=O)N(CC)c2ccc3c(c2)OC(F)(F)O3)c(=O)c2ccccc12]

To a stirred solution of ethyl 4-oxo-3,4-dihydrophthalazine-1-carboxylate (2.0 g, 9.17 mmol) in THF (20 mL) was added NaH (60%, 0.403 g, 10.09 mmol) portion wise at 0° C. The reaction mixture was stirred for 30 min at 0° C., then 2-bromo-N-(2,2-difluorobenzo[d][1,3]dioxol-5-yl)-N-ethylacetamide (3.044 g, 9.17 mmol) was added and the mixture stirred for 16 hr at rt. The reaction mixture was diluted with water (100 mL) and extracted with EtOAc (3×25 mL). The organic layer was dried over Na₂SO₄ and concentrate to give ethyl 3-(2-((2,2-difluorobenzo[d][1,3]dioxol-5-yl)(ethyl)amino)-2-oxoethyl)-4-oxo-3,4-dihydrophthalazine-1-carboxylate (3.4 g, 460). ¹H NMR: (400 MHz, DMSO) δ: 1.215-1.157 (m, 3H), 1.384-1.281 (m, 3H), 4.055-4.002 (q, 2H), 4.451-4.398 (m, 2H), 4.704 (s, 2H), 7.373-7.347 (m, 2H), 7.561-7.492 (m, 2H), 7.692-7.687 (d, J=2 Hz, 1H), 7.995-7.909 (m, 1H), 8.034-8.012 (m, 1H), 8.287-8.8268 (d, J=7.6 Hz, 1H), 8.459-8.438 (d, J=8.4 Hz, 1H).

3-(2-((2,2-difluorobenzo[d][1,3]dioxol-5-yl)(ethyl)amino)-2-oxoethyl)-4-oxo-3,4-dihydrophthalazine-1-carboxylic acid

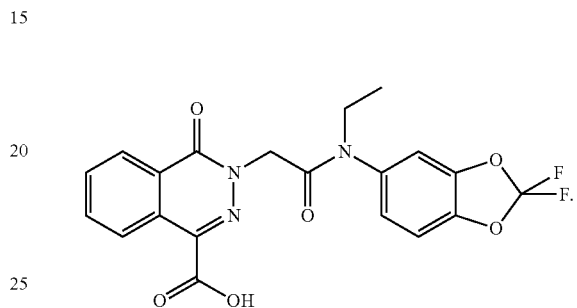

To a stirred solution of ethyl 3-(2-((2,2-difluorobenzo[d][1,3]dioxol-5-yl)(ethyl)amino)-2-oxoethyl)-4-oxo-3,4-dihydrophthalazine-1-carboxylate (3.4 g, 7.40 mmol) in THF (30 mL) was added a solution of NaOH (0.296 g, 29.6 mmol) in water (30 mL) dropwise at rt. The reaction mixture was stirred at rt for 16 hr, quenched with water (100 mL), neutralized with 2N HCl, and extracted with EtOAc (50 mL×3). The organic layer was dried over Na₂SO₄ and concentrated to give 3-(2-((2,2-difluorobenzo[d][1,3]dioxol-5-yl)(ethyl)amino)-2-oxoethyl)-4-oxo-3,4-dihydrophthalazine-1-carboxylic acid (2.0 g, 62.5%). ¹H NMR: (400 MHz, DMSO) δ: 1.109-1.075 (t, J=6.8 Hz, 3H), 3.708-3.624 (m, 2H), 4.702 (s, 2H), 7.252-7.233 (d, 1H, J=7.6 Hz), 7.363-7.310 (m, 1H), 7.565-7.497 (m, 1H), 8.027-7.903 (m, 2H), 8.283-8.264 (d, J=7.6 Hz, 1H), 8.551-8.531 (d, J=8 Hz, 1H).

N-(2-cyanophenyl)-3-(2-((2,2-difluorobenzo[d][1,3]dioxol-5-yl)(ethyl)amino)-2-oxoethyl)-4-oxo-3,4-dihydrophthalazine-1-carboxamide

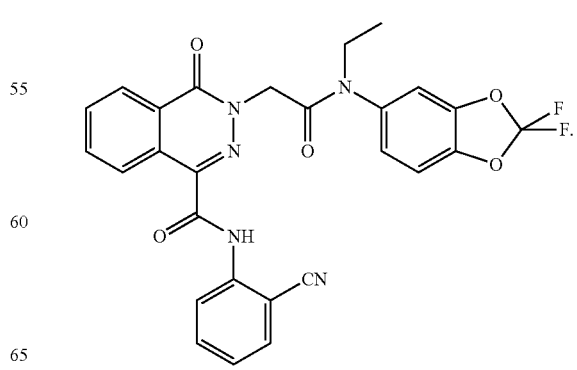

A solution of 3-(2-((2,2-difluorobenzo[d][1,3]dioxol-5-yl)(ethyl)amino)-2-oxoethyl)-4-oxo-3,4-dihydrophthalazine-1-carboxylic acid (0.150 g, 0.34 mmol) and 2-aminobenzonitrile (0.040 g, 0.34 mmol) in DCM (15 mL) was treated at 0° C. with pyridine (1.0 mL) and stirred for 15 min. POCl$_3$ (1.0 mL) was added dropwise and the reaction mixture stirred for 2 hr. The reaction was diluted with water (50 mL), neutralized with saturated sodium bicarbonate solution (10 mL), and then extracted in EtOAc (15 mL×3). The organic layer was dried over Na$_2$SO$_4$ to obtain crude product, which was purified by column chromatography (20-25% EtOAc/hexane) to give N-(2-cyanophenyl)-3-(2-(2,2-difluorobenzo[d][1,3]dioxol-5-yl)(ethyl)amino)-2-oxoethyl)-4-oxo-3,4-dihydrophthalazine-1-carboxamide (71 mg, 532 [M+H]). $^1$H NMR: (400 MHz, DMSO) δ: 1.033-1.069 (t, 3H), 3.684-3.737 (q, 2H), 4.767 (s, 2H), 7.369-7.390 (d, J=8.4 Hz, 1H), 7.460-7.501 (m, 1H), 7.571-7.593 (d, J=8.8 Hz, 1H), 7.700-7.749 (t, 2H), 7.786-7.825 (m, 1H), 7.931-8.058 (m, 3H), 8.318-8.338 (d, J=8 Hz, 1H), 8.714-8.735 (d, J=8.4 Hz, 1H), 10.825 (s, 1H).

Representative compounds of the invention were prepared in a similar manner to example 57 from the corresponding amine and the appropriate side-chain alkylation agent (scheme 6).

| Example No. | Structure | IUPAC Name | LCMS m/z |
|---|---|---|---|
| 79. | 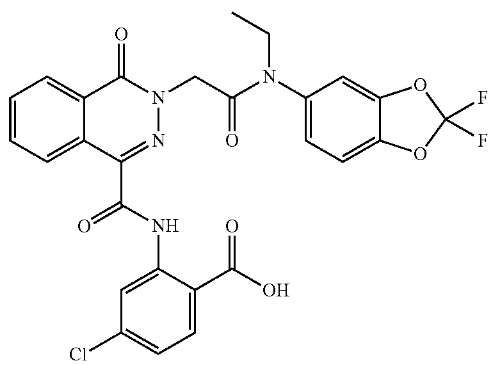 [SMILES: CCN(C(=O)Cn1nc(C(=O)Nc2cc(Cl)ccc2C(=O)O)c2ccccc2c1=O)c1ccc2c(c1)OC(F)(F)O2] | 4-chloro-2-(3-(2-((2,2-difluorobenzo[d][1,3]dioxol-5-yl)(ethyl)amino)-2-oxoethyl)-4-oxo-3,4-dihydrophthalazine-1-carboxamido)benzoic acid | 585 [M + H] |
| 80. | 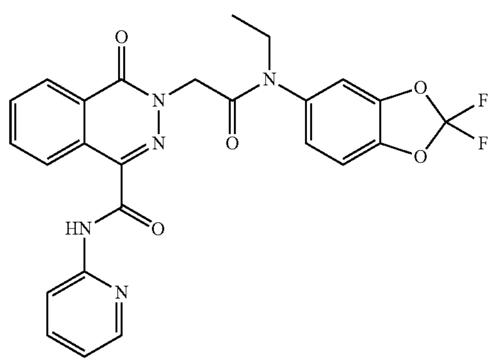 [SMILES: CCN(C(=O)Cn1nc(C(=O)Nc2ccccn2)c2ccccc2c1=O)c1ccc2c(c1)OC(F)(F)O2] | 3-(2-((2,2-difluorobenzo[d][1,3]dioxol-5-yl)(ethyl)amino)-2-oxoethyl)-4-oxo-N-(pyridin-2-yl)-3,4-dihydrophthalazine-1-carboxamide | 508 [M + H] |
| 81. | 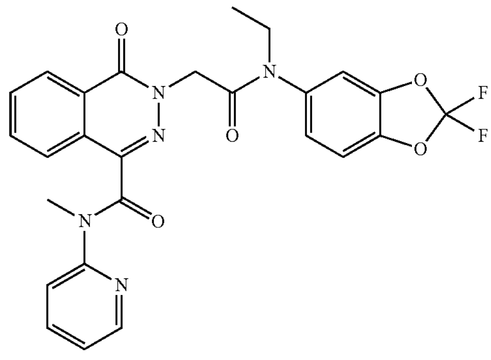 [SMILES: CCN(C(=O)Cn1nc(C(=O)N(C)c2ccccn2)c2ccccc2c1=O)c1ccc2c(c1)OC(F)(F)O2] | 3-(2-((2,2-difluorobenzo[d][1,3]dioxol-5-yl)(ethyl)amino)-2-oxoethyl)-N-methyl-4-oxo-N-(pyridin-2-yl)-3,4-dihydrophthalazine-1-carboxamide | 522 [M + H] |

-continued

| Example No. | Structure | IUPAC Name | LCMS m/z |
|---|---|---|---|
| 82. | 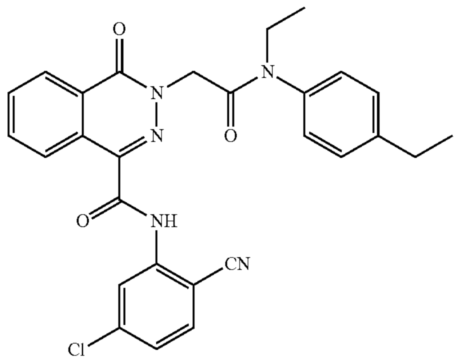 [SMILES: CCc1ccc(N(CC)C(=O)Cn2nc(C(=O)Nc3cc(Cl)ccc3C#N)c3ccccc3c2=O)cc1] | N-(5-chloro-2-cyanophenyl)-3-(2-(ethyl(4-ethylphenyl)amino)-2-oxoethyl)-4-oxo-3,4-dihydrophthalazine-1-carboxamide | 514 [M + H] |
| 83. | 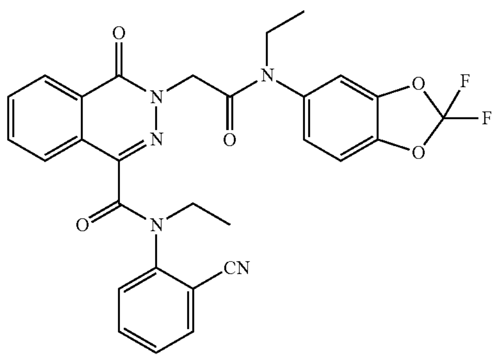 [SMILES: CCN(C(=O)Cn1nc(C(=O)N(CC)c2ccccc2C#N)c2ccccc2c1=O)c1ccc2c(c1)OC(F)(F)O2] | N-(2-cyanophenyl)-3-(2-((2,2-difluoro-benzo[d][1,3]dioxol-5-yl)(ethyl)amino)-2-oxoethyl)-N-ethyl-4-oxo-3,4-dihydrophthalazine-1-carboxamide | 560 [M + H] |
| 84. | 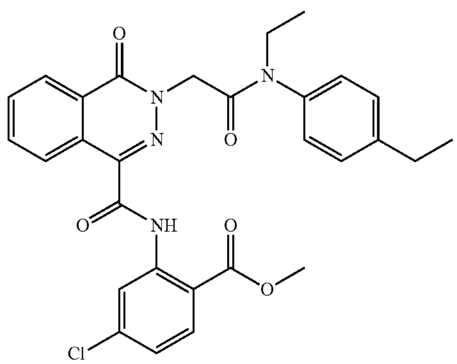 [SMILES: CCc1ccc(N(CC)C(=O)Cn2nc(C(=O)Nc3cc(Cl)ccc3C(=O)OC)c3ccccc3c2=O)cc1] | methyl 4-chloro-2-(3-(2-(ethyl(4-ethylphenyl)amino)-2-oxoethyl)-4-oxo-3,4-dihydrophthalazine-1-carboxamido)benzoate | 548 [M + H] |

Example 85: Synthesis of N-(2,2-difluorobenzo[d][1,3]dioxol-5-yl)-N-ethyl-2-(1-oxo-5-(pyridin-2-ylmethyl)-1H-pyridazino[4,5-b]indol-2(5H)-yl)acetamide

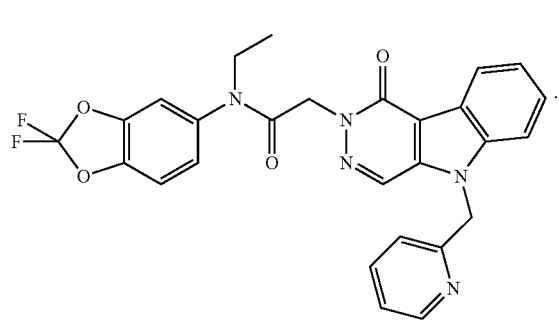 [SMILES: CCN(C(=O)Cn1ncc2c(c1=O)c1ccccc1n2Cc1ccccn1)c1ccc2c(c1)OC(F)(F)O2]

5-chloro-4-phenylpyridazin-3(2H)-one

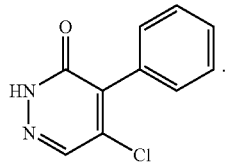 [SMILES: O=c1[nH]ncc(Cl)c1-c1ccccc1]

To a stirred solution of 4,5-dichloropyridazone (5.0 g, 30.3 mmol) in THF (100 mL) was added PhMgBr (1M in THF, 90.9 mL, 90.9 mmol) dropwise at 15° C., then stirred under nitrogen at 15° C. for 30 min and at rt 2 hr. The reaction mixture was quenched with a saturated solution of ammonium chloride (500 mL) and extracted with EtOAc (250 mL×2). The extract was washed with brine, dried over sodium sulfate and concentrated to give 5-chloro-4-phenylpyridazin-3(2H)-one (5.02 g, 207 [M+H]). $^1$H NMR: (400 MHz, DMSO) δ: 7.417-7.505 (m, 5H), 8.119 (s, 1H), 13.443 (s, 1H).

2-(4-chloro-6-oxo-5-phenylpyridazin-1(6H)-yl)-N-(2,2-difluorobenzo[d][1,3]dioxol-5-yl)-N-ethylacetamide

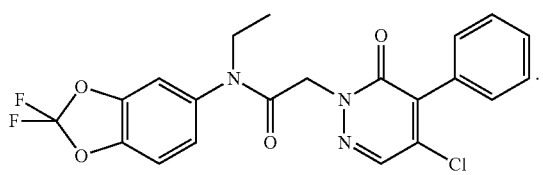 [SMILES: CCN(C(=O)Cn1ncc(Cl)c(-c2ccccc2)c1=O)c1ccc2c(c1)OC(F)(F)O2]

To a stirred solution of 5-chloro-4-phenylpyridazin-3(2H)-one (3.0 g, 14.5 mmol) in THF (30 mL) was added NaH (0.699 g, 17.4 mmol) portion wise at 0° C. The reaction mixture was stirred for 30 min at 0° C. A solution of 2-bromo-N-(2,2-difluorobenzo[d][1,3]dioxol-5-yl)-N-ethylacetamide (4.68 g, 14.5 mmol) in THF (5 mL) was added dropwise and the reaction mixture stirred for 16 hr at rt. The reaction mixture was diluted with saturated aqueous ammonium chloride solution (200 mL) and extracted with EtOAc (250 mL×2). The extract was washed with brine (300 mL), dried over anhydrous sodium sulfate and concentrated to give crude product which was purified by column chromatography (20-25% EtOAc/hexane) to give 2-(4-chloro-6-oxo-5-phenylpyridazin-1(6H)-yl)-N-(2,2-difluorobenzo[d][1,3]dioxol-5-yl)-N-ethylacetamide (5.01 g, 448 [M+H]). $^1$H NMR: (400 MHz, DMSO) δ: 0.994-1.027 (t, J=6.6 Hz, 3H), 3.655-3.671 (q, J=6.4 Hz, 2H), 4.608 (s, 2H), 7.281-7.302 (d, J=8.4 Hz, 1H), 7.373-7.483 (m, 5H), 7.531-7.552 (d, J=4.8 Hz, 1H), 7.631 (s, 1H), 8.191 (s, 1H).

N-(2,2-difluorobenzo[d][1,3]dioxol-5-yl)-N-ethyl-2-(1-oxo-1H-pyridazino[4,5-b]indol-2(5H)-yl)acetamide

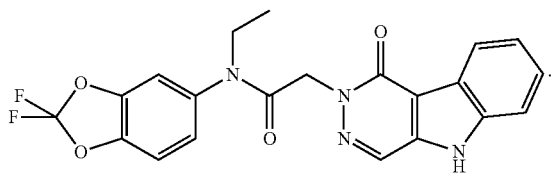 [SMILES: CCN(C(=O)Cn1ncc2[nH]c3ccccc3c2c1=O)c1ccc2c(c1)OC(F)(F)O2]

To a solution of 2-(4-chloro-6-oxo-5-phenylpyridazin-1(6H)-yl)-N-(2,2-difluorobenzo[d][1,3]dioxol-5-yl)-N-ethylacetamide (5.0 g, 11.2 mmol) in DMF (40 mL) was added sodium azide (1.45 g, 22.3 mmol). The reaction was stirred for 16 hr at 110° C., then cooled to rt diluted with water (100 mL) and the product was extracted in EtOAc (250 mL×2). The extract was washed with brine, dried over anhydrous sodium sulfate and concentrated to give a residue which was purified by chromatography (20-25% EtOAc/DCM) to give N-(2,2-difluorobenzo[d][1,3]dioxol-5-yl)-N-ethyl-2-(1-oxo-1H-pyridazino[4,5-b]indol-2(5H)-yl)acetamide (3.6 g, 427 [M+H]). $^1$H NMR: (400 MHz, DMSO) δ: 1.017-1.052 (t, J=7 Hz, 3H), 3.633-3.690 (q, J=7.6 Hz, 2H), 4.718 (s, 2H), 7.266-7.606 (m, 6H), 8.130-8.150 (d, J=8 Hz, 1H), 8.397 (s, 1H), 12.300 (s, 1H).

N-(2,2-difluorobenzo[d][1,3]dioxol-5-yl)-N-ethyl-2-(1-oxo-5-(pyridin-2-ylmethyl)-1H-pyridazino[4,5-b]indol-2(5H)-yl)acetamide

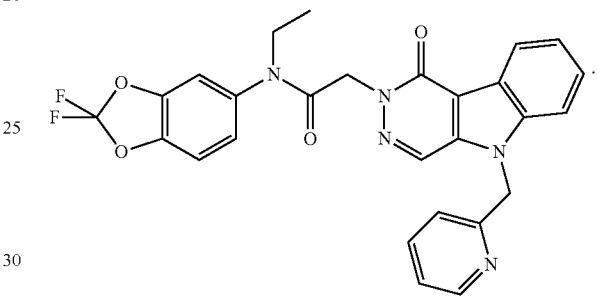

To a solution of N-(2,2-difluorobenzo[d][1,3]dioxol-5-yl)-N-ethyl-2-(1-oxo-1H-pyridazino[4,5-b]indol-2(5H)-yl)acetamide (0.2 g, 0.469 mmol) in THF (10 mL) was added NaH (0.022 g, 0.56 mmol) portion wise at 0° C. After stirring 30 minutes at 0° C., 2-(bromomethyl)pyridine.HBr (0.081 g, 0.516 mmol) was added and the reaction stirred for an additional 16 h at rt. The reaction mixture was diluted with water (20 mL) and extracted in EtOAc (25 mL×2). The extract was washed with brine, dried over anhydrous sodium sulfate and concentrate to give a residue which was purified by chromatography (10-12% EtOAc/DCM) to give N-(2,2-difluorobenzo[d][1,3]dioxol-5-yl)-N-ethyl-2-(1-oxo-5-(pyridin-2-ylmethyl)-1H-pyridazino[4,5-b]indol-2(5H)-yl)acetamide (0.045 g, 519 [M+H]). $^1$H NMR: (400 MHz, DMSO) δ: 1.021-1.056 (t, J=7, 3H), 3.710-3.656 (qt, J=6.8, 13.6, 2H), 4.733 (s, 2H), 5.890 (s, 2H), 7.312-7.281 (m, 1H), 7.408-7.349 (m, 3H), 7.558-7.486 (m, 2H), 7.700 (s, 1H), 7.814-7.771 (m, 2H), 8.186-8.167 (d, J=7.6, 1H), 8.477-8.463 (dd, J=0.8, 5.2, 1H), 8.739 (s, 1H).

Representative compounds of the invention were prepared in a similar manner to examples 82 (scheme 5).

| Example No. | Structure | IUPAC Name | LCMS m/z |
| --- | --- | --- | --- |
| 86. | 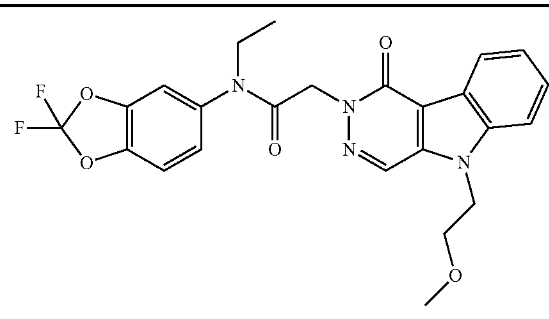 | N-(2,2-difluorobenzo[d][1,3]dioxol-5-yl)-N-ethyl-2-(5-(2-methoxyethyl)-1-oxo-1H-pyridazino[4,5-b]indol-2(5H)-yl)acetamide | 485 [M + H] |

| Example No. | Structure | IUPAC Name | LCMS m/z |
|---|---|---|---|
| 87. | 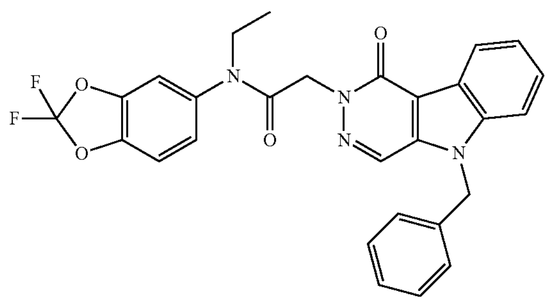 [SMILES: CCN(C(=O)Cn1ncc2c(c1=O)c1ccccc1n2Cc1ccccc1)c1ccc2c(c1)OC(F)(F)O2] | 2-(5-benzyl-1-oxo-1H-pyridazino[4,5-b]indol-2(5H)-yl)-N-(2,2-difluorobenzo[d][1,3]dioxol-5-yl)-N-ethylacetamide | 517 [M + H] |
| 88. | 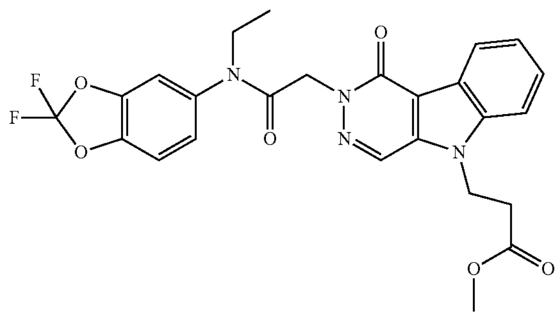 | methyl 3-(2-(2-((2,2-difluorobenzo[d][1,3]dioxol-5-yl)(ethyl)amino)-2-oxoethyl)-1-oxo-1H-pyridazino[4,5-b]indol-5(2H)-yl)propanoate | 513 [M + H] |
| 89. | 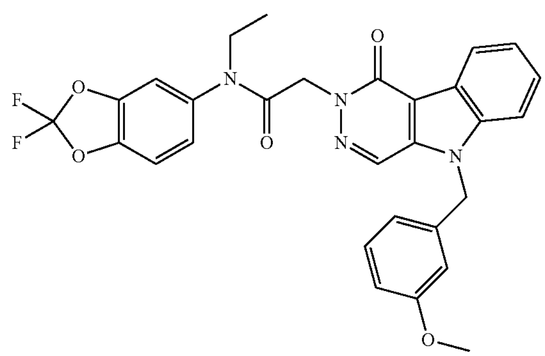 [SMILES: CCN(C(=O)Cn1ncc2c(c1=O)c1ccccc1n2Cc1cccc(OC)c1)c1ccc2c(c1)OC(F)(F)O2] | N-(2,2-difluorobenzo[d][1,3]dioxol-5-yl)-N-ethyl-2-(5-(3-methoxybenzyl)-1-oxo-1H-pyridazino[4,5-b]indol-2(5H)-yl)acetamide | 547 [M + H] |
| 90. | 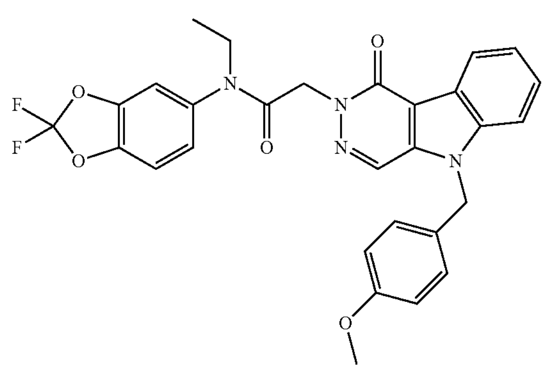 [SMILES: CCN(C(=O)Cn1ncc2c(c1=O)c1ccccc1n2Cc1ccc(OC)cc1)c1ccc2c(c1)OC(F)(F)O2] | N-(2,2-difluorobenzo[d][1,3]dioxol-5-yl)-N-ethyl-2-(5-(4-methoxybenzyl)-1-oxo-1H-pyridazino[4,5-b]indol-2(5H)-yl)acetamide | 547 [M + H] |
| 91. | 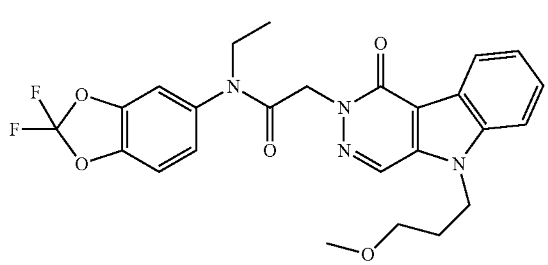 [SMILES: CCN(C(=O)Cn1ncc2c(c1=O)c1ccccc1n2CCCOC)c1ccc2c(c1)OC(F)(F)O2] | N-(2,2-difluorobenzo[d][1,3]dioxol-5-yl)-N-ethyl-2-(5-(3-methoxypropyl)-1-oxo-1H-pyridazino[4,5-b]indol-2(5H)-yl)acetamide | 499 [M + H] |

| Example No. | Structure | IUPAC Name | LCMS m/z |
|---|---|---|---|
| 92. | 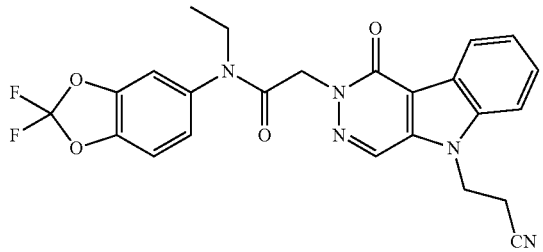 [SMILES: CCN(C(=O)Cn1ncc2c(c1=O)c1ccccc1n2CCC#N)c1ccc2c(c1)OC(F)(F)O2] | 2-(5-(2-cyanoethyl)-1-oxo-1H-pyridazino[4,5-b]indol-2(5H)-yl)-N-(2,2-difluorobenzo[d][1,3]dioxol-5-yl)-N-ethylacetamide | 480 [M + H] |
| 93. | 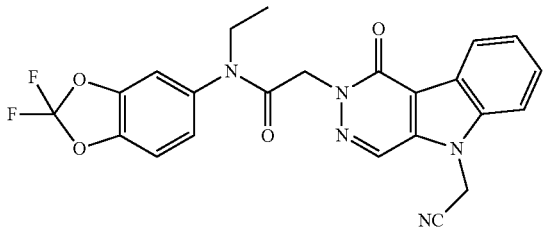 [SMILES: CCN(C(=O)Cn1ncc2c(c1=O)c1ccccc1n2CC#N)c1ccc2c(c1)OC(F)(F)O2] | 2-(5-(cyanomethyl)-1-oxo-1H-pyridazino[4,5-b]indol-2(5H)-yl)-N-(2,2-difluorobenzo[d][1,3]dioxol-5-yl)-N-ethylacetamide | 466 [M + H] |
| 94. | 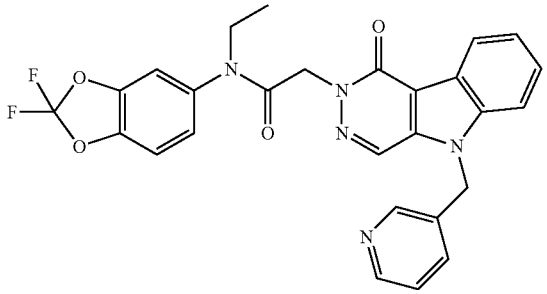 | N-(2,2-difluorobenzo[d][1,3]dioxol-5-yl)-N-ethyl-2-(1-oxo-5-(pyridin-3-ylmethyl)-1H-pyridazino[4,5-b]indol-2(5H)-yl)acetamide | 518 [M + H] |
| 95. | 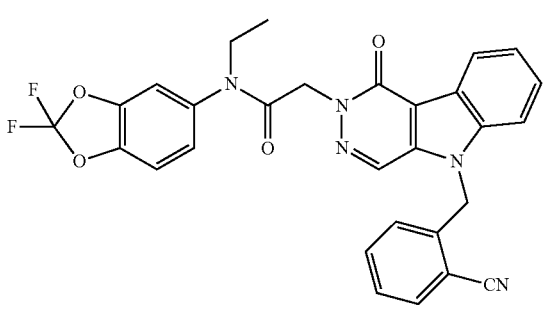 [SMILES: CCN(C(=O)Cn1ncc2c(c1=O)c1ccccc1n2Cc1ccccc1C#N)c1ccc2c(c1)OC(F)(F)O2] | 2-(5-(2-cyanobenzyl)-1-oxo-1H-pyridazino[4,5-b]indol-2(5H)-yl)-N-(2,2-difluorobenzo[d][1,3]dioxol-5-yl)-N-ethylacetamide | 542 [M + H] |
| 96. | 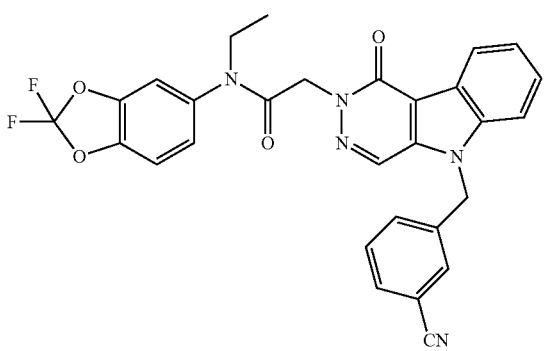 [SMILES: CCN(C(=O)Cn1ncc2c(c1=O)c1ccccc1n2Cc1cccc(C#N)c1)c1ccc2c(c1)OC(F)(F)O2] | 2-(5-(3-cyanobenzyl)-1-oxo-1H-pyridazino[4,5-b]indol-2(5H)-yl)-N-(2,2-difluorobenzo[d][1,3]dioxol-5-yl)-N-ethylacetamide | 542 [M + H] |

-continued

| Example No. | Structure | IUPAC Name | LCMS m/z |
|---|---|---|---|
| 97. | 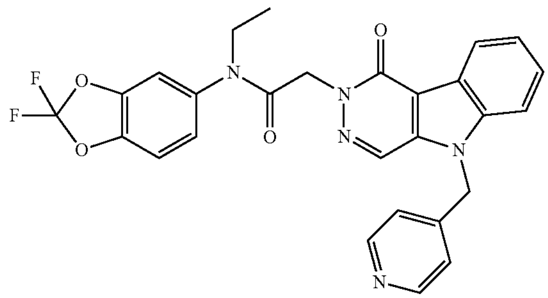 | N-(2,2-difluorobenzo[d][1,3]dioxol-5-yl)-N-ethyl-2-(1-oxo-5-(pyridin-4-ylmethyl)-1H-pyridazino[4,5-b]indol-2(5H)-yl)acetamide | 518 [M + H] |
| 98. | 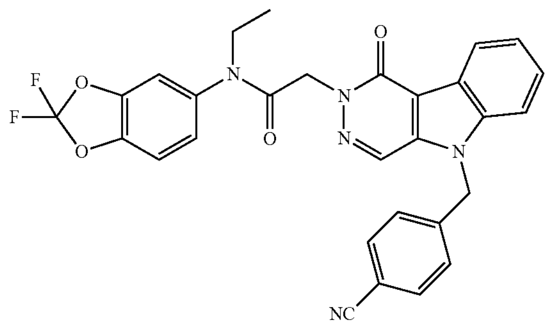 [SMILES: CCN(C(=O)Cn1ncc2c(c1=O)c1ccccc1n2Cc1ccc(C#N)cc1)c1ccc2c(c1)OC(F)(F)O2] | 2-(5-(4-cyanobenzyl)-1-oxo-1H-pyridazino[4,5-b]indol-2(5H)-yl)-N-(2,2-difluorobenzo[d][1,3]dioxol-5-yl)-N-ethylacetamide | 542 [M + H] |
| 99. | 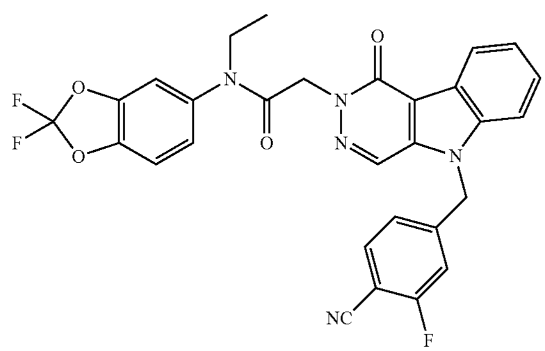 [SMILES: CCN(C(=O)Cn1ncc2c(c1=O)c1ccccc1n2Cc1ccc(C#N)c(F)c1)c1ccc2c(c1)OC(F)(F)O2] | 2-(5-(4-cyano-3-fluorobenzyl)-1-oxo-1H-pyridazino[4,5-b]indol-difluorobenzo[d][1,3]dioxol-5-yl)-N-ethylacetamide | 560 [M + H] |
| 100. | 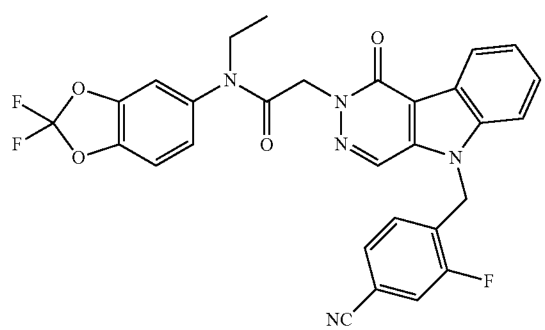 [SMILES: CCN(C(=O)Cn1ncc2c(c1=O)c1ccccc1n2Cc1ccc(C#N)cc1F)c1ccc2c(c1)OC(F)(F)O2] | 2-(5-(4-cyano-2-fluorobenzyl)-1-oxo-1H-pyridazino[4,5-b]indol-2(5H)-yl)-N-(2,2-difluorobenzo[d][1,3]dioxol-5-yl)-N-ethylacetamide | 560 [M + H] |

Example 101: Synthesis of 5-methyl-1-(piperidine-1-carbonyl)-3-p-tolyl-3H-pyridazino[4,5-b]indol-4(5H)-one

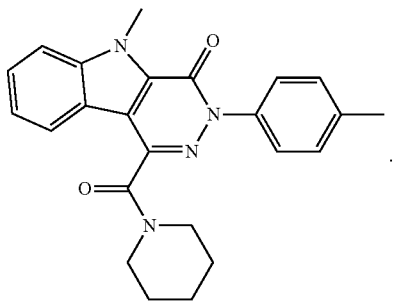 [SMILES: Cc1ccc(-n2nc(C(=O)N3CCCCC3)c3c4ccccc4n(C)c3c2=O)cc1]

Ethyl 1-methyl-1H-indole-2-carboxylate

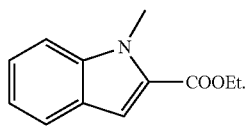

Ethyl 1H-indole-2-carboxylate (5.0 g, 26.45 mmol) was dissolved in DMF (40 mL), then NaH (60%) (1.58 g, 39.68 mmol) was added at 0° C. After stirring for 20 min at this temperature, iodomethane (8.27 mL, 13.22 mmol) was added dropwise and the reaction stirred at rt for 16 hr. It was partitioned between aq saturated NH₄Cl (100 mL) and diethyl ether (100 mL), and the aqueous layer was further extracted with diethyl ether (2×50 mL). The organic layers were combined and dried (Na₂SO₄), then the solvent was removed in vacuo to obtain ethyl 1-methyl-1H-indole-2-carboxylate (4.0 g, 74.48%).

Ethyl 3-(2-ethoxy-2-oxoacetyl)-1-methyl-1H-indole-2-carboxylate

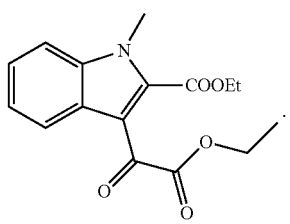 [SMILES: CCOC(=O)C(=O)c1c(C(=O)OCC)n(C)c2ccccc12]

To a solution of ethyl chloro oxoacetate (0.60 mL, 5.41 mmol) in DCE (30 mL) was added TiCl₄ (0.59 mL, 5.41 mmol) at rt, and the reaction stirred for 30 min at rt. Ethyl 1-methyl-1H-indole-2-carboxylate (1.0 g, 4.92 mmol) in DCE was added dropwise and the reaction stirred for 3 hr at rt. The reaction was quenched with saturated NH₄Cl solution (50 mL) and extracted with DCM (25 mL×3). The organic layer was dried over Na₂SO₄ and concentrated to give ethyl 3-(2-ethoxy-2-oxoacetyl)-1-methyl-1H-indole-2-carboxylate (1.0 g). MS: ESI+ve, 304.6 [M+H].

5-Methyl-4-oxo-3-p-tolyl-4,5-dihydro-3H-pyridazino[4,5-b]indole-1-carboxylate

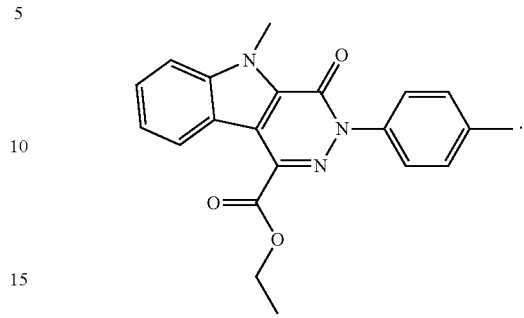

To a stirred solution of ethyl 3-(2-ethoxy-2-oxoacetyl)-1-methyl-1H-indole-2-carboxylate (0.9 g, 3.11 mmol) in HOAc (20 mL) was added p-tolylhydrazine hydrochloride (0.6 g, 3.92 mmol). The reaction mixture was heated at 100° C. for 16 hr, then the reaction was quenched with water (5 mL) and neutralized with aq NaHCO₃ solution (10 mL). The aqueous layered was extracted with EtOAc (3×30 mL), and the combined organic layers dried with Na₂SO₄, then concentrated. The crude product was purified by column chromatography (10-50% EtOAc/hexane) to give ethyl 5-methyl-4-oxo-3-p-tolyl-4,5-dihydro-3H-pyridazino[4,5-b]indole-1-carboxylate (0.33 g). MS: ESI+ve, 348.69 [M+H].

Example 101: of 5-methyl-1-(piperidine-1-carbonyl)-3-p-tolyl-3H-pyridazino[4,5-b]indol-4(5H)-one Me₃Al (2M in toluene, 1.05 mL, 2.07 mmol) was added dropwise to a stirred solution of piperidine (0.107 g, 1.24 mmol) in toluene (5 mL). After stirring the mixture for 2 hr at rt, ethyl 5-methyl-4-oxo-3-p-tolyl-4,5-dihydro-3H-pyridazino[4,5-b]indole-1-carboxylate (0.150 g, 0.41 mmol) was added and the reaction heated to 110° C. for 2 h. The reaction was quenched with water (15 mL) and extracted with EtOAc (3×20 mL). The organic layer was dried over Na₂SO₄, then concentrated to obtain crude material, which was purified by column chromatography (5-50% EtOAc/hexane) to yield 5-methyl-1-(piperidine-1-carbonyl)-3-p-tolyl-3H-pyridazino[4,5-b]indol-4(5H)-one (0.036 g); MS: ESI+ve, 401.34 [M+H]. ¹H NMR (DMSO-d₆) δ 7.84 (m, 2H), 7.64 (m, 1H), 7.45 (m, 3H), 7.33 (m, 2H), 4.34 (s, 3H), 3.77 (m, 2H), 3.43 (q, 2H), 2.40 (s, 3H), 1.65 (m, 4H), 1.37 (m, 2H).

Representative compounds of the invention were prepared in a similar manner to example 101 (scheme 7).

| Example No. | Structure | IUPAC Name | LCMS m/z |
| --- | --- | --- | --- |
| 102. | 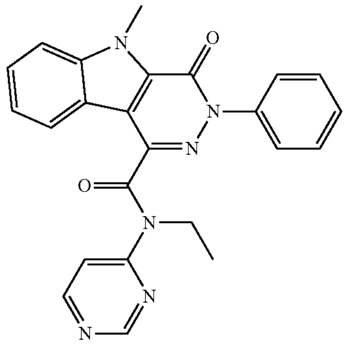 | N-ethyl-5-methyl-4-oxo-3-phenyl-N-(pyrimidin-4-yl)-4,5-dihydro-3H-pyridazino[4,5-b]indole-1-carboxamide | 439 [M + H] |
| 103. | 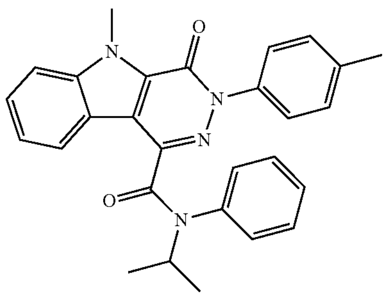 [SMILES: Cc1ccc(-n2nc(C(=O)N(c3ccccc3)C(C)C)c3c4ccccc4n(C)c3c2=O)cc1] | N-isopropyl-5-methyl-4-oxo-N-phenyl-3-(p-tolyl)-4,5-dihydro-3H-pyridazino[4,5-b]indole-1-carboxamide | 451 [M + H] |
| 104. | 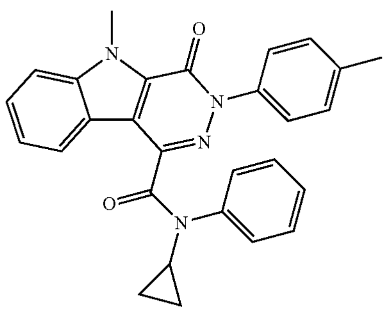 [SMILES: Cc1ccc(-n2nc(C(=O)N(c3ccccc3)C3CC3)c3c4ccccc4n(C)c3c2=O)cc1] | N-cyclopropyl-5-methyl-4-oxo-N-phenyl-3-(p-tolyl)-4,5-dihydro-3H-pyridazino[4,5-b]indole-1-carboxamide | 449 [M + H] |
| 105. | 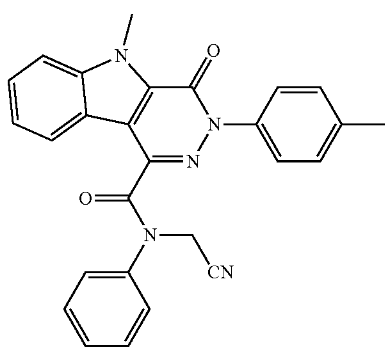 [SMILES: Cc1ccc(-n2nc(C(=O)N(CC#N)c3ccccc3)c3c4ccccc4n(C)c3c2=O)cc1] | N-(cyanomethyl)-5-methyl-4-oxo-N-phenyl-3-(p-tolyl)-4,5-dihydro-3H-pyridazino[4,5-b]indole-1-carboxamide | 448 [M + H] |
| 106. | 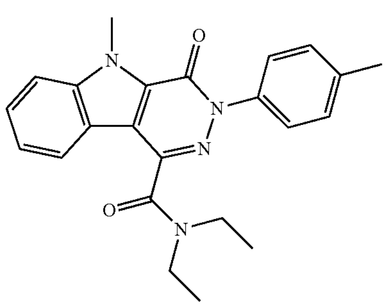 [SMILES: CCN(CC)C(=O)c1nn(-c2ccc(C)cc2)c(=O)c2c1c1ccccc1n2C] | N,N-diethyl-5-methyl-4-oxo-3-(p-tolyl)-4,5-dihydro-3H-pyridazino[4,5-b]indole-1-carboxamide | 389 [M + H] |

-continued

| Example No. | Structure | IUPAC Name | LCMS m/z |
|---|---|---|---|
| 107. | 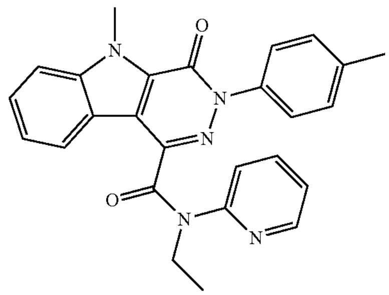 [SMILES: CCN(C(=O)c1nn(-c2ccc(C)cc2)c(=O)c2c1c1ccccc1n2C)c1ccccn1] | N-ethyl-5-methyl-4-oxo-N-(pyridin-2-yl)-3-(p-tolyl)-4,5-dihydro-3H-pyridazino[4,5-b]indole-1-carboxamide | 438 [M + H] |
| 108. | 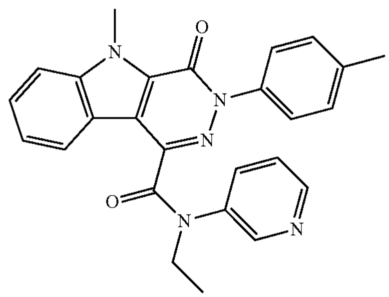 [SMILES: CCN(C(=O)c1nn(-c2ccc(C)cc2)c(=O)c2c1c1ccccc1n2C)c1cccnc1] | N-ethyl-5-methyl-4-oxo-N-(pyridin-3-yl)-3-(p-tolyl)-4,5-dehydro-3H-pyridazino[4,5-b]indole-1-carboxamide | 438 [M + H] |
| 109. | 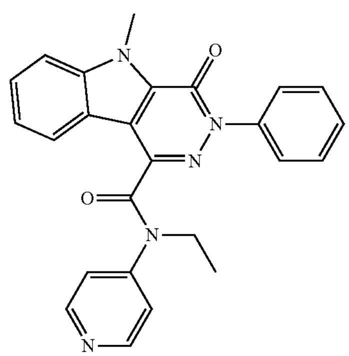 | N-ethyl-5-methyl-4-oxo-3-phenyl-N-(pyridin-4-yl)-4,5-dihydro-3H-pyridazino[4,5-b]indole-1-carboxamide | 438 [M + H] |
| 110. | 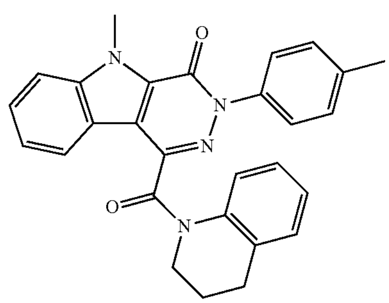 [SMILES: Cc1ccc(-n2nc(C(=O)N3CCCc4ccccc43)c3c4ccccc4n(C)c3c2=O)cc1] | 5-methyl-1-(1,2,3,4-tetrahydroquinoline-1-carbonyl)-3-(p-tolyl)-3H-pyridazino[4,5-b]indol-4(5H)-one | 449 [M + H] |
| 111. | 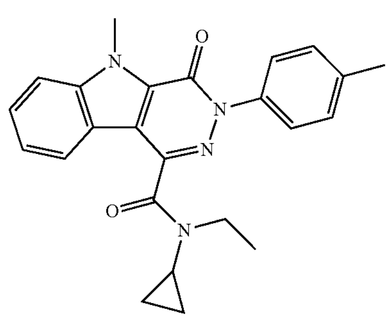 [SMILES: CCN(C(=O)c1nn(-c2ccc(C)cc2)c(=O)c2c1c1ccccc1n2C)C1CC1] | N-cyclopropyl-N-ethyl-5-methyl-4-oxo-3-(p-tolyl)-4,5-dihydro-3H-pyridazino[4,5-b]indole-1-carboxamide | 401 [M + H] |

| Example No. | Structure | IUPAC Name | LCMS m/z |
|---|---|---|---|
| 112. | 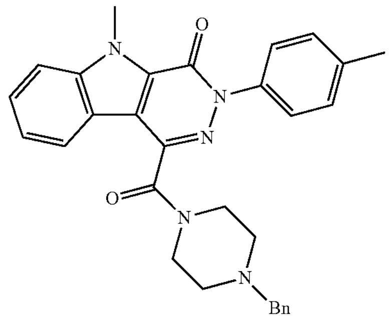 [SMILES: Cc1ccc(-n2nc(C(=O)N3CCN(Cc4ccccc4)CC3)c3c4ccccc4n(C)c3c2=O)cc1] | 1-(4-benzylpiperazine-1-carbonyl)-5-methyl-3-(p-tolyl)-3H-pyridazino[4,5-b]indol-4(5H)-one | 492 [M + H] |
| 113. | 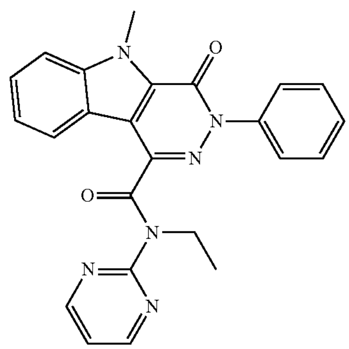 | N-ethyl-5-methyl-4-oxo-3-phenyl-N-(pyrimidin-2-yl)-4,5-dihydro-3H-pyridazino[4,5-b]indole-1-carboxamide | 439 [M + H] |
| 114. | 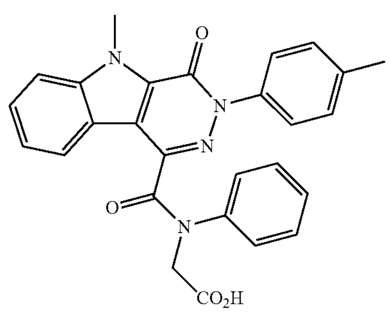 [SMILES: Cc1ccc(-n2nc(C(=O)N(CC(=O)O)c3ccccc3)c3c4ccccc4n(C)c3c2=O)cc1] | 2-(5-methyl-4-oxo-N-phenyl-3-(p-tolyl)-4,5-dihydro-3H-pyridazino[4,5-b]indole-1-carboxamido)acetic acid | 467 [M + H] |
| 115. | 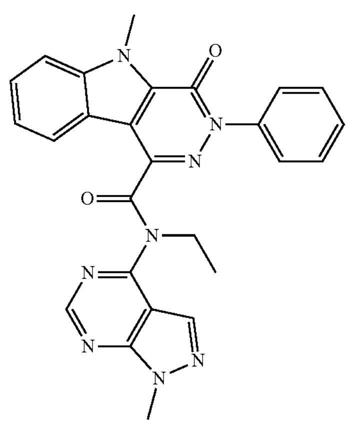 | N-ethyl-5-methyl-N-(1-methyl-1H-pyrazolo[3,4-d]pyrimidin-4-yl)-4-oxo-3-phenyl-4,5-dihydro-3H-pyridazino[4,5-b]indole-1-carboxamide | 493 [M + H] |

| Example No. | Structure | IUPAC Name | LCMS m/z |
|---|---|---|---|
| 116. | 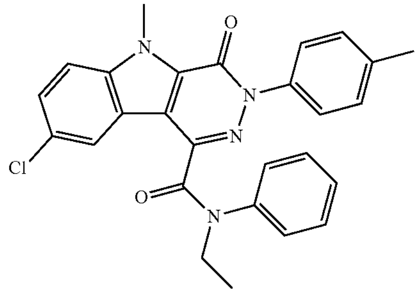 [SMILES: CCN(C(=O)c1nn(-c2ccc(C)cc2)c(=O)c2c1c1cc(Cl)ccc1n2C)c1ccccc1] | 8-chloro-N-ethyl-5-methyl-4-oxo-N-phenyl-3-(p-tolyl)-4,5-dihydro-3H-pyridazino[4,5-b]indole-1-carboxamide | 472 [M + H] |
| 117. | 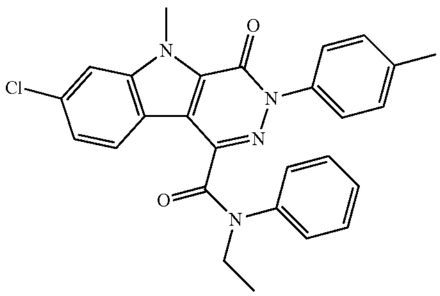 [SMILES: CCN(C(=O)c1nn(-c2ccc(C)cc2)c(=O)c2c1c1ccc(Cl)cc1n2C)c1ccccc1] | 7-chloro-N-ethyl-5-methyl-4-oxo-N-phenyl-3-(p-tolyl)-4,5-dihydro-3H-pyridazino[4,5-b]indole-1-carboxamide | 472 [M + H] |
| 118. | 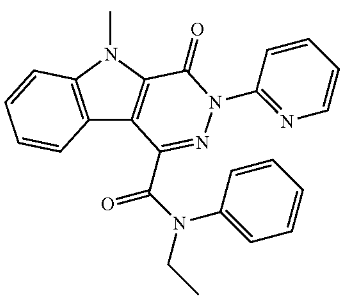 [SMILES: CCN(C(=O)c1nn(-c2ccccn2)c(=O)c2c1c1ccccc1n2C)c1ccccc1] | N-ethyl-5-methyl-4-oxo-N-phenyl-3-(pyridin-2-yl)-4,5-dihydro-3H-pyridazino[4,5-b]indole-1-carboxamide | 424 [M + H] |
| 119. | 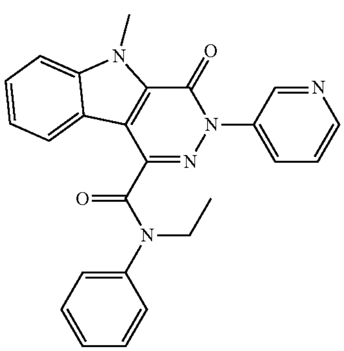 [SMILES: CCN(C(=O)c1nn(-c2cccnc2)c(=O)c2c1c1ccccc1n2C)c1ccccc1] | 3-benzyl-N-ethyl-5-methyl-4-oxo-N-phenyl-4,5-dihydro-3H-pyridazino[4,5-b]indole-1-carboxamide | 424 [M + H] |
| 120. | 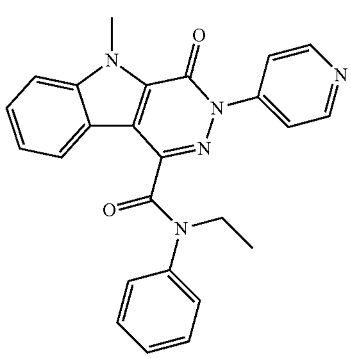 [SMILES: CCN(C(=O)c1nn(-c2ccncc2)c(=O)c2c1c1ccccc1n2C)c1ccccc1] | N-ethyl-5-methyl-4-oxo-N-phenyl-3-(pyridin-4-yl)-4,5-dihydro-3H-pyridazino[4,5-b]indole-1-carboxamide | 424 [M + H] |

-continued

| Example No. | Structure | IUPAC Name | LCMS m/z |
|---|---|---|---|
| 121. | 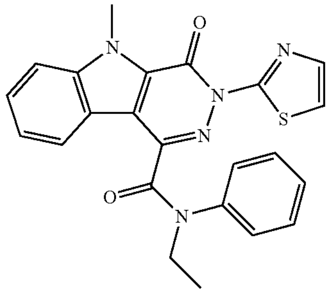 [SMILES: CCN(C(=O)c1nn(-c2nccs2)c(=O)c2c1c1ccccc1n2C)c1ccccc1] | N-ethyl-5-methyl-4-oxo-N-phenyl-3-(thiazol-2-yl)-4,5-dihydro-3H-pyridazino[4,5-b]indole-1-carboxamide | 430 [M + H] |
| 122. | 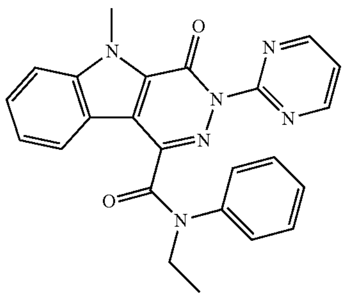 [SMILES: CCN(C(=O)c1nn(-c2ncccn2)c(=O)c2c1c1ccccc1n2C)c1ccccc1] | N-ethyl-5-methyl-4-oxo-N-phenyl-3-(pyrimidin-2-yl)-4,5-dihydro-3H-pyridazino[4,5-b]indole-1-carboxamide | 425 [M + H] |
| 123. | 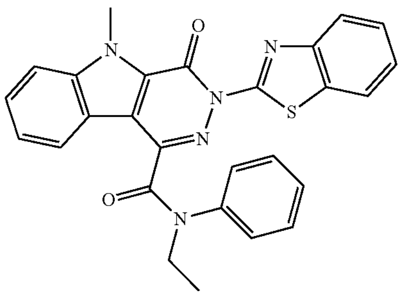 [SMILES: CCN(C(=O)c1nn(-c2nc3ccccc3s2)c(=O)c2c1c1ccccc1n2C)c1ccccc1] | 3-(benzo[d]thiazol-2-yl)-N-ethyl-5-methyl-4-oxo-N-phenyl-4,5-dihydro-3H-pyridazino[4,5-b]indole-1-carboxamide | 480 [M + H] |
| 124. | 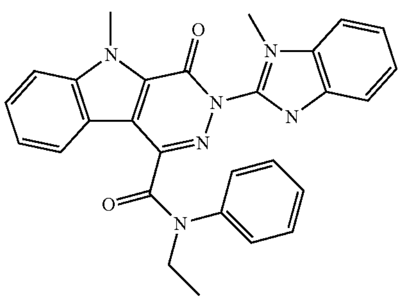 | N-ethyl-5-methyl-3-(1-methyl-1H-benzo[d]imidazol-2-yl)-4-oxo-N-phenyl-4,5-dihydro-3H-pyridazino[4,5-b]indole-1-carboxamide | 477 [M + H] |
| 125. | 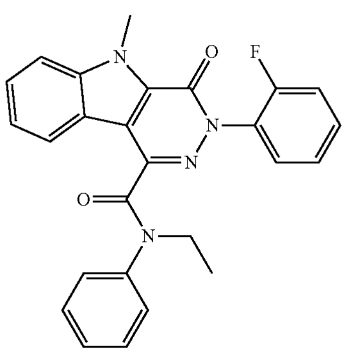 [SMILES: CCN(C(=O)c1nn(-c2ccccc2F)c(=O)c2c1c1ccccc1n2C)c1ccccc1] | N-ethyl-3-(2-fluorophenyl)-5-methyl-4-oxo-N-phenyl-4,5-dihydro-3H-pyridazino[4,5-b]indole-1-carboxamide | 441 [M + H] |

-continued

| Example No. | Structure | IUPAC Name | LCMS m/z |
|---|---|---|---|
| 126. | 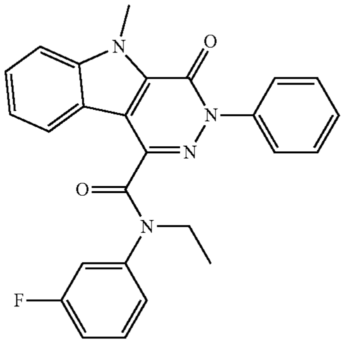 [SMILES: CCN(C(=O)c1nn(-c2ccccc2)c(=O)c2c1c1ccccc1n2C)c1cccc(F)c1] | N-ethyl-N-(3-fluorophenyl)-5-methyl-4-oxo-3-phenyl-4,5-dihydro-3H-pyridazino[4,5-b]indole-1-carboxamide | 442 [M + H] |
| 127. | 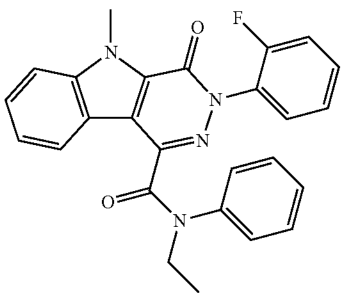 [SMILES: CCN(C(=O)c1nn(-c2ccccc2F)c(=O)c2c1c1ccccc1n2C)c1ccccc1] | N-ethyl-3-(2-fluorophenyl)-5-methyl-4-oxo-N-phenyl-4,5-dihydro-3H-pyridazino[4,5-b]indole-1-carboxamide | 441 [M + H] |
| 128. | 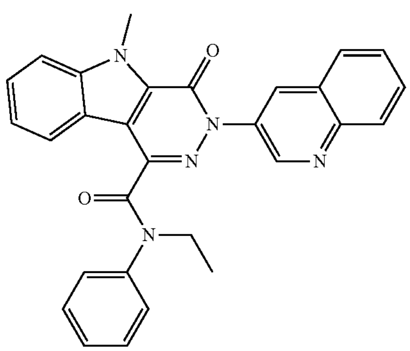 [SMILES: CCN(C(=O)c1nn(-c2cnc3ccccc3c2)c(=O)c2c1c1ccccc1n2C)c1ccccc1] | N-ethyl-5-methyl-4-oxo-N-phenyl-3-(quinolin-3-yl)-4,5-dihydro-3H-pyridazino[4,5-b]indole-1-carboxamide | 474 [M + H] |
| 129. | 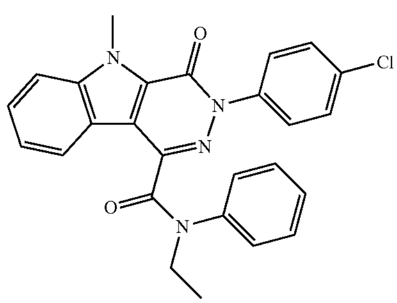 [SMILES: CCN(C(=O)c1nn(-c2ccc(Cl)cc2)c(=O)c2c1c1ccccc1n2C)c1ccccc1] | 3-(4-chlorophenyl)-N-ethyl-5-methyl-4-oxo-N-phenyl-4,5-dihydro-3H-pyridazino[4,5-b]indole-1-carboxamide | 457 [M + H] |
| 130. | 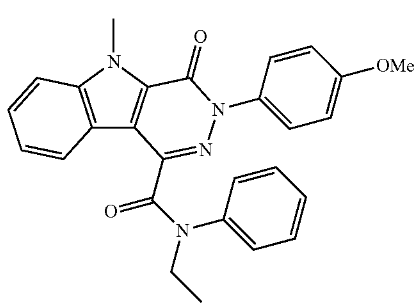 [SMILES: CCN(C(=O)c1nn(-c2ccc(OC)cc2)c(=O)c2c1c1ccccc1n2C)c1ccccc1] | N-ethyl-3-(4-methoxyphenyl)-5-methyl-4-oxo-N-phenyl-4,5-dihydro-3H-pyridazino[4,5-b]indole-1-carboxamide | 453 [M + H] |

| Example No. | Structure | IUPAC Name | LCMS m/z |
| --- | --- | --- | --- |
| 131. | 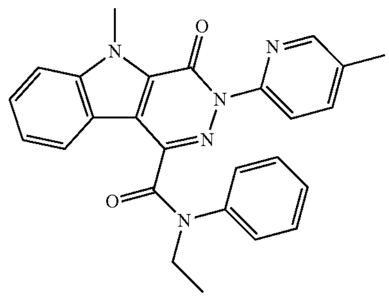 [SMILES: CCN(C(=O)c1nn(-c2ccc(C)cn2)c(=O)c2c1c1ccccc1n2C)c1ccccc1] | N-ethyl-5-methyl-3-(5-methylpyridin-2-yl)-4-oxo-N-phenyl-4,5-dihydro-3H-pyridazino[4,5-b]indole-1-carboxamide | 438 [M + H] |
| 132. | 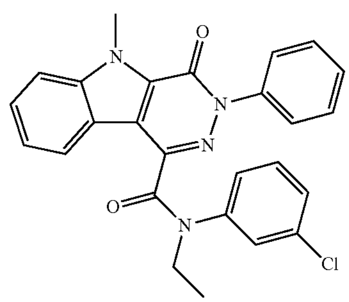 [SMILES: CCN(C(=O)c1nn(-c2ccccc2)c(=O)c2c1c1ccccc1n2C)c1cccc(Cl)c1] | N-(3-chlorophenyl)-N-ethyl-5-methyl-4-oxo-3-phenyl-4,5-dihydro-3H-pyridazino[4,5-b]indole-1-carboxamide | 457 [M + H] |
| 133. | 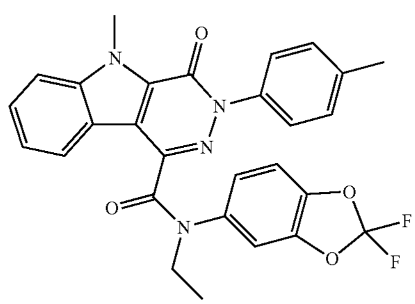 [SMILES: CCN(C(=O)c1nn(-c2ccc(C)cc2)c(=O)c2c1c1ccccc1n2C)c1ccc2c(c1)OC(F)(F)O2] | N-(2,2-difluorobenzo[d][1,3]dioxol-5-yl)-N-ethyl-5-methyl-4-oxo-3-(p-tolyl)-4,5-dihydro-3H-pyridazino[4,5-b]indole-1-carboxamide | 517 [M + H] |
| 134. | 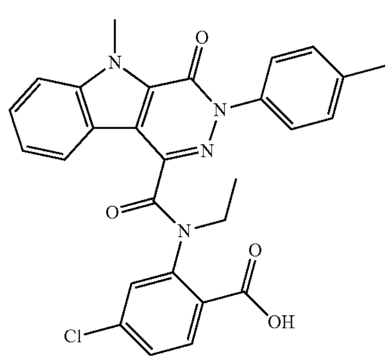 [SMILES: CCN(C(=O)c1nn(-c2ccc(C)cc2)c(=O)c2c1c1ccccc1n2C)c1cc(Cl)ccc1C(=O)O] | 4-chloro-2-(N-ethyl-5-methyl-4-oxo-3-(p-tolyl)-4,5-dihydro-3H-pyridazino[4,5-b]indole-1-carboxamido)benzoic acid | 515 [M + H] |

| Example No. | Structure | IUPAC Name | LCMS m/z |
|---|---|---|---|
| 135. | 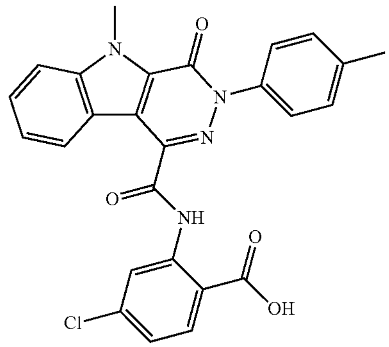 [SMILES: Cc1ccc(-n2nc(C(=O)Nc3cc(Cl)ccc3C(=O)O)c3c4ccccc4n(C)c3c2=O)cc1] | 4-chloro-2-(5-methyl-4-oxo-3-(p-tolyl)-4,5-dihydro-3H-pyridazino[4,5-b]indole-1-carboxamido)benzoic acid | 487 [M + H] |

Example 136: Synthesis of 3-benzyl-N-ethyl-5-methyl-4-oxo-N-phenyl-4,5-dihydro-3H-pyridazino[4,5-b]indole-1-carboxamide

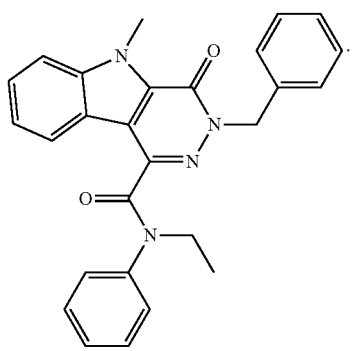 [SMILES: CCN(C(=O)c1nn(Cc2ccccc2)c(=O)c2c1c1ccccc1n2C)c1ccccc1]

5-Methyl-4-oxo-4,5-dihydro-3H-pyridazino[4,5-b]indole-1-carboxylate

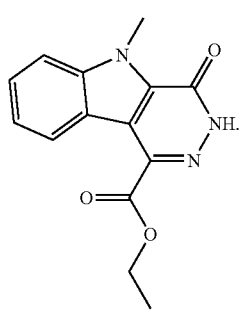 [SMILES: CCOC(=O)c1n[nH]c(=O)c2c1c1ccccc1n2C]

To a stirred solution of ethyl 3-(2-ethoxy-2-oxoacetyl)-1-methyl-1H-indole-2-carboxylate (0.5 g, 1.65 mmol) in HOAc (6.0 mL) was added hydrazine hydrate (0.123 g, 2.47 mmol) and the reaction stirred at 110° C. for 16 hr. The reaction was quenched with water (50 mL) and the precipitate collected and dried to give ethyl 5-methyl-4-oxo-4,5-dihydro-3H-pyridazino[4,5-b]indole-1-carboxylate (0.33 g) as solid. MS: ESI+ve, 273.18 [M+H].

Ethyl 3-benzyl-5-methyl-4-oxo-4,5-dihydro-3H-pyridazino[4,5-b]indole-1-carboxylate

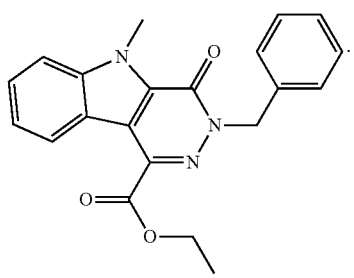 [SMILES: CCOC(=O)c1nn(Cc2ccccc2)c(=O)c2c1c1ccccc1n2C]

NaH (0.037 g, 1.54 mmol) was added a solution of ethyl 5-methyl-4-oxo-4,5-dihydro-3H-pyridazino[4,5-b]indole-1-carboxylate (0.35 g, 1.29 mmol) in THF (5 mL) at 0° C. and stirred at rt for 30 min. The reaction was cooled to 0° C. again, then Bn—Br (0.17 mL, 1.42 mmol) added and the mixture stirred at rt for 12 hr. The reaction was quenched with water (20 mL) and extracted with EtOAc (3×20 mL). The combined organic layers were dried over Na$_2$SO$_4$, and concentrated. The crude product was purified by column chromatography (20% EtOAc/hexane) to give ethyl 3-benzyl-5-methyl-4-oxo-4,5-dihydro-3H-pyridazino[4,5-b]indole-1-carboxylate (0.25 g, 53%) as a solid. MS: ESI+ve, 362.24 [M+H].

3-benzyl-N-ethyl-5-methyl-4-oxo-N-phenyl-4,5-dihydro-3H-pyridazino[4,5-b]indole-1-carboxamide

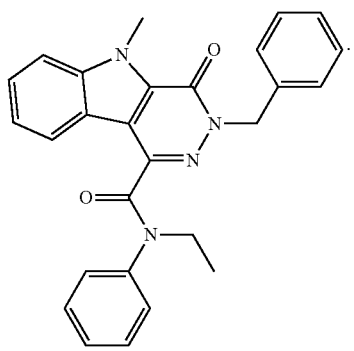 [SMILES: CCN(C(=O)c1nn(Cc2ccccc2)c(=O)c2c1c1ccccc1n2C)c1ccccc1]

Me₃Al (2M in toluene, 1.05 mL, 2.07 mmol) was added dropwise to a stirred solution of N-ethyl aniline (0.15 g, 1.24 mmol) in toluene (5 mL). After stirring the mixture for 2 hr at rt, ethyl 3-benzyl-5-methyl-4-oxo-4,5-dihydro-3H-pyridazino[4,5-b]indole-1-carboxylate (0.150 g, 0.42 mmol) was added and the reaction heated to 110° C. for 2 h. The reaction was quenched with water (20 mL), neutralized with a satd. solution of NaHCO₃ (15 mL) and extracted with EtOAc (3×25 mL). The organic layer was dried over Na₂SO₄, concentrated, and purified by column chromatography (0-30% EtOAc/hexane) to yield 3-benzyl-N-ethyl-5-methyl-4-oxo-N-phenyl-4,5-dihydro-3H-pyridazino[4,5-b]indole-1-carboxamide (0.060 g). MS: ESI+ve, 437.31 [M+H]. ¹H NMR (DMSO-d₆) δ 8.02 (d, J=8 Hz, 1H), 7.80 (m, 1H), 7.68 (m, 1H), 7.49 (m, 1H), 7.24 (m, 3H), 7.19 (m, 3H), 7.05 (m, 2H), 6.85 (m, 2H), 5.14 (s, 2H), 4.23 (s, 3H), 4.05 (q, J=7 Hz, 2H), 1.23 (t, J=7 Hz, 3H).

Representative compounds of the invention were prepared in a similar manner to example 136 (scheme 8):

| Example No. | Structure | IUPAC Name | LCMS m/z |
| --- | --- | --- | --- |
| 137. | 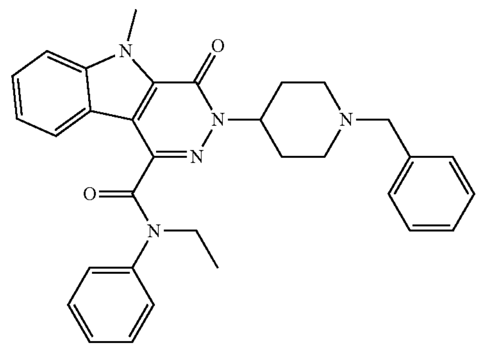 [SMILES: CCN(C(=O)c1nn(C2CCN(Cc3ccccc3)CC2)c(=O)c2c1c1ccccc1n2C)c1ccccc1] | 3-(1-benzylpiperidin-4-yl)-N-ethyl-5-methyl-4-oxo-N-phenyl-4,5-dihydro-3H-pyridazino[4,5-b]indole-1-carboxamide | 520 [M + H] |
| 138. | 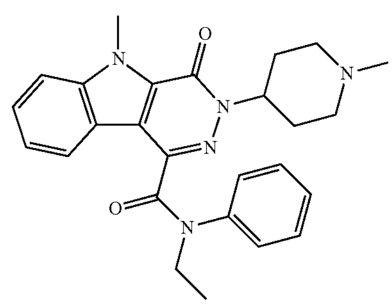 [SMILES: CCN(C(=O)c1nn(C2CCN(C)CC2)c(=O)c2c1c1ccccc1n2C)c1ccccc1] | N-ethyl-5-methyl-3-(1-methylpiperidin-4-yl)-4-oxo-N-phenyl-4,5-dihydro-3H-pyridazino[4,5-b]indole-1-carboxamide | 444 [M + H] |
| 139. | 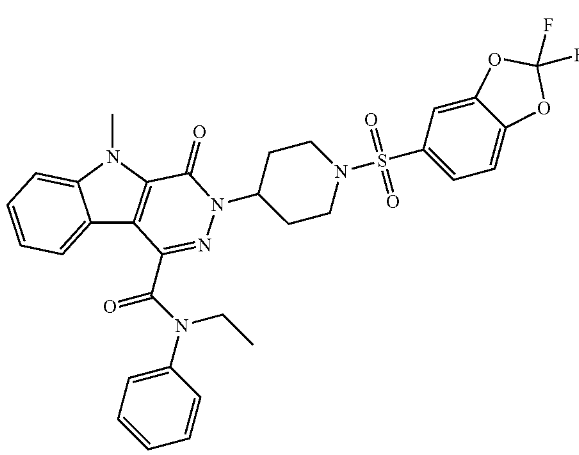 [SMILES: CCN(C(=O)c1nn(C2CCN(S(=O)(=O)c3ccc4c(c3)OC(F)(F)O4)CC2)c(=O)c2c1c1ccccc1n2C)c1ccccc1] | 3-(1-((2,2-difluorobenzo[d][1,3]dioxol-5-yl)sulfonyl)piperidin-4-yl)-N-ethyl-5-methyl-4-oxo-N-phenyl-4,5-dihydro-3H-pyridazino[4,5-b]indole-1-carboxamide | 650 [M + H] |

-continued

| Example No. | Structure | IUPAC Name | LCMS m/z |
|---|---|---|---|
| 140. | 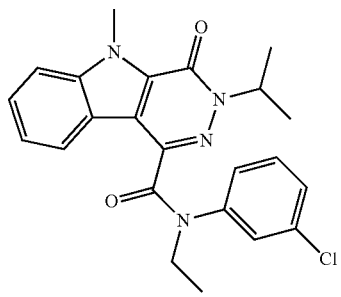 [SMILES: CCN(C(=O)c1nn(C(C)C)c(=O)c2c1c1ccccc1n2C)c1cccc(Cl)c1] | N-(3-chlorophenyl)-N-ethyl-3-isopropyl-5-methyl-4-oxo-4,5-dihydro-3H-pyridazino[4,5-b]indole-1-carboxamide | 423 [M + H] |
| 141. | 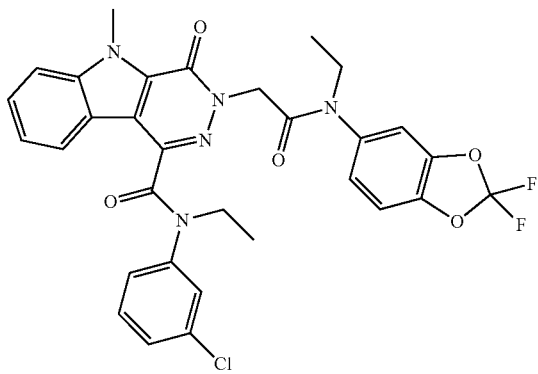 [SMILES: CCN(C(=O)Cn1nc(C(=O)N(CC)c2cccc(Cl)c2)c2c3ccccc3n(C)c2c1=O)c1ccc2c(c1)OC(F)(F)O2] | N-(3-chlorophenyl)-3-(2-((2,2-difluorobenzo[d][1,3]dioxol-5-yl)(ethyl)amino)-2-oxoethyl)-N-ethyl-5-methyl-4-oxo-4,5-dihydro-3H-pyridazino[4,5-b]indole-1-carboxamide | 623 [M + H] |
| 142. | 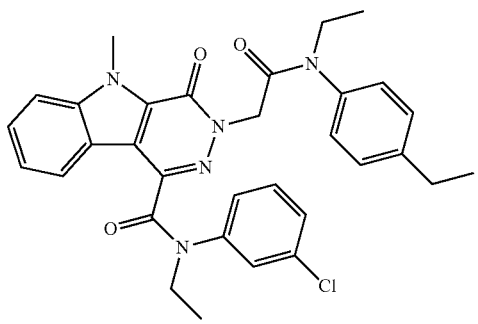 [SMILES: CCc1ccc(N(CC)C(=O)Cn2nc(C(=O)N(CC)c3cccc(Cl)c3)c3c4ccccc4n(C)c3c2=O)cc1] | N-(3-chlorophenyl)-N-ethyl-3-(2-(ethyl(4-ethylphenyl)amino)-2-oxoethyl)-5-methyl-4-oxo-4,5-dihydro-3H-pyridazino[4,5-b]indole-1-carboxamide | 571 [M + H] |
| 143. | 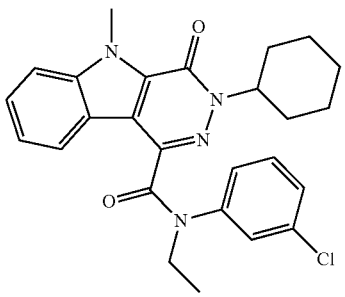 [SMILES: CCN(C(=O)c1nn(C2CCCCC2)c(=O)c2c1c1ccccc1n2C)c1cccc(Cl)c1] | N-(3-chlorophenyl)-3-cyclohexyl-N-ethyl-5-methyl-4-oxo-4,5-dihydro-3H-pyridazino[4,5-b]indole-1-carboxamide | 463 [M + H] |

| Example No. | Structure | IUPAC Name | LCMS m/z |
|---|---|---|---|
| 144. | 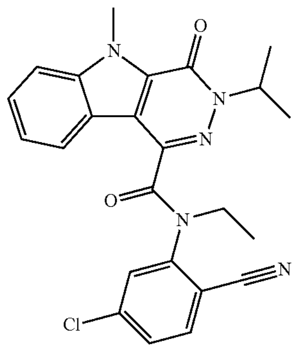 [SMILES: CCN(C(=O)c1nn(C(C)C)c(=O)c2c1c1ccccc1n2C)c1cc(Cl)ccc1C#N] | N-(5-chloro-2-cyanophenyl)-N-ethyl-3-isopropyl-5-methyl-4-oxo-4,5-dihydro-3H-pyridazino[4,5-b]indole-1-carboxamide | 448 [M + H] |
| 145. | 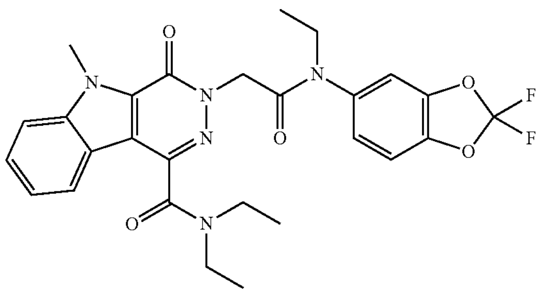 [SMILES: CCN(CC)C(=O)c1nn(CC(=O)N(CC)c2ccc3c(c2)OC(F)(F)O3)c(=O)c2c1c1ccccc1n2C] | 3-(2-((2,2-difluorobenzo[d][1,3]dioxol-5-yl)(ethyl)amino)-2-oxoethyl)-N,N-diethyl-5-methyl-4-oxo-4,5-dihydro-3H-pyridazino[4,5-b]indole-1-carboxamide | 540 [M + H] |

Example 146: 5-cyclobutyl-N-ethyl-4-oxo-N-phenyl-3-p-tolyl-4,5-dihydro-3H-pyridazino[4,5-b]indole-1-carboxamide

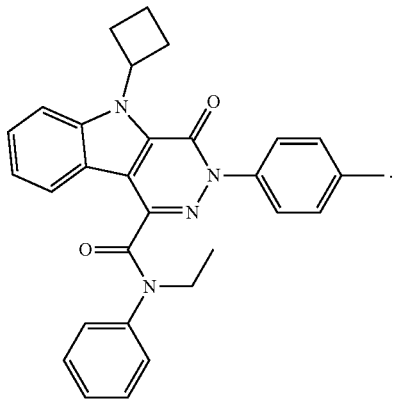 [SMILES: CCN(C(=O)c1nn(-c2ccc(C)cc2)c(=O)c2c1c1ccccc1n2C1CCC1)c1ccccc1]

Ethyl 3-(2-ethoxy-2-oxoacetyl)-1H-indole-2-carboxylate

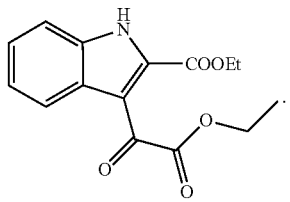 [SMILES: CCOC(=O)C(=O)c1c(C(=O)OCC)[nH]c2ccccc12]

TiCl$_4$ (1.3 mL, 11.6 mmol) was added to a solution of ethyl chloro oxoacetate (1.3 mL, 11.6 mmol) in DCE (40 mL) and the reaction stirred for 30 min at rt. A solution of ethyl 1H-indole-2-carboxylate (2.0 g, 10.5 mmol) in DCE was added dropwise and stirring was continued for 2 hr. The reaction was quenched with water (100 mL) and extracted with DCM (3×100 mL). The combined organic layers were dried over Na$_2$SO$_4$ and concentrated to give ethyl 3-(2-ethoxy-2-oxoacetyl)-1H-indole-2-carboxylate (2.64 g). MS: ESI+ve, 289.94 [M+H].

Ethyl 4-oxo-3-p-tolyl-4,5-dihydro-3H-pyridazino[4,5-b]indole-1-carboxylate

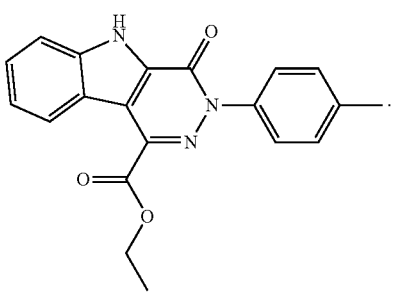 [SMILES: CCOC(=O)c1nn(-c2ccc(C)cc2)c(=O)c2[nH]c3ccccc3c12]

To a stirred solution ethyl 3-(2-ethoxy-2-oxoacetyl)-1H-indole-2-carboxylate (2.64 g, 9.13 mmol) in HOAc (40 mL)

was added p-tolylhydrazine hydrochloride (1.82 g, 11.5 mmol), and reaction was heat at 100° C. for 16 hr. The reaction was quenched with water (50 mL), and the solid product collected by filtration to yield ethyl 4-oxo-3-p-tolyl-4,5-dihydro-3H-pyridazino[4,5-b]indole-1-carboxylate (2.5 g). MS: ESI+ve, 347.98 [M+H].

Example 147: N-Ethyl-4-oxo-N-phenyl-3-p-tolyl-4,5-dihydro-3H-pyridazino[4,5-b]indole-1-carboxamide

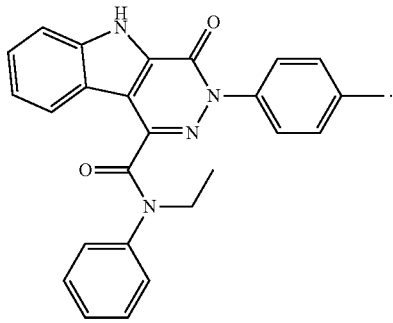 [SMILES: CCN(C(=O)c1nn(-c2ccc(C)cc2)c(=O)c2[nH]c3ccccc3c12)c1ccccc1]

Me$_3$Al (2.0 M in toluene, 7.2 mL, 14.4 mmol) was added dropwise to a stirred solution of N-ethyl aniline (1.04 g, 8.64 mmol) in toluene (20 mL). After stirring the mixture for 2 hr at rt, ethyl 4-oxo-3-p-tolyl-4,5-dihydro-3H-pyridazino[4,5-b]indole-1-carboxylate (1.0 g, 2.88 mmol) was added and the reaction heated to 100° C. for 2 h. The reaction was quenched with water (50 mL), neutralized with a satd. solution of NaHCO$_3$ (100 mL) and extracted with EtOAc (3×75 mL). The organic layer was dried over Na$_2$SO$_4$, then concentrated, and purified by column chromatography (40% EtOAc/hexane) to give N-ethyl-4-oxo-N-phenyl-3-p-tolyl-4,5-dihydro-3H-pyridazino[4,5-b]indole-1-carboxamide (0.4 g). MS: ESI+ve, 423.68 [M+H]. $^1$H NMR (DMSO-d$_6$) δ 13.1 (s, 1H), 8.08 (d, J=8 Hz, 1H), 7.68-7.22 (m, 8H), 7.08 (m, 2H), 6.91 (m, 2H), 4.05 (q, 2H), 1.25 (t, J=7 Hz, 3H).

Example 146: 5-cyclobutyl-N-ethyl-4-oxo-N-phenyl-3-p-tolyl-4,5-dihydro-3H-pyridazino[4,5-b]indole-1-carboxamide

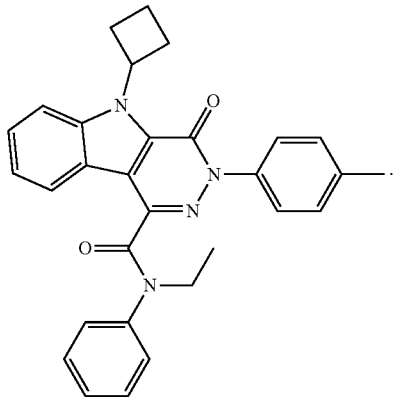 [SMILES: CCN(C(=O)c1nn(-c2ccc(C)cc2)c(=O)c2c1c1ccccc1n2C1CCC1)c1ccccc1]

K$_2$CO$_3$ (0.122 g, 0.88 mmol) was added to a solution of N-ethyl-4-oxo-N-phenyl-3-p-tolyl-4,5-dihydro-3H-pyridazino[4,5-b]indole-1-carboxamide (0.25 g, 0.59 mmol) in acetonitrile (5.0 mL) at rt. After stirring for 30 min, bromo cyclobutane (0.48 g, 3.55 mmol) was added and the reaction heated to reflux for 16 hr. The reaction was quenched with water (50 mL) and extracted with EtOAc (3×40 mL). The organic layer was dried over Na$_2$SO$_4$, then concentrated to obtain crude product, which was purified by column chromatography (15% EtOAc/hexane) to give 5-cyclobutyl-N-ethyl-4-oxo-N-phenyl-3-p-tolyl-4,5-dihydro-3H-pyridazino[4,5-b]indole-1-carboxamide (11.5 mg). MS: ESI+ve, 477.34 [M+H]. $^1$H NMR (CD$_3$CN) δ 8.18 (m, 1H), 8.12 (m, 1H), 7.66 (m, 1H), 7.50 (m, 1H), 7.24 (m, 5H), 7.08 (m, 2H), 6.97 (m, 2H), 6.47 (m, 1H), 4.09 (q, J=7 Hz, 2H), 3.13 (m, 2H), 2.47 (m, 2H), 2.41 (s, 3H), 2.10 (m, 2H), 1.32 (t, J=7 Hz, 3H).

Representative compounds of the invention were prepared in a similar manner to example 146 (scheme 9).

| Example No. | Structure | IUPAC Name | LCMS m/z |
|---|---|---|---|
| 147. | 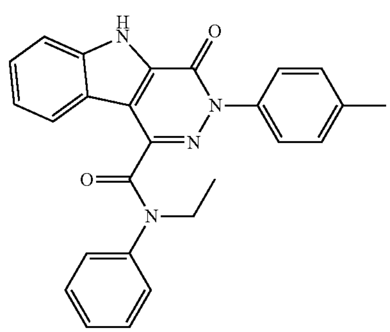 [SMILES: CCN(C(=O)c1nn(-c2ccc(C)cc2)c(=O)c2[nH]c3ccccc3c12)c1ccccc1] | N-ethyl-4-oxo-N-phenyl-3-p-tolyl-4,5-dihydro-3H-pyridazino[4,5-b]indole-1-carboxamide | 423.68 [M + H] |

-continued

| Example No. | Structure | IUPAC Name | LCMS m/z |
|---|---|---|---|
| 148. | 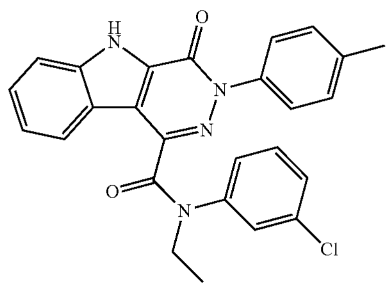 [SMILES: CCN(C(=O)c1nn(-c2ccc(C)cc2)c(=O)c2[nH]c3ccccc3c12)c1cccc(Cl)c1] | N-(3-chlorophenyl)-N-ethyl-4-oxo-3-(p-tolyl)-4,5-dihydro-3H-pyridazino[4,5-b]indole-1-carboxamide | 457 [M + H] |
| 149. | 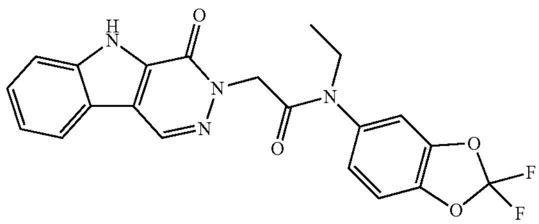 [SMILES: CCN(C(=O)Cn1ncc2c([nH]c3ccccc32)c1=O)c1ccc2c(c1)OC(F)(F)O2] | N-(2,2-difluorobenzo[d][1,3]dioxol-5-yl)-N-ethyl-2-(4-oxo-4,5-dihydro-3H-pyridazino[4,5-b]indol-3-yl)acetamide | 427 [M + H] |
| 150. | 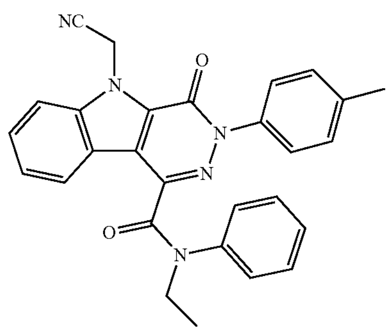 [SMILES: CCN(C(=O)c1nn(-c2ccc(C)cc2)c(=O)c2c1c1ccccc1n2CC#N)c1ccccc1] | 5-(cyanomethyl)-N-ethyl-4-oxo-N-phenyl-3-(p-tolyl)-4,5-dihydro-3H-pyridazino[4,5-b]indole-1-carboxamide | 462 [M + H] |
| 151. | 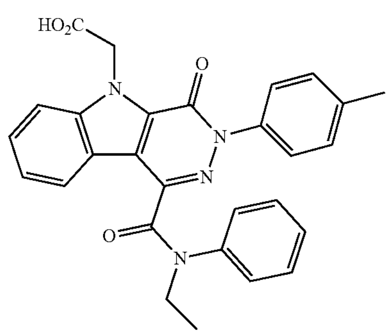 [SMILES: CCN(C(=O)c1nn(-c2ccc(C)cc2)c(=O)c2c1c1ccccc1n2CC(=O)O)c1ccccc1] | 2-(1-(ethyl(phenyl)carbamoyl)-4-oxo-3-(p-tolyl)-3H-pyridazino[4,5-b]indol-5(4H)-yl)acetic acid | 481 [M + H] |
| 152. | 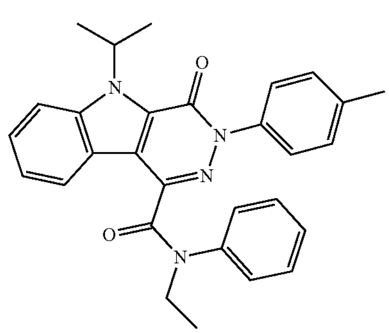 [SMILES: CCN(C(=O)c1nn(-c2ccc(C)cc2)c(=O)c2c1c1ccccc1n2C(C)C)c1ccccc1] | N-ethyl-5-isopropyl-4-oxo-N-phenyl-3-(p-tolyl)-4,5-dihydro-3H-pyridazino[4,5-b]indole-1-carboxamide | 465 [M + H] |

| Example No. | Structure | IUPAC Name | LCMS m/z |
|---|---|---|---|
| 153. | 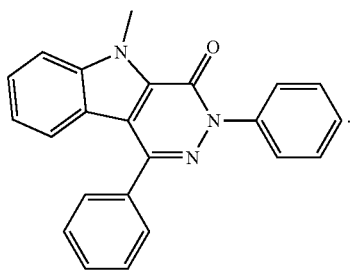 | N-ethyl-4-oxo-N-phenyl-5-(pyridin-2-ylmethyl)-3-(p-tolyl)-4,5-dihydro-3H-pyridazino[4,5-b]indole-1-carboxamide | 514 [M + H] |

Example 154: Synthesis of 1,3-diphenyl-3H-pyridazino[4,5-b]indol-4(5H)-one

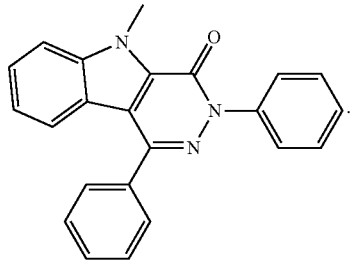 [SMILES: Cn1c2ccccc2c2c(-c3ccccc3)nn(-c3ccccc3)c(=O)c21]

3-Benzoyl-1-methyl-1H-indole-2-carboxylate

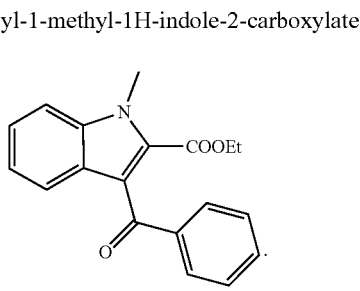

AlCl₃ (0.65 g, 0.49 mmol) was added to a stirred solution of ethyl 1-methyl-1H-indole-2-carboxylate (1.0 g, 0.49 mmol) in DCE (10.0 mL), followed by benzoyl chloride (0.57 mL, 0.49 mmol). The reaction was heated to reflux for 16 hr, then quenched with water (50 mL), neutralized with a satd. solution of NaHCO₃ (100 mL), and extracted with EtOAc (3×100 mL). The combined organic layers were dried over Na₂SO₄ and concentrated to obtained crude product, which was purified by column chromatography (7% EtOAc/hexane) to yield ethyl 3-benzoyl-1-methyl-1H-indole-2-carboxylate (0.5 g). MS: ESI+ve, 309.25 [M+H].

1,3-Diphenyl-3H-pyridazino[4,5-b]indol-4(5H)-one (Example 554)

Phenyl hydrazine (0.105 g, 0.97 mmol) was added to a stirred solution of ethyl 3-benzoyl-1-methyl-1H-indole-2-carboxylate (0.2 g, 0.65 mmol) in HOAc (6.0 mL) and the reaction refluxed for 16 hr. The reaction was quenched with water (10 mL), neutralized with satd. NaHCO₃ (20 mL) and extracted with EtOAc (3×30 mL). The combined organic layers were dried with Na₂SO₄ and concentrated to obtained crude product, which was purified by column chromatography (10% EtOAc/hexane) to yield 1,3-diphenyl-3H-pyridazino[4,5-b]indol-4(5H)-one (0.02 g). MS: ESI+ve, 352.27 [M+H]. ¹H NMR (DMSO-d₆) δ 7.85 (d, J=8 Hz, 1H), 7.76-7.68 (m, 4H), 7.62-7.60 (m, 4H), 7.58 (m, 2H), 7.46-7.40 (m, 2H), 7.26 (m, 1H), 4.38 (s, 3H).

Representative compounds of the invention were prepared in a similar manner to example 154 (scheme 10).

| Example No. | Structure | IUPAC Name | LCMS m/z |
|---|---|---|---|
| 155. | 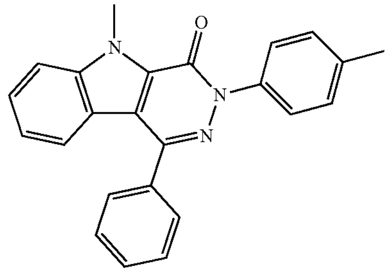 [SMILES: Cc1ccc(-n2nc(-c3ccccc3)c3c4ccccc4n(C)c3c2=O)cc1] | 5-methyl-1-phenyl-3-(p-tolyl)-3H-pyridazino[4,5-b]indol-4(5H)-one | 366 [M + H] |

| Example No. | Structure | IUPAC Name | LCMS m/z |
|---|---|---|---|
| 156. | 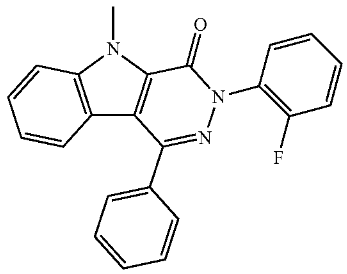 [SMILES: Cn1c2ccccc2c2c(-c3ccccc3)nn(-c3ccccc3F)c(=O)c21] | 3-(2-fluorophenyl)-5-methyl-1-phenyl-3H-pyridazino[4,5-b]indol-4(5H)-one | 370 [M + H] |
| 157. | 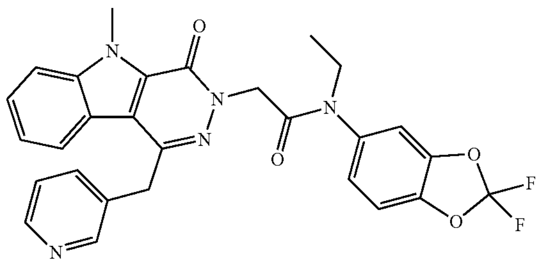 [SMILES: CCN(C(=O)Cn1nc(Cc2cccnc2)c2c3ccccc3n(C)c2c1=O)c1ccc2c(c1)OC(F)(F)O2] | N-(2,2-difluorobenzo[d][1,3]dioxol-5-yl)-N-ethyl-2-(5-methyl-4-oxo-1-(pyridin-3-ylmethyl)-4,5-dihydro-3H-pyridazino[4,5-b]indol-3-yl)acetamide | 532 [M + H] |

Assays for Detecting and Measuring the Effect of Compounds on dF508-CFTR Channels CFRT-YFP High Throughput Assay:

The following protocol is designed to selectively screen small molecule compounds for F508del CFTR corrector activities in the HTS YFP flux assay. In this protocol, the cells are incubated with testing compounds for 24 hours, washed with PBS, stimulated with forskolin and a standard potentiator, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508-CFTR corrector accelerates YFP quenching by increasing the number of CFTR molecules in the testing cell plasma membrane.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human AF508-CFTR and a halide-sensitive yellow fluorescent protein (YFP—H148Q/1152L 25, 22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/mL, and streptomycin 100 μg/mL. G418 (0.75-1.0 mg/mL) and zeocin (3.2 ug/mL) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Test compound was applied to the cells at varying concentrations ranging from 2 nM-40 nM in either a 2-fold or 3-fold dilution series. Cells were incubated in a cell culture incubator at 37° C. with 5% $CO_2$ for 24-26 h. Assay plates were washed with DPBS media (Thermo, cat# SH30028.02) to remove unbound cells and compound. Stimulation media (25 μL) containing 20 μM Forskolin & 30 μM P3 [6-(Ethyl-phenyl-sulfonyl)-4-oxo-1,4-dihydro-quinoline-3-carboxylic acid 2-methoxy-benzylamide] in Hams F-12 coon's modified media was added to the plate wells and incubated at room temperature for 60-120 min. 25 μL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al., (2010).

The following protocol is designed to selectively screen small molecule compounds for F508del CFTR potentiator activities in the HTS YFP flux assay. In this protocol, the cells are incubated at 27 C for 24 hours with homogeneously boosted dF508-CFTR expression in the cell membrane by the low temperature, washed with PBS, stimulated with forskolin, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508del-CFTR potentiators accelerate YFP quenching by increasing CFTR activities in the testing cell plasma membrane.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human ΔF508-CFTR and a halide-sensitive yellow fluorescent protein (YFP-H148Q/I152L 25, 22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/mL, and streptomycin 100 μg/mL. G418 (0.75-1.0 mg/mL) and zeocin (3.2 ug/mL) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Cells were incubated in a cell culture incubator at 37° C. with 5% $CO_2$ for 24-26 h. Assay plates were washed with DPBS media (Thermo, cat# SH30028.02) to remove unbound cells. Test compound was applied to the cells at varying concentrations ranging from 2 nM-40 nM in either a 2-fold or 3-fold dilution series in DPBS and stimulated with 20 μM Forskolin (final concentration) in Hams F-12 coon's modified media. Plates were incubated at room temperature for 60-120 min. 25 μL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al. (2010).

REFERENCES

Galietta, L. J., Jayaraman, S., and Verkman, A. S. Cell-based assay for high-throughput quantitative screening of CFTR chloride transport agonists. Am. J. Physiol Cell Physiol 281(5), C1734, 2001.

Sui J, Cotard S, Andersen J, Zhu P, Staunton J, Lee M, Lin S. (2010) Optimization of a Yellow fluorescent protein-based iodide influx high-throughput screening assay for cystic fibrosis transmembrane conductance regulator (CFTR) modulators. Assay Drug Dev Technol. 2010 December; 8(6):656-68.

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 μL of differentiation Media for at least thirty (30) minutes. One day before the Ussing assay test compounds were added to the basolateral surface of the cells at various test concentrations dissolved in DMSO. The same concentrations of correctors was added to 3 or 4 wells giving a n=3 or n=4 protocol.

Ussing Assay:

Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage stabilizes adjusts before application of voltage clamp.

Compounds were added in the following order.

| Step | Chamber |
| --- | --- |
| 3.0 uM Benzamil for 20 minutes | apical addition only |
| 10 uM Forskolin for 20 minutes | apical + basolateral addition |
| 10 uM Genestein for 20 minutes | apical + basolateral addition |
| 10 uM CFTR-172 for 20 minutes | apical + basolateral addition |
| 20 uM Bumetanide for 30 minutes | basolateral addition only |

The short circuit current and resistances (typically >300 Ω-cm2) from each chamber was recorded every 10 seconds on stored on a PC using Acquire and Analyze (Physiologic Instruments).

Analysis:

Efficacy of test compounds was compared using the average of the forskolin response and the CFTR-172 response of the test compound divided by the average of the forskolin response and the CFTR-172 elicited by the positive control. Normalized scores were tabulated for all compounds and concentrations.

TABLE I

CFTR-YFP High Throughput Assay; The following meanings apply: $EC_{50}$: "+++" refers to $EC_{50}$ < 10 μM, "++" refers to $EC_{50}$ range of between 10-20 μM, "+" refers to $EC_{50}$ > 20 μM. % Efficacy is reported as the Emax normalized to the positive control. "+++" refers to $E_{MAX}$ > 80%, "++" refers to a range of 80%-30%, "+" refers to a range of 30%-10%.

| Example | % Efficacy | EC50 |
| --- | --- | --- |
| 1 | + | ++ |
| 2 | + | +++ |
| 3 | ++ | + |
| 4 | ++ | + |
| 5 | ++ | ++ |
| 6 | ++ | +++ |
| 7 | ++ | + |
| 8 | ++ | +++ |
| 9 | + | +++ |
| 10 | + | + |
| 11 | ++ | ++ |
| 12 | ++ | + |
| 13 | ++ | ++ |
| 14 | ++ | + |
| 15 | + | + |
| 16 | ++ | +++ |
| 17 | ++ | +++ |
| 18 | +++ | ++ |
| 19 | +++ | ++ |
| 20 | ++ | + |
| 21 | +++ | +++ |
| 22 | ++ | +++ |
| 23 | ++ | ++ |
| 24 | + | + |
| 25 | ++ | +++ |
| 26 | ++ | +++ |
| 27 | ++ | +++ |
| 28 | ++ | +++ |
| 29 | ++ | +++ |
| 30 | ++ | +++ |
| 31 | + | +++ |
| 32 | ++ | +++ |
| 33 | ++ | +++ |
| 34 | ++ | +++ |
| 35 | ++ | +++ |
| 36 | ++ | +++ |
| 37 | ++ | +++ |
| 38 | ++ | + |
| 39 | +++ | +++ |
| 40 | ++ | +++ |
| 41 | + | + |
| 42 | + | + |
| 43 | ++ | ++ |
| 44 | +++ | +++ |
| 45 | ++ | +++ |
| 46 | ++ | +++ |
| 47 | ++ | +++ |
| 48 | +++ | +++ |
| 49 | +++ | +++ |
| 50 | +++ | +++ |
| 51 | ++ | +++ |
| 52 | ++ | +++ |
| 53 | +++ | +++ |
| 54 | +++ | +++ |
| 55 | ++ | +++ |
| 56 | +++ | +++ |

TABLE I-continued

CFTR-YFP High Throughput Assay; The following meanings apply: $EC_{50}$: "+++" refers to $EC_{50} < 10$ μM, "++" refers to $EC_{50}$ range of between 10-20 μM, "+" refers to $EC_{50} > 20$ μM. % Efficacy is reported as the Emax normalized to the positive control. "+++" refers to $E_{MAX} > 80\%$, "++" refers to a range of 80%-30%, "+" refers to a range of 30%-10%.

| Example | % Efficacy | EC50 |
|---|---|---|
| 57 | ++ | +++ |
| 58 | +++ | ++ |
| 59 | +++ | +++ |
| 60 | ++ | +++ |
| 61 | ++ | +++ |
| 62 | +++ | +++ |
| 63 | ++ | +++ |
| 64 | ++ | +++ |
| 65 | +++ | +++ |
| 66 | +++ | + |
| 67 | +++ | +++ |
| 69 | +++ | +++ |
| 70 | ++ | +++ |
| 71 | +++ | +++ |
| 72 | ++ | +++ |
| 75 | +++ | +++ |
| 76 | + | +++ |
| 77 | ++ | +++ |
| 78 | ++ | ++ |
| 79 | ++ | +++ |
| 80 | + | + |
| 81 | ++ | ++ |
| 82 | +++ | +++ |
| 83 | ++ | +++ |
| 84 | ++ | +++ |
| 85 | ++ | ++ |
| 86 | ++ | +++ |
| 87 | ++ | +++ |
| 88 | ++ | +++ |
| 89 | ++ | ++ |
| 90 | ++ | ++ |
| 91 | ++ | +++ |
| 92 | ++ | +++ |
| 93 | ++ | +++ |
| 94 | ++ | +++ |
| 95 | ++ | +++ |
| 96 | ++ | +++ |
| 97 | ++ | +++ |
| 101 | ++ | +++ |
| 102 | +++ | +++ |
| 103 | +++ | +++ |
| 104 | +++ | +++ |
| 105 | +++ | +++ |
| 106 | +++ | +++ |
| 107 | +++ | +++ |
| 108 | +++ | +++ |
| 109 | ++ | +++ |
| 110 | +++ | +++ |
| 111 | +++ | +++ |
| 112 | ++ | +++ |
| 113 | + | + |
| 114 | + | + |
| 115 | ++ | ++ |
| 118 | +++ | +++ |
| 119 | +++ | +++ |
| 120 | +++ | +++ |
| 121 | ++ | +++ |
| 122 | + | ++ |
| 123 | ++ | ++ |
| 124 | + | + |
| 125 | +++ | +++ |
| 126 | +++ | +++ |
| 127 | +++ | +++ |
| 128 | +++ | +++ |
| 129 | +++ | +++ |
| 130 | +++ | +++ |
| 131 | ++ | +++ |
| 132 | +++ | +++ |
| 133 | +++ | +++ |
| 134 | ++ | +++ |
| 135 | + | +++ |
| 136 | +++ | + |
| 137 | +++ | +++ |
| 140 | ++ | +++ |
| 141 | +++ | +++ |
| 142 | ++ | +++ |
| 143 | +++ | +++ |
| 144 | +++ | +++ |
| 145 | +++ | +++ |
| 146 | + | ++ |
| 147 | ++ | +++ |
| 148 | ++ | +++ |
| 149 | ++ | +++ |
| 150 | +++ | + |
| 151 | + | + |
| 152 | ++ | + |
| 153 | + | + |
| 157 | +++ | + |

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed:

1. A compound having the formula:

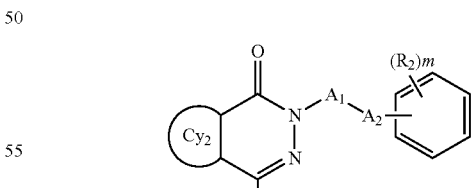

or a pharmaceutically acceptable salt thereof, wherein:
m is 2 to 5;
each $R_2$ is independently selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl —OR$_{100}$, —SR$_{100}$, —NR$_{100}$R$_{101}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$, —CF$_3$, —CN, —NO$_2$, and —N$_3$; provided that two R$_2$ groups, together with the atoms to which they are attached, form an optionally substituted 3, 4, 5, 6 or 7 membered ring;

A$_1$ is —[C(R$_{100}$)(R$_{101}$)]n-, —C(O)—, —C(S)—, —S(O)—, —C(O)N(R$_{100}$)—, —S(O)$_2$N(R$_{100}$)—, —S(O)$_2$—, carbocycle, substituted carbocycle, heterocycle, substituted heterocycle, aromatic, substituted aromatic, heteroaromatic or substituted heteroaromatic;

n is 0, 1, 2, 3, 4, 5, 6 or 7;

each R$_{100}$ and R$_{101}$ is independently hydrogen, deuterium, halogen, alkyl, substituted alkyl, heteroalkyl, substituted heteroalkyl, alkenyl, substituted alkenyl, alkynyl, substituted alkynyl, aliphatic, substituted aliphatic, aryl and substituted aryl; alternatively two R$_{100}$ groups or an R$_{100}$ group and an R$_{101}$ group, together with the atoms to which they are attached and any intervening atoms, form an additional optionally substituted, 3, 4, 5, 6 or 7 membered ring;

A$_2$ is —[C(R$_{100}$)(R$_{101}$)]$_n$—, —C(O)—, —C(S)—, —S(O)—, —C(O)N(R'$_{100}$)—, and —S(O)$_2$;

R'$_{100}$ is alkyl;

A$_3$ is absent;

Cy$_2$ is an aryl or substituted aryl;

Cy$_1$ is an aryl, substituted aryl, carbocycle, substituted carbocycle, heterocyclyl, substituted heterocyclyl, heteroaryl, or substituted heteroaryl group having one, two or three rings.

2. The compound of claim 1 having the formula:

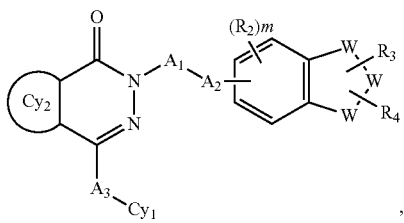

or a pharmaceutically acceptable salt thereof, wherein:
each W is independently CR$_{100}$, C(O), N, NR$_{100}$, O, S, SO, or SO$_2$;

R$_3$ and R$_4$ are each independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, substituted heteroaryl, —SR$_{100}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —S(O)$_2$N(R$_{100}$)R$_{101}$, —CF$_3$, —CN, —NO$_2$, or —N$_3$;

- - - represents a single or double bond; and m is 0, 1, 2, or 3.

3. The compound of claim 1, wherein A$_1$ is C(R$_{100}$)(R$_{101}$) and A$_2$ is —C(O)N(R'$_{100}$)—.

4. The compound according to claim 1, wherein Cy$_1$ is:

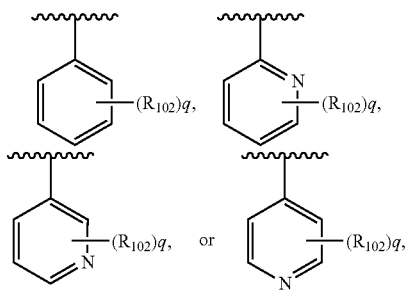

q is 0, 1, 2, 3, or 4; and each R$_{102}$ is hydrogen, deuterium, halogen, alkyl, substituted alkyl, alkenyl, substituted alkenyl, alkynyl, substituted alkynyl, aliphatic, substituted aliphatic, carbocycle, substituted carbocycle, aryl, substituted aryl, —OR$_{100}$, —C(O)R$_{100}$, —C(O)OR$_{100}$, —C(O)NR$_{100}$R$_{101}$, —N(R$_{100}$)C(O)R$_{101}$, —S(O)$_2$R$_{100}$, —S(O)R$_{100}$, —SR$_{100}$, —S(O)$_2$N(R$_{100}$)R$_{101}$ —CF$_3$, —CN, —NO$_2$, or —N$_3$; alternatively two R$_{102}$ groups, together with the atoms to which they are attached and any intervening atoms, form an optionally substituted 3, 4, 5, 6 or 7 membered ring.

5. A pharmaceutical composition comprising a compound according to claim 1 and a pharmaceutically acceptable carrier.

6. The compound of claim 4 wherein Cy$_1$ is

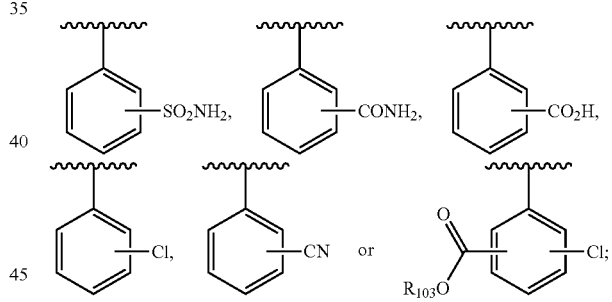

and

R$_{103}$ is hydrogen, deuterium, alkyl, substituted alkyl, alkenyl, substituted alkenyl, alkynyl, substituted alkynyl, aliphatic, substituted aliphatic, aryl or substituted aryl.

7. The compound of claim 1 wherein

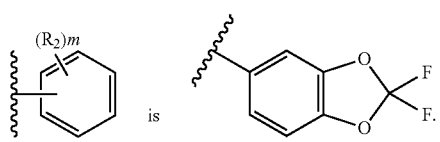

8. A pharmaceutical composition comprising a compound of claim 2 and a pharmaceutically acceptable carrier.

9. A compound selected from Table A, or a pharmaceutically acceptable salt thereof:

| Example No. | Structure |
| --- | --- |
| 18. | 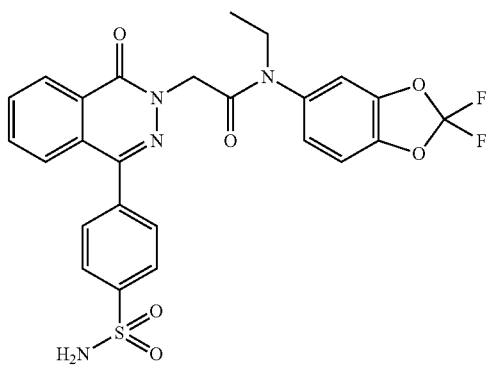 [SMILES: CCN(C(=O)Cn1nc(-c2ccc(S(N)(=O)=O)cc2)c2ccccc2c1=O)c1ccc2c(c1)OC(F)(F)O2] |
| 19. | 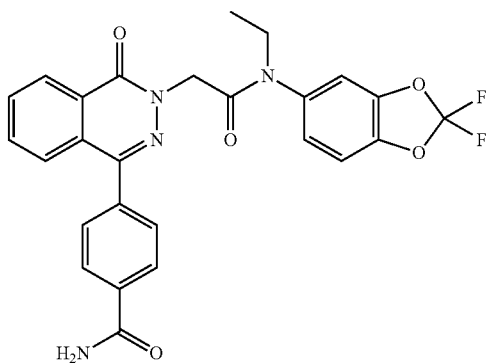 [SMILES: CCN(C(=O)Cn1nc(-c2ccc(C(N)=O)cc2)c2ccccc2c1=O)c1ccc2c(c1)OC(F)(F)O2] |
| 20. | 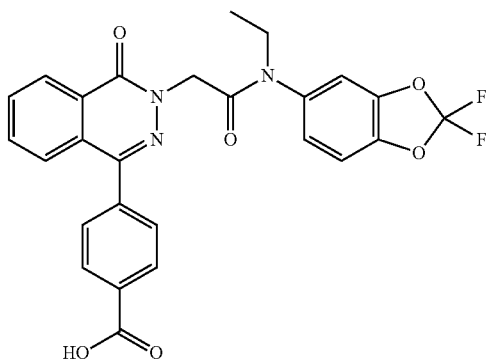 [SMILES: CCN(C(=O)Cn1nc(-c2ccc(C(=O)O)cc2)c2ccccc2c1=O)c1ccc2c(c1)OC(F)(F)O2] |
| 21. | 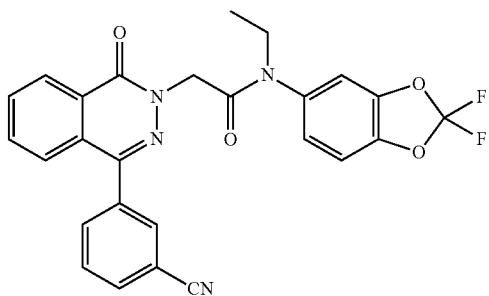 |

-continued
| Example No. | Structure |
|---|---|
| 22. | 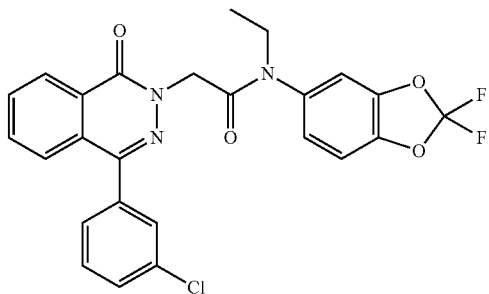 |
| 23. | 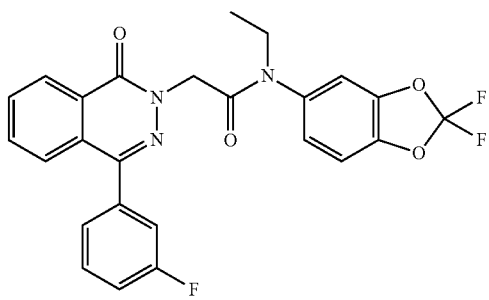 [SMILES: CCN(C(=O)Cn1nc(-c2cccc(Cl)c2)c2ccccc2c1=O)c1ccc2c(c1)OC(F)(F)O2] |
| 24. | 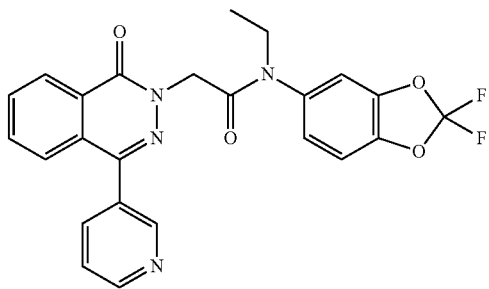 [SMILES: CCN(C(=O)Cn1nc(-c2cccnc2)c2ccccc2c1=O)c1ccc2c(c1)OC(F)(F)O2] |
| 44. | 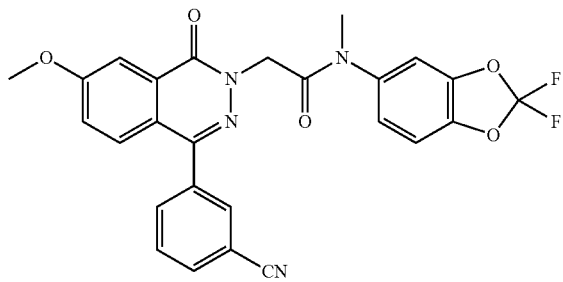 [SMILES: COc1ccc2c(-c3cccc(C#N)c3)nn(CC(=O)N(C)c3ccc4c(c3)OC(F)(F)O4)c(=O)c2c1] |
| 45. | 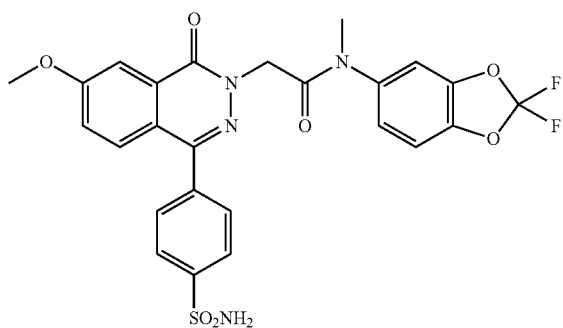 |

| Example No. | Structure |
|---|---|
| 46. | 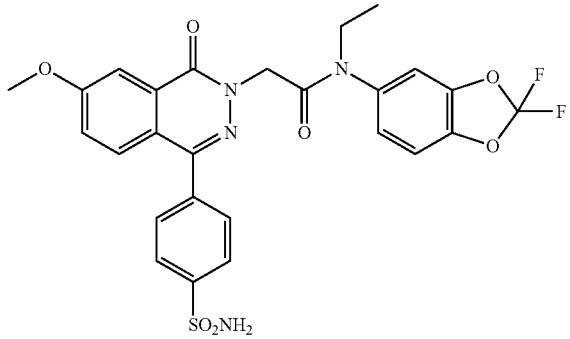 [SMILES: CCN(C(=O)Cn1nc(-c2ccc(S(N)(=O)=O)cc2)c2ccc(OC)cc2c1=O)c1ccc2c(c1)OC(F)(F)O2] |
| 68. | 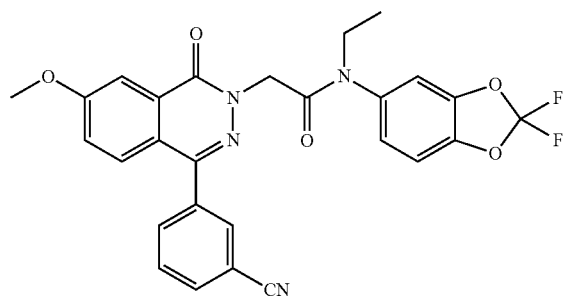 [SMILES: CCN(C(=O)Cn1nc(-c2cccc(C#N)c2)c2ccc(OC)cc2c1=O)c1ccc2c(c1)OC(F)(F)O2] |
| 69. | 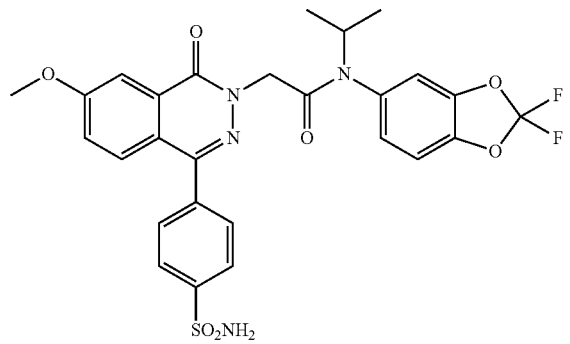 [SMILES: COc1ccc2c(-c3ccc(S(N)(=O)=O)cc3)nn(CC(=O)N(c3ccc4c(c3)OC(F)(F)O4)C(C)C)c(=O)c2c1] |
| 70. | 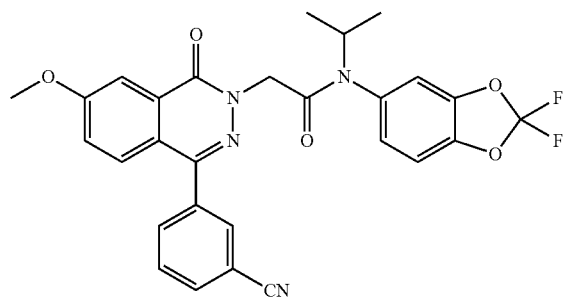 [SMILES: COc1ccc2c(-c3cccc(C#N)c3)nn(CC(=O)N(c3ccc4c(c3)OC(F)(F)O4)C(C)C)c(=O)c2c1] |

| Example No. | Structure |
|---|---|
| 71. | 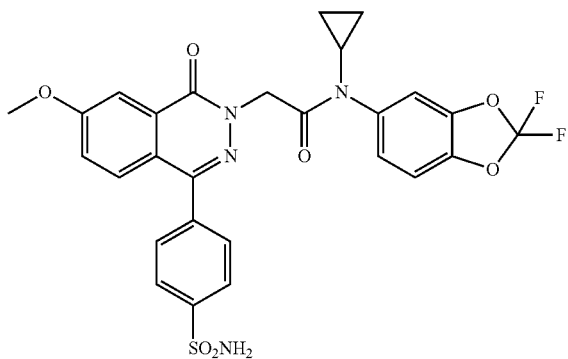 [SMILES: COc1ccc2c(-c3ccc(S(N)(=O)=O)cc3)nn(CC(=O)N(c3ccc4c(c3)OC(F)(F)O4)C3CC3)c(=O)c2c1] |
| 72. | 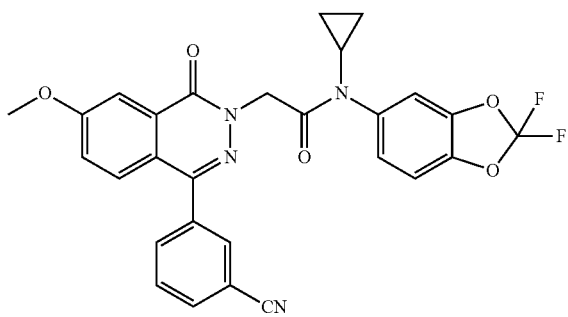 [SMILES: COc1ccc2c(-c3cccc(C#N)c3)nn(CC(=O)N(c3ccc4c(c3)OC(F)(F)O4)C3CC3)c(=O)c2c1] |
| 73. | 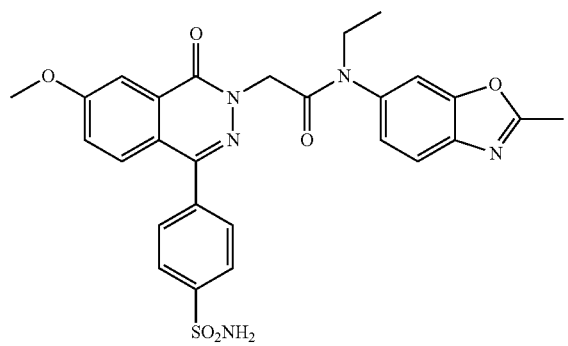 |
| 74. | 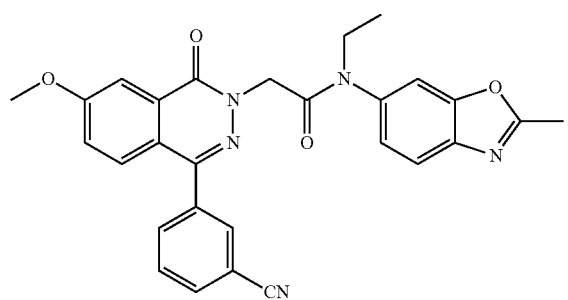 |

| Example No. | Structure |
|---|---|
| 75. | 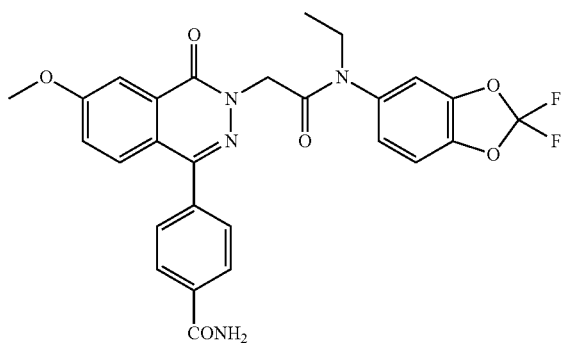 [SMILES: CCN(C(=O)Cn1nc(-c2ccc(C(N)=O)cc2)c2ccc(OC)cc2c1=O)c1ccc2c(c1)OC(F)(F)O2] |
| 76. | 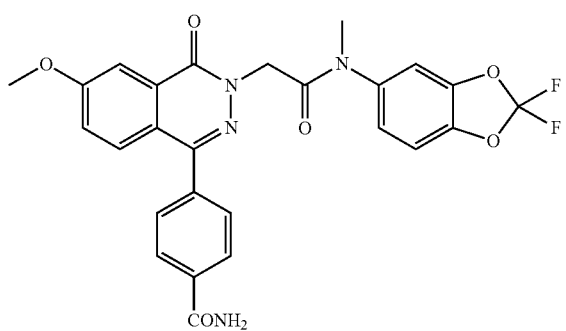 [SMILES: COc1ccc2c(-c3ccc(C(N)=O)cc3)nn(CC(=O)N(C)c3ccc4c(c3)OC(F)(F)O4)c(=O)c2c1] |
| 77. | 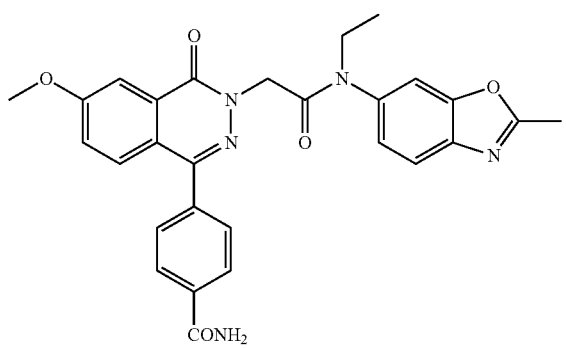 |
| 78. | 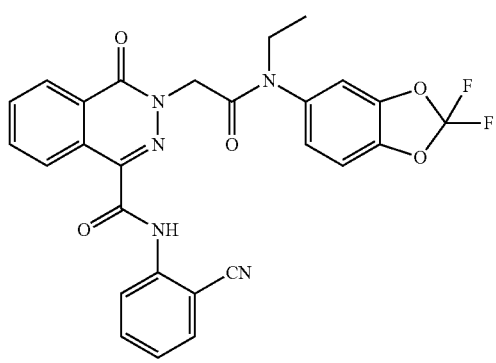 [SMILES: CCN(C(=O)Cn1nc(C(=O)Nc2ccccc2C#N)c2ccccc2c1=O)c1ccc2c(c1)OC(F)(F)O2] |

| Example No. | Structure |
|---|---|
| 79. | 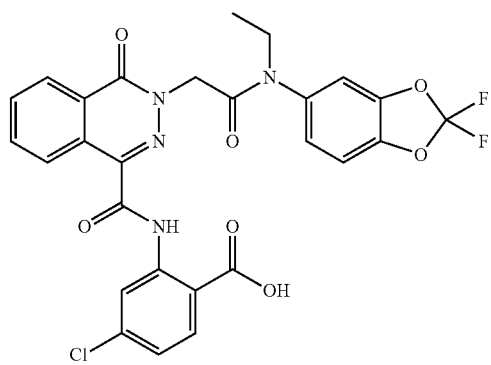 [SMILES: CCN(C(=O)Cn1nc(C(=O)Nc2cc(Cl)ccc2C(=O)O)c2ccccc2c1=O)c1ccc2c(c1)OC(F)(F)O2] |
| 80. | 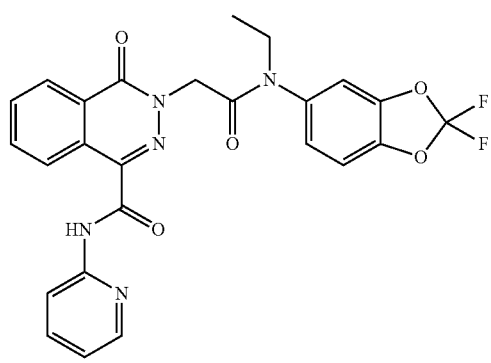 [SMILES: CCN(C(=O)Cn1nc(C(=O)Nc2ccccn2)c2ccccc2c1=O)c1ccc2c(c1)OC(F)(F)O2] |
| 81. | 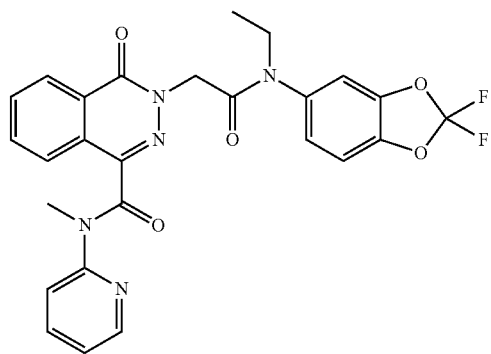 [SMILES: CCN(C(=O)Cn1nc(C(=O)N(C)c2ccccn2)c2ccccc2c1=O)c1ccc2c(c1)OC(F)(F)O2] |
| 83. | 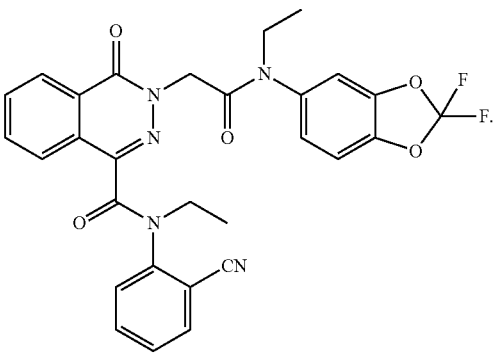 [SMILES: CCN(C(=O)Cn1nc(C(=O)N(CC)c2ccccc2C#N)c2ccccc2c1=O)c1ccc2c(c1)OC(F)(F)O2] |
10. A pharmaceutical composition comprising a compound of claim 9 and a pharmaceutically acceptable carrier.
* * * * *

UNITED STATES PATENT AND TRADEMARK OFFICE
CERTIFICATE OF CORRECTION

PATENT NO. : 9,790,215 B2
APPLICATION NO. : 14/210273
DATED : October 17, 2017
INVENTOR(S) : Bridget M. Cole et al.

It is certified that error appears in the above-identified patent and that said Letters Patent is hereby corrected as shown below:

In the Claims

Column 187, Claim 2, Line 59: after "heteroaryl," insert -- -$OR_{100}$, -- and after "-$SR_{100}$," please insert -- -$NR_{100}R_{101}$, --;

Column 187, Claim 2, Line 61: after "-$S(O)R_{100}$," insert -- -$SR_{100}$, --;

Column 188, Claim 4, Line 22: after "-$OR_{100}$," insert -- -$SR_{100}$, -$NR_{100}R_{101}$, --.

Signed and Sealed this
Twenty-sixth Day of December, 2017

Joseph Matal
*Performing the Functions and Duties of the
Under Secretary of Commerce for Intellectual Property and
Director of the United States Patent and Trademark Office*